United States Patent
Tjon-Joe-Pin et al.

(10) Patent No.: US 10,227,523 B2
(45) Date of Patent: Mar. 12, 2019

(54) GLYCOSYL HYDROLASE ENZYMES IN HIGH TEMPERATURE INDUSTRIAL PROCESSES

(71) Applicant: Advanced Enzyme Systems, LLC, Spring, TX (US)

(72) Inventors: Robert Muko Tjon-Joe-Pin, Spring, TX (US); Moreland David Gibbs, Orakei (NZ); Valentino Setoa Junior Te'o, Brisbane (AU)

(73) Assignee: Advanced Enzyme Systems, LLC, Spring, TX (US)

( * ) Notice: Subject to any disclaimer, the term of this patent is extended or adjusted under 35 U.S.C. 154(b) by 201 days.

(21) Appl. No.: 14/553,701

(22) Filed: Nov. 25, 2014

(65) Prior Publication Data

US 2015/0148267 A1 May 28, 2015

Related U.S. Application Data

(60) Provisional application No. 61/909,012, filed on Nov. 26, 2013.

(51) Int. Cl.
C09K 8/68 (2006.01)
C12N 9/24 (2006.01)

(52) U.S. Cl.
CPC .............. *C09K 8/68* (2013.01); *C12N 9/2491* (2013.01); *C12N 9/2494* (2013.01); *C09K 2208/24* (2013.01)

(58) Field of Classification Search
None
See application file for complete search history.

(56) References Cited

U.S. PATENT DOCUMENTS

| | | |
|---|---|---|
| 5,224,544 A | 7/1993 | Tjon-Joe-Pin et al. |
| 5,247,995 A | 9/1993 | Tjon-Joe-Pin et al. |
| 5,806,597 A | 9/1998 | Tjon-Joe-Pin et al. |
| 6,138,760 A | 10/2000 | Lopez et al. |
| 6,186,235 B1 | 2/2001 | Tjon-Joe-Pin et al. |
| 6,245,547 B1 | 6/2001 | Mathur et al. |
| 6,387,853 B1 | 5/2002 | Dawson et al. |
| 6,566,114 B1 | 5/2003 | Kauppinen |
| 7,195,071 B2 | 3/2007 | Powell et al. |
| 7,517,685 B2 | 4/2009 | Nevalainen et al. |
| 8,088,612 B2 | 1/2012 | Brumm |
| 8,096,360 B2 | 1/2012 | Armstrong |
| 8,486,867 B2 | 7/2013 | Armstrong |
| 2011/0053218 A1 | 3/2011 | Te'o et al. |
| 2012/0157356 A1 | 6/2012 | Dawson et al. |
| 2013/0143295 A1 | 6/2013 | Slupska et al. |
| 2013/0228334 A1 | 9/2013 | Jiang et al. |

FOREIGN PATENT DOCUMENTS

| | | | |
|---|---|---|---|
| CN | 103333839 | * | 10/2013 |
| CN | 103333839 B | | 10/2013 |
| EP | 0280341 A1 | | 8/1988 |
| WO | WO95/17513 A1 | | 6/1995 |

OTHER PUBLICATIONS

Gibbs et al. Sequencing and Expression of a β-Mannanase Gene from the Extreme Thermophile Dictyoglomus thermophilum Rt46B. 1, and Characteristics of the Recombinant Enzyme., Current Microbiology, Dec. 1999, vol. 39, Issue 6, pp. 351-357.*
Abbott, DW, et al. "Analysis of the Structural and Functional Diversity of Plant Cell Wall Specific Family 6 Carbohydrate Binding Modules" Biochemistry 48(43) (2009) 10395-10404.
Bergquist, PL. "Recombinant enzymes from thermophilic microorganisms expressed in fungal hosts" Biochemical Soc'y Trans 32(2) (2004) 293-297.
Brannon, H.D., R. M. Tjon-Joe-Pin. "Biotechnological breakthrough improves performance of moderate to high-temperature fracturing applications," SPE 28513, 1994.
Brumm, PJ et al. "Identification, cloning and characterization of Dictyoglomus Turgidum CeIA, an Endoglucanase with cellulose and mannanase activity" Journal of Life Sciences 5 (2011) 488-496.
Dhawan, S and Kaur, J. "Microbial Mannanases: an overview of production and applications" Crit Rev. Biotechno. 27(4) (2007) 197-216.
EPA816-R-04-003 Chapter 4 Hydraulic Fracturing Fluids, 2004, pp. 1-26.
Fanutti, C, et al. "The Conserved Noncatalytic 40-Residue Sequence in Cellulases and Hemicellulases from Anaerobic Fungi Functions as a Protein Docking Domain" J Biol Chem. 270 (49) (1995) 29314-29322.
Gibbs, M., et al. "Cloning, Sequencing and Expression of a b-Mannanase Gene from the Extreme Thermophile Dictyoglomus thermophilum Rt46B.1, and Characteristics of the Recombinant Enzyme" Current Microbiology 39 (1999) 351-357.
Gibbs, M. et al. "Alteration of the pH optimum of a family 11 xylanase, XynB6 of Dictyoglomus thermophilum" New Biotechnology 27(6) (2010) 803-9.
Gibbs, M et al, "Cloning, Sequencing, and Expression of a Xylanase Gene from the Extreme Thermophile Dictyoglomus thermophilum Rt46B.1 and Activity of the Enzyme on Fiber-Bound Substrate" Appl Environ Microbiol 61(12) (1995) 4403-4408.

(Continued)

*Primary Examiner* — Iqbal H Chowdhury
(74) *Attorney, Agent, or Firm* — Blank Rome LLP

(57) ABSTRACT

Novel hyperthermophilic *Dictyoglomus* beta-mannanases are provided for use in high temperature industrial applications requiring enzymatic hydrolysis of 1,4-β-D-mannosidic linkages in mannans, galactomannans, and glucomannans. Also provided are methods and compositions for fracturing a subterranean formation in which a gellable fracturing fluid is first formed by blending together a hydratable polymer and a *Dictyoglomus* beta-mannanase as an enzyme breaker. An optimized and stabilized recombinant *Dictyoglomus* beta-mannanase is provided that shows superior performance/effectiveness and properties in degrading guar and derivatized guars at pH ranges from 3.0 to 12 and temperatures ranging from 130° F. to in excess of 270° F.

26 Claims, 32 Drawing Sheets

Specification includes a Sequence Listing.

(56) References Cited

OTHER PUBLICATIONS

Hu, K. et al. Performance of a New Thermostable Mannanase in Breaking Guar-Based Fracturing Fluids at High Temperatures with Little Premature Degradation. Appl Biochem Biotechnol 172(3) (2014) 1215-26.

Kyaw, A. et al. "Fracturing Fluid (Guar Polymer Gel) Degradation Study by using Oxidative and Enzyme Breaker" Research Journal of Applied Sciences, Engineering and Technology 4(12) (2012) 1667-1671.

Lever, M. Colorimetric and fluorometric carbohydrate determination with p-hydroxybenzoic acid hydrazide Biochem. Med. 7 (1973) 274-281.

Lever, M. "A new reaction for the colorimetric determination of carbohydrates" Anal. Biochem. 47 (1972) 273-279.

Liu, T. et al."Improved heterologous gene expression in *Trichoderma reesei* by cellobiohydrolase I gene (cbh1) promoter optimization" Acta Biochim Biophys Sin (2008): 158-165.

Lucigen poster, Thermophilic Cellulytic Enzymes, 2011.

Morris, DD, et al. "Cloning of the xynB Gene from Dictyoglomus thermophilum Rt46B.1 and Action of the Gene Product on Kraft Pulp" App. and Environ. Microbiol, 64(5)(1998) 1759-1765.

Needleman, SB and Wunsch, CD, "A general method applicable to the search for similarities in the amino acid sequence of two proteins" Journal of Molecular Biology 48 (1970) 443-453.

Patel, B K, et al. Isolation of an extremely thermophilic chemoorganotrophic anaerobe similar to Dictyoglomus thermophilum from a New Zealand hot spring. Arch. Microbiol. 147 (1987) 21-24.

Saiki, T. et al. "*Dictyoglomus thermophilum* gen. nov., sp. nov., a chemoorganotrophic, anaerobic, thermophilic bacterium" Int J Syst Bacteriol 35 (1985) 253-259.

Te'o, VSJ, et al. "Codon optimization of xylanase gene xynB from the thermophilic bacterium Dictyoglomus thermophilum for expression in the filamentous fungus Trichoderma reesei" FEMS Microbiol Letters 190 (2000) 13-19.

Zhang, B, et al. "A superior, high-performance enzyme for breaking borate cross-linked fracturing fluids under extreme well conditions" SPE 160033 (2012) 1-12.

Dodson RJ, et al. YP_002249896 "mannan endo-1,4-beta-mannosidase [Dictyoglomus thermophilum H-6-12]" NCBI 2008.

Lucas, S. et al. YP_002352217 "mannan endo-1,4-beta-mannosidase [Dictyoglomus turgidum DSM 6724]" NCBI 2008.

Gibbs, MD et al. GI:2582052 "*Dictyoglomus thermophilum* beta-mannanase (manA) gene" NCBI 1997.

\* cited by examiner

*FIG. 1*

Sequence Identity between the Ref Seq of
***D. thermophilum* H-6-12 (YP_002249896.1) and *D. turgidum* DSM 6724
(YP_002352217.1)**

Carbohydrate Binding Module 6 (CBM6)

```
D.therm.  16  SINFSSDEITIEAENGVLNGTYVARQFPGYQGTGYVDGFDKDGDSCSVTFEVKESGMYEL  75
              S+NFS+ EI +EAENGVLNGTYVA+ PGYQGTGYVDGFD+DGDSC++TFEVKE+GMYEL
D.turg.   16  SLNFSTEIVVEAENGVLNGTYVAKNLPGYQGTGYVDGFDRDGDSCTITFEVKEAGMYEL  75
                             N1
D.therm.  76  IIGYAAPYGYKENSLYVNGEFQTNVKFPQSQKFTTVYAGLIPLKNGKNTISIVKSWGWFL  135
              IIGYAAPYGYKENSLYVNG FQTNVKFP SQ FTTVY GLIPLK+GKNTISIVKSWGWFL
D.turg.   76  IIGYAAPYGYKENSLYVNGVFQTNVKFPPSQSFTTVYGGLIPLKSGKNTISIVKSWGWFL  135
                                                                       N2
D.therm. 136  LDYFKIKKAEIPTMNPTNKIVTPNPSKEAQKLMDYLVSIYGKYTLSGQMGYKDAFWIWNI  195
              LDYFK KKAE+PTMNPTNKIVTPNPSKEAQKLMDYLVSIYGKYTLSGQMGYKDAFWIWNI
D.turg.  136  LDYFKIKKAELPTMNPTNKIVTPNPSKEAQKLMDYLVSIYGKYTLSGQMGYKDAFWIWNI  195
                                                         AS1
D.therm. 196  TDKFPAICGFDMMDYSPSRVERGASSRDVEDAIDWWNMGGIVQFQWHWNAPKGLYDTPGK  255
              TDKFPAICGFDM+DYSPSRVERGASSRDVEDAIDWWNMGGIVQFQWHWNAPKGLYDTPGK
D.turg.  196  TDKFPAICGFDMIDYSPSRVERGASSRDVEDAIDWWNMGGIVQFQWHWNAPKGLYDTPGK  255
                  AS2                                AS3
D.therm. 256  EWWRGFYTNATSFDIEYAFNHPESEDYKLIIRDIDAIAVQLKRLQEAKVPILWRPLHEAE  315
              EWWRGFYTNATSFDIEYA NHPESEDYKLIIRDIDAIAVQLKRLQEA+VPILWRPLHEAE
D.turg.  256  EWWRGFYTNATSFDIEYALNHPESEDYKLIIRDIDAIAVQLKRLQEARVPILWRPLHEAE  315
                                                                    AS4
D.therm. 316  GRWFWGAKGPEACKKLWRLLFDRLVNYHKINNLIWVWTTTDSPDALKWYPGDEYVDIVG  375
              GRWFWGAKGPE CKKLWRLLFDRLVNYHKINNLIWVWTTTDSPDALKWYPGDEYVDIVG
D.turg.  316  GRWFWGAKGPEPCKKLWRLLFDRLVNYHKINNLIWVWTTTDSPDALKWYPGDEYVDIVG  375

D.therm. 376  ADIYLKDKDYSPSTGMFYNIVKLFGGKKLVALTENGIIPDPDLMKEQKAYWVWFMTWSGF  435
              AD+YL DK+YSPSTGMFYNIVK+FGGKKLVALTENGIIPDPDLMKEQKAYW WFMTWSGF
D.turg.  376  ADVYLNDKNYSPSTGMFYNIVKIFGGKKLVALTENGIIPDPDLMKEQKAYWAWFMTWSGF  435
                                              AS5
D.therm. 436  ENDPNKNEISHIKRVFNHPFVITKDELPNLKVEE  469  SEQ. ID. NO. 1
              ENDPNKNEISHIKRVFNHPFVITKDELPNLKVEE
D.turg.  436  ENDPNKNEISHIKRVFNHPFVITKDELPNLKVEE  469  SEQ. ID. NO. 2
                  AS6
``` glycosyl hydrolase family 26 region – catalytic domain

FIG. 2

```
1    KLVTPNPSKE AQKLMDYLVS IYGKYTLSGQ MGYKDAFWIW NITDKFPAIC
51   GFDMMDYSPS RVERGASSRD VEDAIDWWNM GGIVQFQWHW NAPKGLYDTP
101  GKEWWRGFYT NATSFDIEYA FNHPESEDYK LIIRDIDAIA VQLKRLQEAK
151  VPILWRPLHE AEGRWFWWGA KGPEACKKLW RLLFDRLVNY HKINNLIWVW
201  TTTDSPDALK WYPGDEYVDI VGADIYLKDK DYSPSTGMFY NIVKLFGGKK
251  LVALTENGII PDPDLMKEQK AYWVWFMTWS GFENDPNKNE ISHIKKVFNH
301  PFVITKDELP NLKVEE    SEQ. ID. NO. 3
```

FIG. 3

```
1    EITIEAENGV LNGTYVARQF PGYQGTGYVD GFDKGDSCS VTFEVKESGM
         N1
51   YELIIGYAAP YGYKENSLYV NGEFQTNVKF PQSQKFTTVY AGLIPLKNGK

101  NTISIVKSWG WFLLDYFKIK KAEI   SEQ. ID. NO. 21
                N2
```

FIG. 4A

```
  1  EITIEAENGV LNGTYVARQF PGYQGTGYVD GFDKDGDSCS VTFEVKESGM
 51  YELIIGYAAP YGYKENSLYV NGEFQTNVKF PQSQKFTTVY AGLIPLKNGK
101  NTISIVKSWG WFLLDYFKIK KAEIPTNKLV TPNPSKEAQK LKLVTPNPSK
151  EAQKLMDYLV SIYGKYTLSG QMGYKDAFWI WNITDKFPAI CGFDMMDYSP
201  SRVERGASSR DVEDAIDWWN MGGIVQFQWH WNAPKGLYDT PGKEWWRGFY
251  TNATSFDIEY AFNHPESEDY KLIIRDIDAI AVQLKRLQEA KVPILWRPLH
301  EAEGRWFWWG AKGPEACKKL WRLLFDRLVN YHKINNLIWV WTTTDSPDAL
351  KWYPGDEYVD IVGADIYLKD KDYSPSTGMF YNIVKLFGGK KLVALTENGI
401  IPDPDLMKEQ KAYWVWFMTW SGFENDPNKN EISHIKKVFN HPFVITKDEL
451  PNLKVEE    SEQ.ID. No. 24
```

FIG. 4B

```
SEQID24   1  EITIEAENGVLNGTYVARQFPGYQGTGYVDGFDKDGDSCSVTFEVKESGMYELIIGYAAP   60
             EITIEAENGVLNGTYVARQFPGYQGTGYVDGFDKDGDSCSVTFEVKESGMYELIIGYAAP
RefSeq   23  EITIEAENGVLNGTYVARQFPGYQGTGYVDGFDKDGDSCSVTFEVKESGMYELIIGYAAP   82
                 N1
SEQID24  61  YGYKENSLYVNGEFQTNVKFPQSQKFTTVYAGLIPLKNGKNTISIVKSWGWFLLDYFKIK  120
             YGYKENSLYVNGEFQTNVKFPQSQKFTTVYAGLIPLKNGKNTISIVKSWGWFLLDYFKIK
RefSeq   83  YGYKENSLYVNGEFQTNVKFPQSQKFTTVYAGLIPLKNGKNTISIVKSWGWFLLDYFKIK  142
                                                                N2
SEQID24 121  KAEIPTNKLVTPNPSKEAQKLKLVTPNPSKEAQKLMDYLVSIYGKYTLSGQMGYKDAFWI  180
             KAEIPT    NP+       KLVTPNPSKEAQKLMDYLVSIYGKYTLSGQMGYKDAFWI
RefSeq  143  KAEIPTM-----NPTN-----KLVTPNPSKEAQKLMDYLVSIYGKYTLSGQMGYKDAFWI  192
                                                        AS1
SEQID24 181  WNITDKFPAICGFDMMDYSPSRVERGASSRDVEDAIDWWNMGGIVQFQWHWNAPKGLYDT  240
             WNITDKFPAICGFDMMDYSPSRVERGASSRDVEDAIDWWNMGGIVQFQWHWNAPKGLYDT
RefSeq  193  WNITDKFPAICGFDMMDYSPSRVERGASSRDVEDAIDWWNMGGIVQFQWHWNAPKGLYDT  252
                  AS2                                AS3
SEQID24 241  PGKEWWRGFYTNATSFDIEYAFNHPESEDYKLIIRDIDAIAVQLKRLQEAKVPILWRPLH  300
             PGKEWWRGFYTNATSFDIEYAFNHPESEDYKLIIRDIDAIAVQLKRLQEAKVPILWRPLH
RefSeq  253  PGKEWWRGFYTNATSFDIEYAFNHPESEDYKLIIRDIDAIAVQLKRLQEAKVPILWRPLH  312
SEQID24 301  EAEGRWFWWGAKGPEACKKLWRLLFDRLVNYHKINNLIWVWTTTDSPDALKWYPGDEYVD  360
             EAEGRWFWWGAKGPEACKKLWRLLFDRLVNYHKINNLIWVWTTTDSPDALKWYPGDEYVD
RefSeq  313  EAEGRWFWWGAKGPEACKKLWRLLFDRLVNYHKINNLIWVWTTTDSPDALKWYPGDEYVD  372
             AS4
SEQID24 361  IVGADIYLKDKDYSPSTGMFYNIVKLFGGKKLVALTENGIIPDPDLMKEQKAYWVWFMTW  420
             IVGADIYLKDKDYSPSTGMFYNIVKLFGGKKLVALTENGIIPDPDLMKEQKAYWVWFMTW
RefSeq  373  IVGADIYLKDKDYSPSTGMFYNIVKLFGGKKLVALTENGIIPDPDLMKEQKAYWVWFMTW  432
                                           AS5
SEQID24 421  SGFENDPNKNEISHIKKVFNHPFVITKDELPNLKVEE  457
             SGFENDPNKNEISHIKKVFNHPFVITKDELPNLKVEE
RefSeq  433  SGFENDPNKNEISHIKKVFNHPFVITKDELPNLKVEE  469  (SEQ. ID. NO. 1)
                    AS6
```

*Fig. 5*

```
AAATTAGTAACCCCTAATCCATCAAAAGAGGCCCAAAAATTAATGGACTA    50
TTTAGTGAGTATATATGGAAAGTATACTCTCTCGGGTCAGATGGGATATA    100
AAGATGCCTTCTGGATTTGGAATATTACTGATAAGTTTCCAGCTATATGT    150
GGTTTTGACATGATGGACTACTCACCTTCAAGGGTTGAAAGAGGAGCATC    200
TTCAAGAGATGTGGAAGATGCTATAGATTGGTGGAATATGGGAGGAATAG    250
TTCAATTTCAATGGCACTGGAATGCTCCAAAGGGACTTTATGATACTCCA    300
GGAAAAGAATGGTGGAGAGGCTTTTACACTAATGCTACCAGTTTTGATAT    350
AGAATATGCTTTCAACCACCCTGAATCTGAAGATTACAAACTTATAATAA    400
GGGATATAGATGCTATTGCAGTACAATTAAAAAGACTTCAAGAGGCAAAA    450
GTCCCCATACTATGGAGACCTTTACACGAGGCAGAAGGTAGATGGTTCTG    500
GTGGGGAGCAAAAGGTCCTGAAGCTTGTAAAAAACTATGGAGACTACTTT    550
TTGATAGGCTTGTAAATTATCATAAAATAAATAATCTTATATGGGTTTGG    600
ACTACTACAGACTCTCCTGATGCTCTCAAATGGTATCCTGGAGATGAATA    650
TGTAGATATTGTAGGAGCAGATATATACCTTAAAGATAAAGATTATTCTC    700
CATCTACAGGAATGTTCTATAACATTGTAAAACTATTTGGTGGGAAAAAA    750
CTCGTAGCTCTCACAGAAAATGGAATTATTCCAGATCCAGATTTAATGAA    800
AGAGCAAAAAGCTTATTGGGTATGGTTTATGACCTGGTCAGGTTTTGAAA    850
ATGATCCAAACAAAAACGAAATCTCTCATATTAAAAAGTATTTAATCAT    900
CCCTTTGTAATTACAAAAGATGAGCTACCAAATTTGAAAGTTGAAGAATA    950
A                                                   951
```

SEQ. ID. NO. 26

*Fig. 6*

```
ATGGAAATTACTATTGAAGCAGAAAATGGGGTATTAAACGGAACCTATGT     50
AGCAAGACAATTTCCTGGATATCAAGGCACAGGATATGTGGATGGATTTG    100
ATAAGGATGGAGATTCTTGTAGTGTAACTTTTGAAGTAAAGGAGTCTGGA    150
ATGTACGAATTAATAATTGGATATGCTGCACCCTATGGATATAAGGAAAA    200
TTCCCTTTATGTAAATGGAGAATTTCAAACCAATGTCAAATTTCCCCAAT    250
CTCAAAAATTTACAACCGTATATGCTGGTTTAATTCCTTTAAAAAATGGA    300
AAAAATACAATAAGTATAGTAAAAGCTGGGGATGGTTTCTTCTTGACTA    350
CTTTAAAATCAAAAGGCAGAAATTCCTACCATGAATCCTACAAACAAAT    400
TAGTAACCCCTAATCCATCAAAAGAGGCCCAAAAATTAATGGACTATTTA    450
GTGAGTATATATGGAAAGTATACTCTCTCGGGTCAGATGGGATATAAAGA    500
TGCCTTCTGGATTTGGAATATTACTGATAAGTTTCCAGCTATATGTGGTT    550
TTGACATGATGGACTACTCACCTTCAAGGGTTGAAAGAGGAGCATCTTCA    600
AGAGATGTGGAAGATGCTATAGATTGGTGGAATATGGGAGGAATAGTTCA    650
ATTTCAATGGCACTGGAATGCTCCAAAGGGACTTTATGATACTCCAGGAA    700
AAGAATGGTGGAGAGGCTTTTACACTAATGCTACCAGTTTTGATATAGAA    750
TATGCTTTCAACCACCCTGAATCTGAAGATTACAAACTTATAATAAGGGA    800
TATAGATGCTATTGCAGTACAATTAAAAAGACTTCAAGAGGCAAAAGTCC    850
CCATACTATGGAGACCTTTACACGAGGCAGAAGGTAGATGGTTCTGGTGG    900
GGAGCAAAAGGTCCTGAAGCTTGTAAAAAACTATGGAGACTACTTTTTGA    950
TAGGCTTGTAAATTATCATAAAATAAATAATCTTATATGGGTTTGGACTA   1000
CTACAGACTCTCCTGATGCTCTCAAATGGTATCCTGGAGATGAATATGTA   1050
GATATTGTAGGAGCAGATATATACCTTAAAGATAAAGATTATTCTCCATC   1100
TACAGGAATGTTCTATAACATTGTAAAACTATTTGGTGGGAAAAAACTCG   1150
TAGCTCTCACAGAAATGGAATTATTCCAGATCCAGATTTAATGAAAGAG   1200
CAAAAAGCTTATTGGGTATGGTTTATGACCTGGTCAGGTTTTGAAAATGA   1250
TCCAAACAAAACGAAATCTCTCATATTAAAAAGTATTTAATCATCCCT    1300
TTGTAATTACAAAAGATGAGCTACCAAATTTGAAAGTTGAAGAATAA     1347
```

SEQ. ID. NO. 27

FIG. 7A

```
Opt.    1  ATGCACGAACTGATTATTGGTTACGCAGCACCGTATGGCTATAAAGAAAACAGCCTGTAT
Orig.      ATGCACGAATTAATAATTGGATATGCTGCACCCTATGGATATAAGGAAAATTCCCTTTAT Opt.   61  GTGAACGGCGAATTTCAAACGAACGTCAAATTTCCGCAGTCACAAAAGTTCACCACGGTC
Orig.      GTAAATGGAGAATTTCAAACCAATGTCAAATTTCCCCAATCTCAAAAATTTACAACCGTA Opt.  121  TACGCGGGTCTGATTCCGCTGAAAAACGGCAAGAATACCATTAGCATCGTTAAATCTTGG
Orig.      TATGCTGGTTTAATTCCTTTAAAAAATGGAAAAAATACAATAAGTATAGTAAAAAGCTGG Opt.  181  GGTTGGTTCCTGCTGGATTACTTCAAGATTAAAAAGGCCGAAATCCCGACGATGAACCCG
Orig.      GGATGGTTTCTTCTTGACTACTTTAAAAATCAAAAAGGCAGAAATTCCTACCATGAATCCT Opt.  241  ACCAATAAACTGGTGACCCCGAACCCGTCCAAAGAAGCACAGAAGCTGATGGATTACCTG
Orig.      ACAAACAAATTAGTAACCCCTAATCCATCAAAAGAGGCCCAAAAATTAATGGACTATTTA Opt.  301  GTTAGCATTTATGGCAAATACACGCTGTCCGGCCAAATGGGTTATAAGGACGCGTTCTGG
Orig.      GTGAGTATATATGGAAAGTATACTCTCGGGTCAGATGGGATATAAAGATGCCTTCTGG Opt.  361  ATCTGGAACATCACCGATAAGTTCCCGGCCATCTGCGGTTTCGATATGATGGACTACAGT
Orig.      ATTTGGAATATTACTGATAAGTTTCCAGCTATATGTGGTTTTGACATGATGGACTACTCA Opt.  421  CCGTCCCGTGTTGAACGCGGCGCGAGCTCTCGTGATGTCGAAGACGCCATTGATTGGTGG
Orig.      CCTTCAAGGGTTGAAAGAGGAGCATCTTCAAGAGATGTGGAAGATGCTATAGATTGGTGG Opt.  481  AACATGGGCGGTATCGTGCAGTTTCAATGGCATTGGAATGCCCCGAAAGGCCTGTATGAT
Orig.      AATATGGGAGGAATAGTTCAATTTCAATGGCACTGGAATGCTCCAAAGGGACTTTATGAT Opt.  541  ACCCCGGGCAAGGAATGGTGGCGCGGCTTTTATACGAACGCAACCTCATTCGACATTGAA
Orig.      ACTCCAGGAAAAGAATGGTGGAGAGGCTTTTACACTAATGCTACCAGTTTTGATATAGAA Opt.  601  TACGCTCTGAATCACCCGGAATCGGAAGATTACAAACTGATCATCCGTGATATCGACGCG
Orig.      TATGCTCTCAACCACCCTGAATCTGAAGATTACAAACTTATAATAAGGGATATAGATGCT Opt.  661  ATCGCCGTCCAGCTGAAACGCCTGCAAGAAGCAAAGGTGCCGATCCTGTGGCGTCCGCTG
Orig.      ATTGCAGTACAATTAAAAAGACTTCAAGAGGCAAAAGTCCCCATACTATGGAGACCTTTA Opt.  721  CATGAAGCTGAAGGTCGCTGGTTTTGGTGGGGCGCAAAAGGTCCGGAAGCGTGCAAAAAG
Orig.      CACGAGGCAGAAGGTAGATGGTTCTGGTGGGGAGCAAAAGGTCCTGAAGCTTGTAAAAAA Opt.  781  CTGTGGCGTCTGCTGTTCGATCGCCTGGTTAACTACCACAAGATCAACAACCTGATCTGG
Orig.      CTATGGAGACTACTTTTTGATAGGCTTGTAAATTATCATAAAATAAATAATCTTATATGG Opt.  841  GTCTGGACCACGACCGACAGCCCGGATGCGCTGAAATGGTATCCGGGTGACGAATACGTG
Orig.      GTTTGGACTACTACAGACTCTCCTGATGCTCTCAAATGGTATCCTGGAGATGAATATGTA Opt.  902  GATATTGTTGGCGCCGATATCTATCTGAAAGATAAGGACTACTCACCGAGCACCGGCATG
Orig.      GATATTGTAGGAGCAGATATATACCTTAAAGATAAAGATTATTCTCCATCTACAGGAATG
            - Continue on next page -
```

FIG. 7B

Sequence continued -

```
Opt.    962 TTTTACAACATTGTGAAACTGTTCGGCGGTAAAAAGCTGGTTGCACTGACCGAAAATGGC
Orig.       TTCTATAACATTGTAAAACTATTTGGTGGGAAAAAACTCGTAGCTCTCACAGAAAATGGA Opt.   1021 ATTATCCCGGACCCGGATCTGATGAAAGAACAGAAGGCTTATTGGGTGTGGTTTATGACG
Orig.       ATTATTCCAGATCCAGATTTAATGAAAGAGCAAAAAGCTTATTGGGTATGGTTTATGACC Opt.   1082 TGGAGCGGCTTCGAAAATGACCCGAACAAGAACGAAATTTCTCATATCAAAAAGGTCTTT
Orig.       TGGTCAGGTTTTGAAAATGATCCAAACAAAAACGAAATCTCTCATATTAAAAAAGTATTT Opt.   1142 AACCACCCGTTCGTGATTACCAAAGATGAACTGCCGAATCTGAAGGTTGAAGAATAA SEQ.ID.NO. 28
Orig.       AATCATCCCTTTGTAATTACAAAAGATGAGCTACCAAACTTGAAAGTTGAAGAATAA SEQ.ID.NO. 29
```

FIG. 7C

```
 72 MYEL . . . . (begin alignment with SEQ.ID. NO. 1)

1  MHELIIGYAA PYGYKENSLY VNGEFQTNVK FPQSQKFTTV YAGLIPLKNG KNTISIVKSW
 61  GWFLLDYFKI KKAEIPTMNP TNKLVTPNPS KEAQKLMDYL VSIYGKYTLS GQMGYKDAFW
        N2
121  IWNITDKFPA ICGFDMMDYS PSRVERGASS RDVEDAIDWW NMGGIVQFQW HWNAPKGLYD
181  TPGKEWWRGF YTNATSFDIE YALNHPESED YKLIIRDIDA IAVQLKRLQE AKVPILWRPL
241  HEAEGRWFWW GAKGPEACKK LWRLLFDRLV NYHKINNLIW VWTTTDSPDA LKWYPGDEYV
301  DIVGADIYLK DKDYSPSTGM FYNIVKLFGG KKLVALTENG IIPDPDLMKE QKAYWVWFMT
361  WSGFENDPNK NEISHIKKVF NHPFVITKDE LPNLKVEE       SEQ. ID. NO. 30
```

FIG. 8a

Schematic showing one DNA expression cassette design for expression in *Trichoderma reesei*.

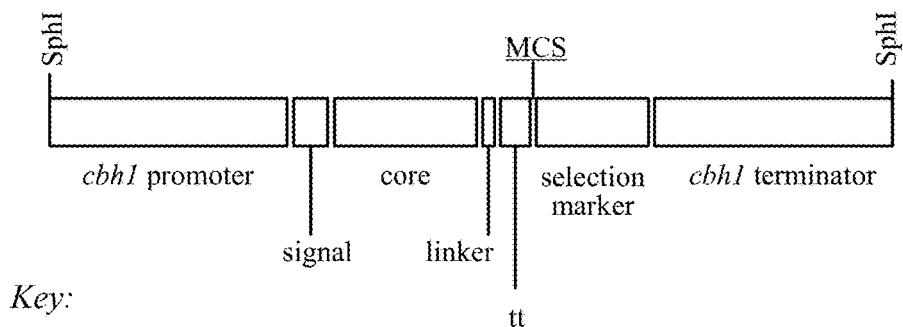

Key:

signal - *T. reesei* CBH1 secretion signal sequence
core - *T. reesei* CBHI core region
tt - *T. reesei* truncated terminator
MCS - multiple cloning site: *SnaB*I – *Kpn*I, *Xho*I, *Sal*I, *Nhe*I, *Afl*II

FIG. 8b

Schematic showing further details of another exemplary DNA expression cassette design for expression in *Trichoderma reesei*.

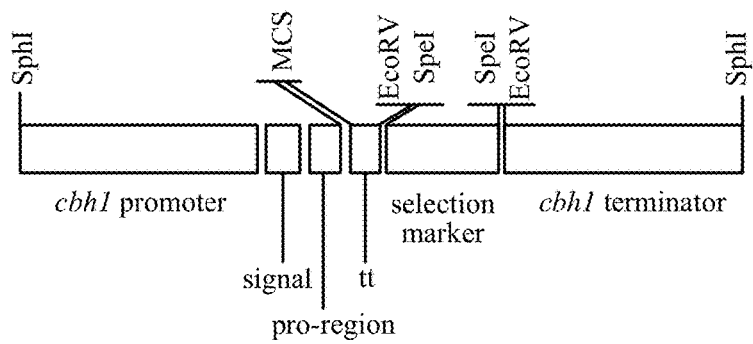

Key:
MCS - multiple cloning site: *Pml*I, *Xho*I, *Sal*I, *She*I, *Afl*II
tt - *T. reesei* truncated terminator
pro-region - N-terminal pro-region of the *T. reesei* XynII xylanase
signal - *T. reesei* CBH1 secretion signal sequence

FIG. 9A

```
        N         P   ┌─────────────────────────────────────────────┐
        c         m   │ Begin Carbohydrate Binding Module 6 (CBM6)  │
        o         l   └─────────────────────────────────────────────┘
        I         I   ┌──→
          ccatggcacacgtg GAGATCACCATCGAGGCCGAgAAcGGCGTCCTCAACGGCACCTACG
  1       ----------+----------+----------+----------+----------+----------+  60
          ggtaccgtgtgcac CTCTAGTGGTAGCTCCGGCTcTTgCCGCAGGAGTTGCCGTGGATGC
           M  A  H  V   E  I  T  I  E  A  E  N  G  V  L  N  G  T  Y  V -
                        └─────────────→

TCGCtCGCCAGTTtCCTGGCTATCAaGGCACTGGCTACGTCGATGGCTTCGACAAaGACG
  61      ----------+----------+----------+----------+----------+----------+ 120
          AGCGaGCGGTCAAaGGACCGATAGTtCCGTGACCGATGCAGCTACCGAAGCTGTTtCTGC
           A  R  Q  F  P  G  Y  Q  G  T  G  Y  V  D  G  F  D  K  D  G -

GCGAtAGCTGCTCCGTCACGTTCGAaGTCAAGGAGTCCGGCATGTACGAaCTTATCATtG
 121      ----------+----------+----------+----------+----------+----------+ 180
          CGCTaTCGACGAGGCAGTGCAAGCTtCAGTTCCTCAGGCCGTACATGCTtGAATAGTAaC
           D  S  C  S  V  T  F  E  V  K  E  S  G  M  Y  E  L  I  I  G -

GCTACGCCGCaCCTTACGGTTACAAGGAGAACTCCCTGTACGTCAACGGCGAGTTCCAGA
 181      ----------+----------+----------+----------+----------+----------+ 240
          CGATGCGGCGtGGAATGCCAATGTTCCTCTTGAGGGACATGCAGTTGCCGCTCAAGGTCT
           Y  A  A  P  Y  G  Y  K  E  N  S  L  Y  V  N  G  E  F  Q  T -

CCAACGTCAAaTTtCCaCAGTCTCAGAAGTTTACTACTGTCTACGCCGGCCTGATtCCTC
 241      ----------+----------+----------+----------+----------+----------+ 300
          GGTTGCAGTTtAAaGGtGTCAGAGTCTTCAAATGATGACAGATGCGGCCGGACTAaGGAG
           N  V  K  F  P  Q  S  Q  K  F  T  T  V  Y  A  G  L  I  P  L -

TCAAGAATGGtAAgAACACCATCTCCATCGTCAAGTCCTGGGGATGGTTCCTCCTGGACT
 301      ----------+----------+----------+----------+----------+----------+ 360
          AGTTCTTACCaTTcTTGTGGTAGAGGTAGCAGTTCAGGACCCCTACCAAGGAGGACCTGA
           K  N  G  K  N  T  I  S  I  V  K  S  W  G  W  F  L  L  D  Y -

ACTTCAAGATCAAGAAGGCCGAGATtCCCACCATGAACCCTACCAACAAaCTCGTCACaC
 361      ----------+----------+----------+----------+----------+----------+ 420
          TGAAGTTCTAGTTCTTCCGGCTCTAaGGGTGGTACTTGGGATGGTTGTTtGAGCAGTGtG
           F  K  I  K  K  A  E  I  P  T  M  N  P  T  N  K  L  V  T  P -

CCAACCCaTCCAAGGAGGCCCAGAAGCTCATGGACTACCTCGTCTCTATCTACGGCAAGT
 421      ----------+----------+----------+----------+----------+----------+ 480
          GGTTGGGtAGGTTCCTCCGGGTCTTCGAGTACCTGATGGAGCAGAGATAGATGCCGTTCA
           N  P  S  K  E  A  Q  K  L  M  D  Y  L  V  S  I  Y  G  K  Y -
```

- Sequence continued -

*FIG. 9B*

```
       - Continuing sequence -
       ACACCCTCTCTGGCCAGATGGGATACAAGGAtGCCTTCTGGATCTGGAACATCACCGACA
481    ---------+---------+---------+---------+---------+---------+ 540
       TGTGGGAGAGACCGGTCTACCCTATGTTCCTaCGGAAGACCTAGACCTTGTAGTGGCTGT
           T  L  S  G  Q  M  G  Y  K  D  A  F  W  I  W  N  I  T  D  K  -

AaTTtCCCGCGATTTGCGGATTCGATATGATGGATTACTCgCCCTCgCGCGTCGAaCGTG
541    ---------+---------+---------+---------+---------+---------+ 600
       TtAAaGGGCGCTAAACGCCTAAGCTATACTACCTAATGAGcGGGAGcGCGCAGCTtGCAC
           F  P  A  I  C  G  F  D  M  M  D  Y  S  P  S  R  V  E  R  G  -

GCGCCTCCTCCCGAGACGTCGAaGACGCCATCGACTGGTGGAACATGGGCGGTATCGTTC
601    ---------+---------+---------+---------+---------+---------+ 660
       CGCGGAGGAGGGCTCTGCAGCTtCTGCGGTAGCTGACCACCTTGTACCCGCCATAGCAAG
           A  S  S  R  D  V  E  D  A  I  D  W  W  N  M  G  G  I  V  Q  -

AGTTCCAaTGGCACTGGAACGCTCCCAAGGGtCTGTATGAtACCCCTGGAAAGGAGTGGT
661    ---------+---------+---------+---------+---------+---------+ 720
       TCAAGGTtACCGTGACCTTGCGAGGGTTCCCaGACATACTaTGGGGACCTTTCCTCACCA
           F  Q  W  H  W  N  A  P  K  G  L  Y  D  T  P  G  K  E  W  W  -

GGCGCGGCTTCTACACTAACGCTACCTCCTTTGACATTGAGTACGCGTTCAACCAtCCCG
721    ---------+---------+---------+---------+---------+---------+ 780
       CCGCGCCGAAGATGTGATTGCGATGGAGGAAACTGTAACTCATGCGCAAGTTGGTaGGGC
           R  G  F  Y  T  N  A  T  S  F  D  I  E  Y  A  F  N  H  P  E  -

AGTCCGAGGACTACAAACTCATCATCAGGGACATTGACGCGATTGCTGTCCAGCTCAAGA
781    ---------+---------+---------+---------+---------+---------+ 840
       TCAGGCTCCTGATGTTTGAGTAGTAGTCCCTGTAACTGCGCTAACGACAGGTCGAGTTCT
           S  E  D  Y  K  L  I  I  R  D  I  D  A  I  A  V  Q  L  K  R  -

GGCTGCAaGAaGCTAAGGTTCCGATCTTGTGGAGACCTCTTCACGAaGCGGAGGGTCGcT
841    ---------+---------+---------+---------+---------+---------+ 900
       CCGACGTtCTtCGATTCCAAGGCTAGAACACCTCTGGAGAAGTGCTtCGCCTCCCAGCgA
           L  Q  E  A  K  V  P  I  L  W  R  P  L  H  E  A  E  G  R  W  -

GGTTCTGGTGGGGAGCCAAGGGCCCAGAGGCGTGtAAGAAGCTTTGGCGTCTGTTGTTTG
901    ---------+---------+---------+---------+---------+---------+ 960
       CCAAGACCACCCCTCGGTTCCCGGGTCTCCGCACaTTCTTCGAAACCGCAGACAACAAAC
           F  W  G  A  K  G  P  E  A  C  K  K  L  W  R  L  L  F  D  -

ACCGcCTGGTGAACTACCACAAGATCAAcAATTTGATTTGGGTGTGGACTACGACTGACa
961    ---------+---------+---------+---------+---------+---------+
1020
       TGGCgGACCACTTGATGGTGTTCTAGTTgTTAAACTAAACCCACACCTGATGCTGACTGt
           R  L  V  N  Y  H  K  I  N  N  L  I  W  V  W  T  T  T  D  S  -
       - Sequence continued
```

FIG. 9C

```
Continuing sequence - gCCCGGACGCCCTGAAGTGGTATCCGGGTGATGAATACGTTGATATCGTGGGCGCCGATA
1021----------+----------+----------+----------+----------+----------+1080
      cGGGCCTGCGGGACTTCACCATAGGCCCACTACTTATGCAACTATAGCACCCGCGGCTAT
       P  D  A  L  K  W  Y  P  G  D  E  Y  V  D  I  V  G  A  D  I -

TCTATCTGAAGGACAAGGATTATAGCCCaTCGACGGGTATGTTCTACAACATCGTCAAGC
1081----------+----------+----------+----------+----------+----------+1140
      AGATAGACTTCCTGTTCCTAATATCGGGtAGCTGCCCATACAAGATGTTGTAGCAGTTCG
       Y  L  K  D  K  D  Y  S  P  S  T  G  M  F  Y  N  I  V  K  L -

TCTTCGGTGGCAAGAAGTTGGTTGCTCTGACAGAGAATGGCATTATCCCTGACCCgGACC
1141----------+----------+----------+----------+----------+----------+1200
      AGAAGCCACCGTTCTTCAACCAACGAGACTGTCTCTTACCGTAATAGGGACTGGGcCTGG
       F  G  G  K  K  L  V  A  L  T  E  N  G  I  I  P  D  P  D  L -

TGATGAAGGAGCAgAAGGCCTACTGGGTGTGGTTTATGACCTGGAGCGGATTTGAGAACG
1201----------+----------+----------+----------+----------+----------+1260
      ACTACTTCCTCGTcTTCCGGATGACCCACACCAAATACTGGACCTCGCCTAAACTCTTGC
       M  K  E  Q  K  A  Y  W  V  W  F  M  T  W  S  G  F  E  N  D -

ACCCgAACAAGAACGAGATTTCTCATATCAAGAAGGTCTTCAACCACCCaTTTGTGATCA
1261----------+----------+----------+----------+----------+----------+1320
      TGGGcTTGTTCTTGCTCTAAAGAGTATAGTTCTTCCAGAAGTTGGTGGGtAAACACTAGT
       P  N  K  N  E  I  S  H  I  K  K  V  F  N  H  P  F  V  I  T -

A
                                                      f       S
                                                      l       a
                                                      I       l
                                                      I       I
      CGAAGGATGAGCTTCCGAACCTGAAGGTTGAGGAGTAAtagcttaagtcgac    SEQ.ID.NO.31
1321----------+----------+----------+----------+----------+-- 1372
      GCTTCCTACTCGAAGGCTTGGACTTCCAACTCCTCATTatcgaattcagctg    SEQ.ID.NO.32
       K  D  E  L  P  N  L  K  V  E  E  *  *  L  K  S         SEQ.ID.NO.33
```

FIG. 10A

```
Query    15    GAGATCACCATCGAGGCCGAGAACGGCGTCCTCAACGGCACCTACGTCGCTCGCCAGTTT    74
               ||  || || || || || || || || ||  | |||||| ||||| || ||  | || |||
Sbjct    9631  GAAATTACTATTGAAGCAGAAAATGGGGTATTAAACGGAACCTATGTAGCAAGACAATTT    9572

Query    75    CCTGGCTATCAAGGCACTGGCTACGTCGATGGCTTCGACAAAGACGGCGATAGCTGCTCC    134
               ||||| |||||||||||| || || || || |||||||  || || || || ||  ||
Sbjct    9571  CCTGGATATCAAGGCACAGGTATATGTGGATGGATTTGATAAGGATGGAGATTCTTGTAGT    9512

Query    135   GTCACGTTCGAAGTCAAGGAGTCCGGCATGTACGAACTTATCATTGGCTACGCCGCACCT    194
               ||  || || ||||| |||||||| ||  |||||||||| |  || ||||| || |||||
Sbjct    9511  GTAACTTTTGAAGTAAAGGAGTCTGGAATGTACGAATTAATAATTGGATATGCTGCACCC    9452

Query    195   TACGGTTACAAGGAGAACTCCCTGTACGTCAACGGCGAGTTCCAGACCAACGTCAAATTT    254
               ||  || || || ||||| || ||||| || ||  || ||||| ||  || ||||||||
Sbjct    9451  TATGGATATAAGGAAAATTCCCTTTATGTAAATGGAGAATTTCAAACCAATGTCAAATTT    9392

Query    255   CCACAGTCTCAGAAGTTTACTACTGTCTACGCCGGCCTGATTCCTCTCAAGAATGGTAAG    314
               ||  || ||||| |||||||||| ||  ||  ||  || || ||  |||||| | ||| |
Sbjct    9391  CCCCAATCTCAAAAATTTACAACCGTATATGCTGGTTTAATTCCTTTAAAAAATGGAAAA    9332

Query    315   AACACCATCTCCATCGTCAAGTCCTGGGGATGGTTCCTCCTGGACTACTTCAAGATCAAG    374
               || || ||   || || ||  ||||||||||| |||||||| || ||||| || |||||
Sbjct    9331  AATACAATAAGTATAGTAAAAAGCTGGGGATGGTTTCTTCTTGACTACTTTAAAATCAAA    9272

Query    375   AAGGCCGAGATTCCCACCATGAACCCTACCAACAAACTCGTCACACCCAACCCATCCAAG    434
               ||||| ||| ||||| || || ||||||| |||||  | || ||   || || || || 
Sbjct    9271  AAGGCAGAAATTCCTACCATGAATCCTACAAACAAATTAGTAACCCCTAATCCATCAAAA    9212

Query    435   GAGGCCCAGAAGCTCATGGACTACCTCGTCTCTATCTACGGCAAGTACACCCTCTCTGGC    494
               ||||||||  |  ||||||||||  | |   ||| || || ||||| || ||||| || 
Sbjct    9211  GAGGCCCAAAAATTAATGGACTATTTAGTGAGTATATATGGAAAGTATACTCTCTCGGGT    9152

Query    495   CAGATGGGATACAAGGATGCCTTCTGGATCTGGAACATCACCGACAAATTTCCCGCGATT    554
               |||||||||||  |||||||||||||| || ||||| ||  || || ||||||  | | 
Sbjct    9151  CAGATGGGATATAAAGATGCCTTCTGGATTTGGAATATTACTGATAAGTTTCCAGCTATA    9092

Query    555   TGCGGATTCGATATGATGGATTACTCGCCCTCGCGCGTCGAACGTGGCGCCTCCTCCCGA    614
               || || || ||||||||||| |||| || || || |   ||||| || ||  ||  ||
Sbjct    9091  TGTGGTTTTGACATGATGGACTACTCACCTTCAAGGGTTGAAAGAGGAGCATCTTCAAGA    9032

Query    615   GACGTCGAAGACGCCATCGACTGGTGGAACATGGGCGGTATCGTTCAGTTCCAATGGCAC    674
               || || || || || || ||  |||||||| ||| || ||  ||| |||  ||||||||
Sbjct    9031  GATGTGGAAGATGCTATAGATTGGTGGAATATGGGAGGAATAGTTCAATTTCAATGGCAC    8972
```

- Sequence continued -

FIG. 10B

```
Continuation of Sequence

Query   675   TGGAACGCTCCCAAGGGTCTGTATGATACCCCTGGAAAGGAGTGGTGGCGCGGCTTCTAC   734
              ||||| ||||| ||||| || ||||||||| || ||||| || |||||| | ||||| |||
Sbjct   8971  TGGAATGCTCCAAAGGGACTTTATGATACTCCAGGAAAAGAATGGTGGAGAGGCTTTTAC   8912

Query   735   ACTAACGCTACCTCCTTTGACATTGAGTACGCGTTCAACCATCCCGAGTCCGAGGACTAC   794
              ||||| ||||||    ||||| || || || ||||||||| || || || || || |||
Sbjct   8911  ACTAATGCTACCAGTTTTGATATAGAATATGCTTTCAACCACCCTGAATCTGAAGATTAC   8852

Query   795   AAACTCATCATCAGGGACATTGACGCGATTGCTGTCCAGCTCAAGAGGCTGCAAGAAGCT   854
              ||||| || || ||||| || || || ||||| || || | || || || ||||| ||
Sbjct   8851  AAACTTATAATAAGGGATATAGATGCTATTGCAGTACAATTAAAAAGACTTCAAGAGGCA   8792

Query   855   AAGGTTCCGATCTTGTGGAGACCTCTTCACGAAGCGGAGGGTCGCTGGTTCTGGTGGGGA   914
              || || || ||    | ||||||||| | ||||| || || ||| | ||||||||||||
Sbjct   8791  AAAGTCCCCATACTATGGAGACCTTTACACGAGGCAGAAGGTAGATGGTTCTGGTGGGGA   8732

Query   915   GCCAAGGGCCCAGAGGCGTGTAAGAAGCTTTGGCGTCTGTTGTTTGACCGCCTGGTGAAC   974
              || || || || || || ||||| || |||| || ||| ||   ||||| | || || ||
Sbjct   8731  GCAAAAGGTCCTGAAGCTTGTAAAAAACTATGGAGACTACTTTTTGATAGGCTTGTAAAT   8672

Query   975   TACCACAAGATCAACAATTTGATTTGGGTGTGGACTACGACTGACAGCCCGGACGCCCTG   1034
              || || || || || ||| | || ||||| |||||||| || ||   || || || ||
Sbjct   8671  TATCATAAAATAAATAATCTTATATGGGTTTGGACTACTACAGACTCTCCTGATGCTCTC   8612

Query   1035  AAGTGGTATCCGGGTGATGAATACGTTGATATCGTGGGCGCCGATATCTATCTGAAGGAC   1094
              || ||||||||| || |||||||| || |||| || || || ||||| || || || ||
Sbjct   8611  AAATGGTATCCTGGAGATGAATATGTAGATATTGTAGGAGCAGATATATACCTTAAAGAT   8552

Query   1095  AAGGATTATAGCCCATCGACGGGTATGTTCTACAACATCGTCAAGCTCTTCGGTGGCAAG   1154
              || |||||    ||||| ||||| || |||||| ||||| || || || || |||| ||
Sbjct   8551  AAAGATTATTCTCCATCTACAGGAATGTTCTATAACATTGTAAAACTATTTGGTGGGAAA   8492

Query   1155  AAGTTGGTTGCTCTGACAGAGAATGGCATTATCCCTGACCCGGACCTGATGAAGGAGCAG   1214
              ||  | || ||||| ||||| ||||| || || || ||   || || |||||   ||||
Sbjct   8491  AAACTCGTAGCTCTCACAGAAAATGGAATTATTCCAGATCCAGATTTAATGAAAGAGCAA   8432

Query   1215  AAGGCCTACTGGGTGTGGTTTATGACCTGGAGCGGATTTGAGAACGACCCGAACAAGAAC   1274
              || || || ||| ||||| ||||||||||| ||  || ||||| || ||| || || ||
Sbjct   8431  AAAGCTTATTGGGTATGGTTTATGACCTGGTCAGGTTTTGAAAATGATCCAAACAAAAAC   8372

Query   1275  GAGATTTCTCATATCAAGAAGGTCTTCAACCACCCATTTGTGATCACGAAGGATGAGCTT   1334
              || || ||||||||| || || || || ||  || || || || ||||| || |||||
Sbjct   8371  GAAATCTCTCATATTAAAAAGTATTTAATCATCCCTTTGTAATTACAAAAGATGAGCTA   8312

Query   1335  CCGAACCTGAAGGTTGAGGAGTAA  1358    SEQ. ID. NO. 34
              || ||    || ||||| || |||
Sbjct   8311  CCAAATTTGAAAGTTGAAGAATAA  8288    SEQ. ID. NO. 35
```

FIG. 10C

```
1    MAHVEITIEA ENGVLNGTYV ARQFPGYQGT GYVDGFDKDG DSCSVTFEVK ESGMYELIIG
61   YAAPYGYKEN SLYVNGEFQT NVKFPQSQKF TTVYAGLIPL KNGKNTISIV KSWGWFLLDY
121  FKIKKAEIPT MNPTNKLVTP NPSKEAQKLM DYLVSIYGKY TLSGQMGYKD AFWIWNITDK
181  FPAICGFDMM DYSPSRVERG ASSRDVEDAI DWWNMGGIVQ FQWHWNAPKG LYDTPGKEWW
241  RGFYTNATSF DIEYAFNHPE SEDYKLIIRD IDAIAVQLKR LQEAKVPILW RPLHEAEGRW
301  FWWGAKGPEA CKKLWRLLFD RLVNYHKINN LIWVWTTTDS PDALKWYPGD EYVDIVGADI
361  YLKDKDYSPS TGMFYNIVKL FGGKKLVALT ENGIIPDPDL MKEQKAYWVW FMTWSGFEND
421  PNKNEISHIK KVFNHPFVIT KDELPNLKVE E**LKS      SEQ. ID. NO. 36
```

FIG. 21a

```
    N           P       ┌─────────────────────────────────────────┐
    c           m       ¦ Begin Carbohydrate Binding Module 6 (CBM6) ¦
    o           l       └─────────────────────────────────────────┘
    I           I       ┌┄┄┄┄┄┄┄┄┄┄┄┄┄┄┄▶
          ccatggcacacgtg GAGATCACCATCGAGGCCGAgAAcGGCGTCCTCAACGGCACCTACG
    1     ───────────────────────────────────────────────────────────+ 60
          ggtaccgtgtgcac CTCTAGTGGTAGCTCCGGCTcTTgCCGCAGGAGTTGCCGTGGATGC
             m  a  h  v  E  I  T  I  E  A  E  N  G  V  L  N  G  T  Y  V -

TCGCtaagCAGTTtCCTGGCTATCAaGGCACTGGCTACGTCGATGGCTTCGACAAaGACG
   61     ───────────────────────────────────────────────────────────+ 120
          AGCGattcGTCAAaGGACCGATAGTtCCGTGACCGATGCAGCTACCGAAGCTGTTtCTGC
             A  K  Q  F  P  G  Y  Q  G  T  G  Y  V  D  G  F  D  K  D  G -

GCGAtAGCTGCTCCGTCACGTTCGAaGTCAAGGAGTCCGGCATGTACGAaCTTATCATtG
  121     ───────────────────────────────────────────────────────────+ 180
          CGCTaTCGACGAGGCAGTGCAAGCTtCAGTTCCTCAGGCCGTACATGCTtGAATAGTAaC
             D  S  C  S  V  T  F  E  V  K  E  S  G  M  Y  E  L  I  I  G -

GCTACGCCGCaCCTtACGGTTAC AAG GAGAACTCCCTGTACGTCAACGGCGAGTTCCAGA
  181     ───────────────────────────────────────────────────────────+ 240
          CGATGCGGCGtGGAATGCCAATG TTC CTCTTGAGGGACATGCAGTTGCCGCTCAAGGTCT
             Y  A  A  P  Y  G  Y  K   E  N  S  L  Y  V  N  G  E  F  Q  T -

CCAACGTCAAaTTtCCaCAGTCTCAGAAGTTTACTACTGTCTACGCCGGCCTGATtCCTC
  241     ───────────────────────────────────────────────────────────+ 300
          GGTTGCAGTTtAAaGGtGTCAGAGTCTTCAAATGATGACAGATGCGGCCGGACTAaGGAG
             N  V  K  F  P  Q  S  Q  K  F  T  T  V  Y  A  G  L  I  P  L -

TCAAGAATGGtAAgAACACCATCTCCATCGTCAAGTCC TGG GGA TGG TTCCTCCTGGACT
  301     ───────────────────────────────────────────────────────────+ 360
          AGTTCTTACCaTTcTTGTGGTAGAGGTAGCAGTTCAGG ACC CCT ACC AAGGAGGACCTGA
             K  N  G  K  N  T  I  S  I  V  K  S  W   G   W   F  L  L  D  Y -

ACTTCAAGATCAAGAAGGCCGAGATtCCCACCATGAACCCTACCAACAAaCTCGTCACaC
  361     ───────────────────────────────────────────────────────────+ 420
          TGAAGTTCTAGTTCTTCCGGCTCTAaGGGTGGTACTTGGGATGGTTGTTtGAGCAGTGtG
             F  K  I  K  K  A  E  I  P  T  M  N  P  T  N  K  L  V  T  P -
                                         ┌┄┄┄┄┄┄┄┄┄┄┄┄┄┄┄▶
          CCAACCCaTCCAAGGAGGCCCAGAAGCTCATGGACTACCTCGTCTCTATCTACGGCAAGT
  421     ───────────────────────────────────────────────────────────+ 480
┌─────┐   GGTTGGGtAGGTTCCTCCGGGTCTTCGAGTACCTGATGGAGCAGAGATAGATGCCGTTCA
¦Catalytic¦   N  P  S  K  E  A  Q  K  L  M  D  Y  L  V  S  I  Y  G  K  Y -
¦ domain ¦
└─────┘
          ACACCCTCTCTGGCCAGATGGGATACAAGGAtGCCTTCTGGATCTGGAACATCACCGACA
  481     ───────────────────────────────────────────────────────────+ 540
          TGTGGGAGAGACCGGTCTACCCTATGTTCCTaCGGAAGACCTAGACCTTGTAGTGGCTGT
             T  L  S  G  Q  M  G  Y  K  D  A  F  W  I  W  N  I  T  D  K -
```

- Sequence continued -

FIG. 21b

```
     AaTTtCCCGCGATTTGCGGATTCGATATGATGGATTACTCgCCCTCgCGCGTCGAaCGTG
541  ---------+---------+---------+---------+---------+---------+ 600
     TtAAaGGGCGCTAAACGCCTAAGCTATACTACCTAATGAGcGGGAGcGCGCAGCTtGCAC
      F  P  A  I  C  G  F  D  M  M  D  Y  S  P  S  R  V  E  R  G -

GCGCCTCCTCCCGAGACGTCGAaGACGCCATCGACTGGTGGAACATGGGCGGTATCGTTC
601  ---------+---------+---------+---------+---------+---------+ 660
     CGCGGAGGAGGGCTCTGCAGCTtCTGCGGTAGCTGACCACCTTGTACCCGCCATAGCAAG
      A  S  S  R  D  V  E  D  A  I  D  W  W  N  M  G  G  I  V  Q -

AGTTCCAaTGGCACTGGAACGCTCCCAAGGGtCTGTATGAtACCCCTGGAAAGGAGTGGT
661  ---------+---------+---------+---------+---------+---------+ 720
     TCAAGGTtACCGTGACCTTGCGAGGGTTCCCaGACATACTaTGGGGACCTTTCCTCACCA
      F  Q  W  H  W  N  A  P  K  G  L  Y  D  T  P  G  K  E  W  W -

GGCGCGGCTTCTACACTAACGCTACCTCCTTTGACATTGAGTACGCGTTCAACCAtCCCG
721  ---------+---------+---------+---------+---------+---------+ 780
     CCGCGCCGAAGATGTGATTGCGATGGAGGAAACTGTAACTCATGCGCAAGTTGGTaGGGC
      R  G  F  Y  T  N  A  T  S  F  D  I  E  Y  A  F  N  H  P  E -

AGTCCGAGGACTACAAACTCATCATCAGGGACATTGACGCGATTGCTGTCCAGCTCAAGA
781  ---------+---------+---------+---------+---------+---------+ 840
     TCAGGCTCCTGATGTTTGAGTAGTAGTCCCTGTAACTGCGCTAACGACAGGTCGAGTTCT
      S  E  D  Y  K  L  I  I  R  D  I  D  A  I  A  V  Q  L  K  R -

GGCTGCAaGAaGCTAAGGTTCCGATCTTGTGGAGACCTCTTCACGAaGCGGAGGGTCGcT
841  ---------+---------+---------+---------+---------+---------+ 900
     CCGACGTtCTtCGATTCCAAGGCTAGAACACCTCTGGAGAAGTGCTtCGCCTCCCAGCgA
      L  Q  E  A  K  V  P  I  L  W  R  P  L  H  E  A  E  G  R  W -

GGTTCTGGTGGGGAGCCAAGGGCCCAGAGGCGTGtAAGAAGCTTTGGCGTCTGTTGTTTG
901  ---------+---------+---------+---------+---------+---------+ 960
     CCAAGACCACCCCTCGGTTCCCGGGTCTCCGCACaTTCTTCGAAACCGCAGACAACAAAC
      F  W  W  G  A  K  G  P  E  A  C  K  K  L  W  R  L  L  F  D -

ACCGcCTGGTGAACTACCACAAGATCAAcAATTTGATTTGGGTGTGGACTACGACTGACa
961  ---------+---------+---------+---------+---------+---------+ 1020
     TGGCgGACCACTTGATGGTGTTCTAGTTgTTAAACTAAACCCACACCTGATGCTGACTGt
      R  L  V  N  Y  H  K  I  N  N  L  I  W  V  W  T  T  T  D  S - gCCCGGACGCCCTGAAGTGGTATCCGGGTGATGAATACGTTGATATCGTGGGCGCCGATA
1021 ---------+---------+---------+---------+---------+---------+ 1080
     cGGGCCTGCGGGACTTCACCATAGGCCCACTACTTATGCAACTATAGCACCCGCGGCTAT
      P  D  A  L  K  W  Y  P  G  D  E  Y  V  D  I  V  G  A  D  I -

TCTATCTGAAGGACAAGGATTATAGCCCaTCGACGGGTATGTTCTACAACATCGTCAAGC
1081 ---------+---------+---------+---------+---------+---------+ 1140
     AGATAGACTTCCTGTTCCTAATATCGGGtAGCTGCCCATACAAGATGTTGTAGCAGTTCG
      Y  L  K  D  K  D  Y  S  P  S  T  G  M  F  Y  N  I  V  K  L -
```

-Sequence continued-

*FIG. 21c*

```
       TCTTCGGTGGCAAGAAGTTGGTTGCTCTGACAGAGAATGGCATTATCCCTGACCCgGACC
1141   ---------+---------+---------+---------+---------+---------+ 1200
       AGAAGCCACCGTTCTTCAACCAACGAGACTGTCTCTTACCGTAATAGGGACTGGGcCTGG
         F  G  G  K  K  L  V  A  L  T  E  N  G  I  I  P  D  P  D  L -

TGATGAAGGAGCAgAAGGCCTACTGGGTGTGGTTTATGACCTGGAGCGGATTTGAGAACG
1201   ---------+---------+---------+---------+---------+---------+ 1260
       ACTACTTCCTCGTcTTCCGGATGACCCACACCAAATACTGGACCTCGCCTAAACTCTTGC
         M  K  E  Q  K  A  Y  W  V  W  F  M  T  W  S  G  F  E  N  D -

ACCCgAACAAGAACGAGATTTCTCATATCAAGAAGGTCTTCAACCACCCaTTTGTGATCA
1261   ---------+---------+---------+---------+---------+---------+ 1320
       TGGGcTTGTTCTTGCTCTAAAGAGTATAGTTCTTCCAGAAGTTGGTGGGtAAACACTAGT
         P  N  K  N  E  I  S  H  I  K  K  V  F  N  H  P  F  V  I  T -
                                                        A
                                                        f           S
                                                        l           a
                                                        I           l
                                                        I           I
       CGctcGATGAGCTTCCGAACCTGAAGGTTGAGGAGTAAtagcttaagtcgac   SEQ.ID.NO.37
1321   ---------+---------+---------+---------+---------+--- 1372
       GCgagCTACTCGAAGGCTTGGACTTCCAACTCCTCATTatcgaattcagctg   SEQ.ID.NO.38
         L  D  E  L  P  N  L  K  V  E  E  *  *  L  K  S   -  SEQ.ID.NO.39
```

FIG. 25

```
       N           P
       c           m
       o           l       ┌─────────────────────────────────────┐
       I           I       ¦ Carbohydrate Binding Module 6 (CBM6) ¦
                           └─────────────────────────────────────┘
      ccatggcacacgtgGAGATCACCATCGAGGCCGAgAAcGGCGTCCTCAACGGCACCTACG
  1   ----------+----┆-----+----------+----------+----------+----------+  60
      ggtaccgtgtgcacCTCTAGTGGTAGCTCCGGCTcTTgCCGCAGGAGTTGCCGTGGATGC
          m  a  h  v   E  I  T  I  E  A  E  N  G  V  L  N  G  T  Y  V -
                                                                   ▶
      TCGCtaagCAGTTtCCTGGCTATCAaGGCACTGGCTACGTCGATGGCTTCGACAAaGACG
 61   ----------+----------+----------+----------+----------+----------+  120
      AGCGattcGTCAAaGGACCGATAGTtCCGTGACCGATGCAGCTACCGAAGCTGTTtCTGC
       A  K  Q  F  P  G  Y  Q  G  T  G  Y  V  D  G  F  D  K  D  G -

GCGAtAGCTGCTCCGTCACGTTCGAagTCAAGGAGTCCGGCATGTACGAaCTTATCATtG
121   ----------+----------+----------+----------+----------+----------+  180
      CGCTaTCGACGAGGCAGTGCAAGCTtCAGTTCCTCAGGCCGTACATGCTtGAATAGTAaC
       D  S  C  S  V  T  F  E  V  K  E  S  G  M  Y  E  L  I  I  G -

GCTACGCCGCaCCTTACGGTTAC┆cgc┆GAGAACTCCCTGTACGTCAACGGCGAGTTCCAGA
181   ----------+----------+---┆---┆----+----------+----------+----------+  240
      CGATGCGGCGtGGAATGCCAATG┆gcg┆CTCTTGAGGGACATGCAGTTGCCGCTCAAGGTCT
       Y  A  A  P  Y  G  Y   R   E  N  S  L  Y  V  N  G  E  F  Q  T -
                            K→R CCAACGTCAAaTTTCCaCAGTCTCAGAAGTTTACTACTGTCTACGCCGGCCTGATtCCTC
241   ----------+----------+----------+----------+----------+----------+  300
      GGTTGCAGTTtAAaGGtGTCAGAGTCTTCAAATGATGACAGATGCGGCCGGACTAaGGAG
       N  V  K  F  P  Q  S  Q  K  F  T  T  V  Y  A  G  L  I  P  L -
            SEQ.ID.NO.39
      TCAAGAATGGtAAgAACACCATCTCCATCGTCAAGTCC┆ctG┆GGA┆TtG┆TTCCTCCTGGACT
301   ----------+----------+----------+----------+-┆---┆---┆-+----------+  360
      AGTTCTTACCaTTcTTGTGGTAGAGGTAGCAGTTCAGG┆gaC┆CCT┆AaC┆AAGGAGGACCTGA
       K  N  G  K  N  T  I  S  I  V  K  S   L   G   L   F  L  L  D  Y -
                                            W→L     W→L ACTTCAAGATCAAGAAGGCCGAGATtCCCACCATGAACCCTACCAACAAaCTCGTCACaC  SEQ.ID.40
361   ----------+----------+----------+----------+----------+----------+  420
      TGAAGTTCTAGTTCTTCCGGCTCTAaGGGTGGTACTTGGGATGGTTGTTtGAGCAGTGtG  SEQ.ID.41
       F  K  I  K  K  A  E  I  P  T  M  N  P  T  N  K  L  V  T  P  SEQ.ID.42
```

GLYCOSYL HYDROLASE ENZYMES IN HIGH TEMPERATURE INDUSTRIAL PROCESSES

CROSS REFERENCE TO RELATED APPLICATIONS

This application claims priority based on U.S. Provisional Application Ser. No. 61/909,012 filed Nov. 26, 2013, which is incorporated herein by reference.

FIELD OF THE INVENTION

Glycosyl hydrolases effective in degrading beta-1,4-linkages in polymers including guar and derivitized guar in high temperature industrial processes.

BACKGROUND

Hydrocarbons (oil, natural gas, etc.) are obtained from subterranean geologic formations by drilling a well that penetrates the hydrocarbon-bearing formation and seeks to release hydrocarbons trapped in the formation thus allowing them to reach the surface. In order for the hydrocarbon to be "produced", the hydrocarbon must be able to travel from the formation to the wellbore (and ultimately to the surface) at a reasonably economic rate. Thus, there must be a sufficiently unimpeded flowpath from the formation to the wellbore. Hydraulic fracturing ("fracing") is a primary tool for improving well productivity by placing or extending channels within the formation. This operation is essentially performed by hydraulically injecting a fracturing fluid into a wellbore penetrating a subterranean formation and forcing the fracturing fluid against the formation strata by extreme pressure thus inducing cracks or fractures in the formation.

Because the fractures would otherwise close upon release of the frac pressure due to the overburden weight, the cracks or fractures are held open by crush resistant "proppants" such as sand or ceramics included in the fracturing fluid. However, in delivering the proppants, which will fall out of solution if not suspended, fracturing fluids including proppants typically include viscosifying agents. Fracturing fluids are customized to the formations being fractured and, depending on the formation requirements, can be extremely viscous gel-like solutions or may be less viscous such as with foam or high flow-rate "slickwater" fracturing. Slickwater fracturing fluids are typically low viscosity, low proppant solutions pumped at very high rates.

Ideal fracturing fluids should be sufficiently viscous to create a fracture of adequate width, provide for maximal fluid travel distance to extend fracture length, be able to transport desired proppant amounts into the fracture, and require minimal gelling agent to allow for easier degradation or "breaking" at reasonable cost. The frac fluid will typically contain a number of other fluid additives in addition to the proppants in order to provide for formation clean up, foam stabilization, leakoff inhibition, and/or surface tension reduction. These additives include biocides, fluid-loss agents, enzyme breakers, acid breakers, oxidizing breakers, friction reducers, and surfactants such as emulsifiers and non-emulsifiers.

Natural gelling agents used in fracturing operations have included natural guar and locust bean gum, xanthan gum, starch and cellulose. Among the most commonly used polymers for fracturing are the high-molecular weight polysaccharides isolated from guar gums and derivatives thereof including hydroxypropyl guar (HPG), carboxymethylhydroxypropyl guar (CMHPG) and carboxymethyl guar (CMG), hydrophobically modified guars, and guar-containing compounds. In addition to being highly viscous, the high-molecular weight guar based polysaccharides are essentially non-toxic. Guar, and derivatives thereof, are used both as viscosifying agents in frac fluids and as fluid loss control additives with low solid drilling muds.

After a fracturing fluid is formed and pumped into a subterranean formation and the proppant has been properly delivered into the fractures formed, it is generally desirable to convert the highly viscous fracturing fluid to a lower viscosity fluid that will not plug the formation. Residual unbroken polymers and filtercake can severely reduce permeability and conductivity in the fractured formation. The induced reduction in viscosity of the treating fluid is commonly referred to as "breaking." Consequently, the materials used to break the viscosity of the fluid are referred to as breaking agents or "breakers." Once broken, the polymer material flows easily out of the formation and desired material, such as oil or gas, is allowed to flow into the well bore. For purposes of breaking guar and guar based polymer gels, typically either oxidative, acid or enzyme breakers are used, each of which are directed to breaking connective linkages that form the highly viscous polymer chains.

Oxidative breakers generate free radicals that are able to attack the guar repeating unit at multiple sites and break the polymer chain. Typical oxidizers include persulfate ($S_2O^{2-}$) salts of ammonium, sodium and potassium, which decompose at elevated temperatures downhole to form free radicals that effect the breaking of the polymer chains. Because the breaking occurs rapidly at temperatures over 140° F., the use of the oxidizers must be carefully controlled to avoid breaking the gelling agents prior to proppant delivery. To avoid premature breaking, oxidizers are sometimes encapsulated. Acids such as hydrochloric acid are sometimes used as breakers. Both oxidizing and acid breakers can be corrosive, adversely reactive with both equipment and compounds used downhole, and can contaminate the produced oil and gas sufficiently to affect downstream catalytic processes.

Enzymatic breakers are particularly desirable as "green" non-toxic and biodegradable fracturing fluid additives. For breaking polymeric guar and derivatives thereof, endomannanases that catalyse the hydrolysis of 1,4-β-D-mannosidic linkages in mannans, galactomannans, and glucomannans may have applications in the aforementioned processes. Enzymes have been used for over 40 years as breakers but until relatively recently enzymatic breakers were not available that functioned optimally at the required pH and temperature conditions.

Taken together it is apparent that a frac fluid is a complex mixture that requires both adequate initial viscosity and the ability to be sufficiently broken after proppant deposition or placement. The present inventors appreciated that what are needed for a range of industrial applications are improved enzymes that are stable but less active under mixing conditions but are able to provide robust degradation of beta-1,4-linkages in viscous polymers under working conditions.

SUMMARY

Provided herein are recombinant thermophilic *Dictyoglomus* beta-mannanases in liquid and dry form that are particularly adapted for breaking guar polymers in high temperature environments. In certain embodiments the Dictyoglomus is a Dictyoglomus thermophilum, while in other embodiments the Dictyoglomus is a Dictyoglomus turgidum.

In certain embodiments the recombinant thermophilic Dictyoglomus beta-mannanases are expressed from codon optimized expression cassettes where the mannanase sequence is enginerred to the preferred codon usage in the desired expression host. Exemplary expression sequences for expression in E. coli and T. reesei are provided herein.

In one embodiment, an expression cassette for high level expression of a nucleic acid sequence encoding a Dictyoglomus beta-mannanase in an exogenous host is provided, wherein expression cassette includes a secretion signal that drives extracellular secretion of the enzyme from the exogenous host and the nucleic acid sequence is codon optimized for expression in the exogenous host. In one such embodiment the Dictyoglomus beta-mannanase is produced by extracellular secretion in T. reesei. Surprisingly, the mannanase produced in T. reesei was considerably more stable than that produced in E. coli.

In certain embodiments, mutants were generated wherein a CBM domain of the beta-mannanase was mutated to reduce or abolish mannan binding by amino acid substitution at one or more key residues for mannan binding. Such key residues included those selected from the group consisting of one or more of: lysine residue at 68 on SEQ. ID. NO. 42; tryptophan residue at 113 on SEQ. ID. NO. 42; and tryptophan residue at 115 on SEQ. ID. NO. 42. Reductions in mannose binding, whether by mutation in the CBM domain, by deletion of some or all of the CBM domain, or by truncation resulting in loss of some or all of the CBM domain resulted in higher activity in the hydrolysis of mannan albeit with some loss of temperature stability.

Thus, guar enzyme breakers are provided having a mixture of stable full length mannanase and high activity mutated, deleted or truncated mannanase, wherein the mixture allows for tailoring the breaking process to a particular frac job. Thus, by virtue of a mixture of rapid breaking mutated, deleted or truncated mannanase together with high temperature stable full length mannanase, a two-phase breakage is provided to maximize utility during a fracturing process. At ambient temperature when the frac fluid is made up-hole neither the truncated or the full-length DtManA will be active and the cross-linked guar will provide maximum integrity and ability to suspend proppants. No degradation of the guar is desired until the proppant is delivered into the fractured formation. As the frac fluid is heated by the downhole formation the enzymes become active. In one embodiment, the mutated or truncated form of DtManA that lacks a native DtManA CBM domain is included because this form acts very fast and provides a level of early breaking such that the pumping can be continued with less friction pressure and excessive pressure build up. Ultimately, because it is less stable and has a shorter half-life, the mutated or truncated form of DtManA that lacks a native DtManA CBM domain is denatured and ceases to function. However, the full-length form will remain active and will continue breaking the cross-linked guar at temperatures up to 275° F. for prolonged periods. Thus, an improved guar breaker is provided that includes a mixture of Dictyoglomus beta-mannanases including proportion of a full-length DtManA and a proportion of a truncated or mutated DtManA that lacks a native DTManA CBM domain and has a higher catalytic activity level. In one such embodiment, the mixture of Dictyoglomus beta-mannanases are produced in T. reesei.

Also provided are methods of generating commercial quantities of an enzyme breaker for guar based polymer gels that comprise beta-(1,4) mannosidic linkages. The method includes transforming a population of exogenous host cells with an expression cassette including a nucleic acid sequence encoding a hyperthermophilic Dictyoglomus beta-mannanase; culturing the transformed exogenous host cells in batch, fed batch or continuous fermentation; preparing a cell free supernatant containing the Dictyoglomus beta-mannanase from the fermentation; and partially purifying the Dictyoglomus beta-mannanase from the cell free supernatant by heat treatment at 70° C. or higher and removal of heat denatured proteins, wherein the partially purified Dictyoglomus beta-mannanase is provided as an enzyme breaker additive to a guar based polymer gel for downhole fracking in high temperature applications.

Storage stable dry powder guar breakers are also provided that include at least one beta-mannanase derived from a thermophilic bacteria such as Dictyoglomus thermophilum or Dictyoglomus turgidum and having activity at temperatures over 130° F., wherein the dry powder is rehydrated in a frac fluid for use as a guar breaker.

In certain embodiments, the disclosed enzymes are added in liquid or dry form directly to the frac fluid, or combined with any other additive they are compatible with i.e. guar, clay stabilizers, buffer, surfactants, crosslinkers, solvent etc. These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 1 illustrates the aligned sequences of a Dictyoglomus thermophilum endomannanase according to one embodiment and identified as SEQ. ID. NO. 1 compared with a Dictyoglomus turbidum endomannanase according to one embodiment and identified as SEQ. ID. NO. 2.

FIG. 2 illustrates an exemplary amino acid sequence of a catalytic domain of a Dictyoglomus thermophilum endomannanase according to one embodiment and identified as SEQ. ID. NO. 3.

FIG. 3 illustrates an exemplary amino acid sequence of an N-terminal sequence with respect to the catalytic domain for conferring thermostability thereon according to the disclosure and identified as SEQ. ID. NO. 21.

FIG. 4A illustrates an exemplary amino acid sequence of a recombinant endomannanase peptide according to one embodiment and identified as SEQ. ID. NO. 24. FIG. 4B compares the sequence of FIG. 4A with the reference wild type sequence of SEG. ID. NO. 1.

FIG. 5 illustrates an exemplary nucleotide sequence of an endomannanase catalytic domain according to one embodiment and identified as SEQ. ID. NO. 26.

FIG. 6 illustrates an exemplary nucleotide sequence of a recombinant endomannanase peptide according to one embodiment and identified as SEQ. ID. NO. 27.

FIG. 7A-B show the nucleotide sequence of a recombinant endomannanase peptide codon optimized for expression in E. coli and identified as SEQ. ID. NO. 28. The codon optimized gene is compared with a wild type gene identified as SEQ. ID. NO. 29.

FIG. 7C depicts the translated amino acid sequence (SEQ. ID. NO. 30) of the nucleic acid of SEQ. ID. NO. 28.

FIGS. 8A and 8B depict schematics for certain exemplary T. reesei expression cassettes.

FIGS. 9A-C show a gene encoding a *Dictyoglomus thermophilum* endomannanase according to one embodiment that is codon optimized for expression in T. reesei.

FIGS. 10A-B show an alignment of gene encoding a *Dictyoglomus thermophilum* endomannanase codon optimized for expression in T. reesei with a wild type gene.

FIG. 10C shows the translated amino acid sequence (SEQ. ID. NO. 36) of the nucleic acid encoded by the nucleic acid sequence of SEQ. ID. NO. 34.

FIGS. 21A-C show a gene encoding a *Dictyoglomus thermophilum* endomannanase according to another embodiment that is codon optimized for expression in T. reesei in which the R of the RQ site is changed to K (position 66) and the K of the KDEL site is changes to L.

FIG. 25 depicts the locations of three mutations in the CBM domain that reduce mannan binding and increase mannanase activity.

DETAILED DESCRIPTION

Figure 11:
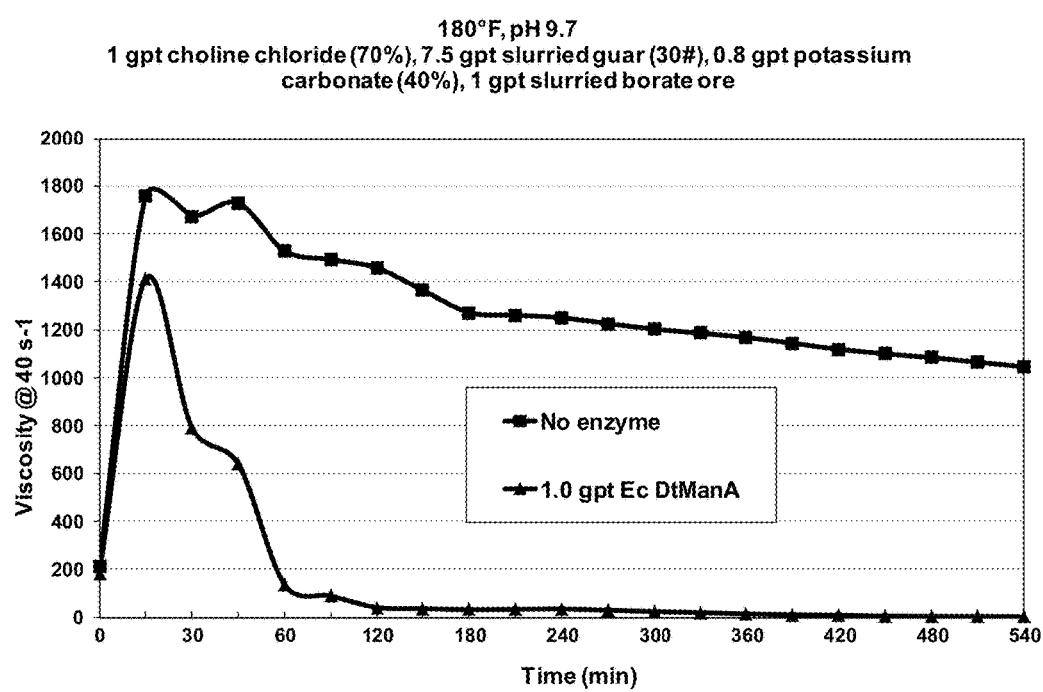
FIG. 11 is a data graph that illustrates the viscosity degradation in a 30 ppt borate crosslinked guar polymer at 180° F. and pH 9.7, showing rheology curves with and without the enzyme, showing the effectiveness of an amino terminal truncated recombinant *D. thermophilum* mannase enzyme expressed from a codon optimized gene in *E. coli*. (Ec DtManA).

Through their experience in the industry, the present inventors appreciated that currently available enzyme breakers for degrading beta-1,4-linkaged polymers such as guar and derivatized guars in fracturing methods as well as other industrial applications tend to be ineffective due to being denatured, inactive, or inhibited at high temperature and high alkalinity, or overly active at surface ambient temperatures. Due to the activity of currently available breaking enzymes at surface ambient temperatures, the present inventors further appreciated that the currently available endomannanases begin breaking guar polymers immediately upon addition such that maximum viscosity is short lived. If the frac job is delayed for any reason, frac fluid containing presently available enzyme breakers may need to be discarded because it will lack the viscosity needed to suspend the proppants throughout the pumping process. The present inventors appreciated the need for, and then developed, enzymes for a range of industrial applications that are stable but less active under mixing conditions at ambient temperatures and are able to provide robust degradation of beta-1,4-linkages in viscous polysaccharide gellants under conditions of high temperatures through a range of pH. Provided herein are recombinant enzyme breakers produced from genes derived from thermophilic *Dictyoglomus* bacteria that are stable but relatively slowly reactive at the high pH and surface ambient temperatures at which frac fluids are mixed up-hole. However, under down-hole conditions of high temperature and a falling pH that is buffered toward neutrality by the formation, the *Dictyoglomus* enzymes provided herein are maximally active and rapidly and virtually completely break polysaccharide gellants to avoid any plugging of the flow of hydrocarbons from the formation.

The *Dictyoglomus* enzymes provided herein disclosure are suitable for any field of hydrolytic enzymes functioning at high pH and more specifically, to industrial applications for recombinant glycosyl hydrolases including in oil and gas production. In certain embodiments, the enzymes disclosed herein are applied in hydraulic fracturing operations for oil and gas production but also for procedures that utilize guar or derivatized guar polymers at elevated temperatures including without limitation in completion, drilling, workover, remedial treatments, and pipeline cleaning.

In still other embodiments, the enzymes provided herein are utilized for stimulation of groundwater wells, enhanced geothermal system development and waste disposal. Other industrial applications for the hydrolytic enzymes disclosed herein may be found in paper making for bleaching of softwood pulps, coffee processing to improve enzymatic degradation of beans, livestock feed for improved nutritional extraction from feedstuffs, and cleaning aids for degradation of stains. Many of the aforementioned applications also require enzymes that are thermostable, or capable of enzymatic activity at temperatures that are higher than standard ambient temperature of 25° C. (77° F.), as they incorporate processes and utilize temperatures in excess of about 65° C. (149° F.). Also, some of the aforementioned applications utilize highly alkaline conditions, and thus require alkaline stability at or above about pH 10. Conventionally, hydrolytic enzymes are denatured, inactive, or inhibited at high temperature and high alkalinity, thereby eliminating or reducing their effectiveness. Further, hydrolysis may represent only one step of the process and in certain applications, the enzyme may be only one of several enzymes utilized.

Constituents of Fracturing Fluids

Frac fluids are complex mixtures that are generally water based fluids including proppants and either a gelling agent or a foam to suspend the proppant. Additionally, the fracturing fluid may contain other components as deemed necessary to fulfill user and/process goals. Typical further additives to water-based fracturing fluids include buffers, crosslinkers or gel stabilizers, clay stabilizers, friction reducers, surfactants, biocides, corrosion inhibitors, scale reducers and combinations thereof.

"Propping agents" or "proppants" are insoluble particulates, which are suspended in the fracturing fluid and carried downhole, and deposited in the fracture. When deposited in the fracture, the proppant forms a "proppant pack", and, while holding the fracture apart, provides conductive channels through which fluids can flow to the wellbore. Proppants are typically added to the fracturing fluid just prior to the addition of the crosslinking agent although addition of the proppants at any suitable time is contemplated. Propping agents include, but are not limited to, quartz sand grains, crystalline silica (silicon dioxide), glass and ceramic beads, bauxite grains, aluminum pellets, nylon pellets, and the like. The propping agents are normally used in concentrations between about 1 to 14 pounds per gallon of fracturing fluid composition, but higher or lower concentrations can be used as required by the fracture program or design.

The gelling agents relevant to the present invention are polysaccharides that include beta-1,4-mannosidic linkages such as substituted galactomannans, guar gums, high-molecular weight polysaccharides composed of mannose and galactose sugars, or guar derivatives such as cationic guar derivatives such as guar hydroxypropyltrimonium chloride and hydroxypropyl guar (HPG), carboxymethylhydroxypropyl guar (CMHPG), and carboxymethyl guar (CMG), hydrophobically modified guars, guar-containing compounds, and synthetic polymers including beta-1,4-mannosidic linkages. The basic guar polysaccharide, isolated from the endosperm of guar beans (*Cyamopsis tetragonoloba*), is a long chain galactomannan having a backbone of mannose moieties connected by β-1,4 acetal linkages. Galactose units may be attached to the backbone by α-1,6 acetal linkages at essentially every second mannose or may be attached in pairs but in either event result in a ratio of approximately 1.5:1 to 2:1 of mannose to galactose. Both mannose and galactose have the same molecular formula ($C_6H_{12}O_6$) and molar mass of 180.156 g mol$^{-1}$ and thousands of repeating units of mannose and galactose form a linear polysaccharide having a molecular weight from 200 to 2,000 kDa with an average number of repeating units of over 3,700 (H. D. Brannon, R. M. Tjon-Joe-Pin, "Biotechnological breakthrough improves performance of moderate to high-temperature fracturing applications," SPE 28513, 1994). The gelling agents are typically supplied as a guar polymer slurry and are further diluted and hydrated at the job site to form a so called linear gel.

To increase overall viscosity and to prevent thermal thinning of guar based gelling agents downhole, the gel polymers are typically crosslinked. Crosslinking agents based on boron, titanium, zirconium or aluminum complexes are typically used to increase the effective molecular weight of the polymer and make them better suited for use in high-temperature wells. Suitable borate crosslinkers include organoborates, monoborates, polyborates, mineral borates, boric acid, sodium borate, including anhydrous or any hydrate, borate ores such as colemanite or ulexite. Fracturing fluids may include low or high pH buffers/adjusters depending on the crosslinker used and the pH that most effectively supports ion exchange between the guar polymer and the metal ion crosslinker Borate ions require a pH over 8.0, while aluminum requires low pH. In contrast, titanium will crosslink guar, HPG or CMHPG in a broad range from pH 9 to pH 3. Likewise, depending on associated ligands, zirconium can crosslink at high or low pH. In certain examples of the present disclosure, borate and zirconium crosslinking agents are utilized. The crosslinking agent is preferably present in the range from about 0.001% to in excess of 0.5% by weight of the aqueous fluid. Preferably, the concentration of crosslinking agent is in the range from about 0.005% to about 0.25% by weight of the aqueous fluid.

The endomannanases used in the oil and gas industry that hydrolyze 1,4-β-D-mannosidic linkages of guar and guar derivatives have been variously referred to as endo-1,4-β-mannanase, endo-β-1,4-mannanase, β-mannanase B, β-1,4-mannan 4-mannohydrolase, endomannanase, endo-β-mannanase, β-D-mannanase, mannan endo-1,4-β-mannosidase, or 1,4-β-D-mannan mannanohydrolase and any of these terms may be used interchangeably. The enzyme is preferably present in the range of 0.001% to in excess of 0.5% by weight of the aqueous fracturing fluid depending on the enzyme unit concentration in light of the guar type and concentration, degree of crosslinking, pH, expected downhole temperature, and the desired breaking timeframe and endpoint for the particular frac job.

Clay stabilizers are designed to temporarily or permanently inhibit clays from swelling in the formation. For example, temporary clay stabilizers used in the industry are salts like potassium, ammonium or choline chloride. Permanent clay stabilizers are typically higher molecular weight amines and cationic polymers. They can be run in combination with temporary clay stabilizers. Surfactants are typically added to reduce the surface tension in order to enhance fluid recovery or prevent formation of emulsions between the frac water and formation fluids, which could damage permeability. Scale inhibitors are designed to inhibit the formation of scale that may cause blockages not only in the equipment used during the particular wellbore servicing operation, but scale can also create fines that block the pores of the formation.

Dictyoglomus Endomannanases

In one embodiment, a *D. thermophilum* endomannanase for use as described herein is capable of cleaving sufficient beta-1,4-linkages in a highly substituted mannan polymer such as guar gum or locust bean gum to render the polymer in a broken state without prior digestion by another hydrolase.

In one embodiment an endomannanase enzyme is provided that was encoded by a gene from the chromosome of the extremely thermophilic bacterium *Dictyoglomus thermophilum* (*D. thermophilum*). *D. thermophilum* was first disclosed by Saiki et al. "*Dictyoglomus thermophilum* gen. nov., sp. nov., a chemoorganotrophic, anaerobic, thermophilic bacterium" Int J Syst Bacteriol 35 (1985) 253-259. The type strain, *Dictyoglomus thermophilum* H-6-12, identified in at least one public repository as ATCC 35947, was reportedly isolated from the slightly alkaline Tsuetae Hot spring in Kumamoto Prefecture in Japan. Likewise, another strain of Dictyloglomus (Rt46B.1) was isolated from a New Zealand hot pool (Patel, B. K., et al. Isolation of an extremely thermophilic chemoorganotrophic anaerobe similar to *Dictyoglomus thermophilum* from a New Zealand hot spring. Arch. Microbiol. 147 (1987) 21-24). Based on a comparison of 16S sequence and known gene sequences, this strain is closely related to the type strain of *D. thermophilum* as disclosed in Gibbs et al, "Appl Environ Microbiol" 61 (1995) 4403-4408, the disclosures of which are incorporated herein for all purposes.

Identification of the gene encoding the *D. thermophilum* mannan endo-1,4-beta-mannosidase was described in Gibbs, et al. "Cloning, Sequencing and Expression of a b-Mannanase Gene from the Extreme Thermophile *Dictyoglomus thermophilum* Rt46B.1, and Characteristics of the Recombinant Enzyme" Current Microbiology 39 (1999) 351-357, and herein incorporated by reference.

The full *D. thermophilum* mannan endo-1,4-beta-mannosidase is a 469 amino acid (aa) protein encoded by a 1410 base pair (bp) gene located between nucleotides 8288 and 9697 of the *D. thermophilum* genome. The reference aa sequence for the complete *D. thermophilum* mannosidase can be found under NCBI accession YP_002249896. This sequence is depicted in FIG. 1 as SEQ. ID. NO. 1. Of this full length sequence, a signal sequence motif can be identified on the amino terminus (shown in part), the region from approximately aa 24-141 is identified as a Carbohydrate Binding Module 6 (CBM6) mannanase-like domain, while the region from aa 156-461 is identified as a member of the glycosyl hydrolase family 26 as shown in FIG. 1.

Based on the amino acid sequence (SEQ ID NO. 1), the full-length ManA molecule (51.9 kDa) is comprised of an n-terminal carbohydrate binding domain (CBD) of 14.0 kDa plus a spacer region of 0.8 kDa followed by a catalytic domain of 37.1 kDa. Apparent peptide band sizes imaged by SDS-PAGE analysis differ slightly from these "theoretical molecular weights" due to possible glycosylation (and amount of glycosylation depending on the expression host) and/or the specific site(s) of proteolytic cleavage. Therefore, the "apparent molecular weights" of the peptides observed by SDS-PAGE image analysis are 52 kDa (full length protein), 37 kDa (catalytic subunit) and 14 kDa (carbohydrate binding domain).

In another embodiment, the endo-1,4-beta-mannosidase gene is isolated from *Dictyoglomus turgidus* (*D. turgidus*), a bacterium that was first described by Svetlichny & Svetlichnaya "*Dictyoglomus turgidus* sp. nov., a new extremely thermophilic *eubacterium* isolated from hot springs of the Uzon volcano caldera" Mikrobiologiya 57 (1988) 435-441. *D. turgidus* is identified in at least one public repository as DSM 6724.

*D. turgidus* also encodes a 469 amino acid (aa) endo-1,4-beta-mannosidase. The provisional reference aa sequence for the complete *D. turgidus* mannosidase can be found under NCBI accession YP_002352217. This sequence is depicted in FIG. 1 as SEQ. ID. NO. 2. Of this full length sequence, the region from aa 1-21 is identified as a signal peptide (shown in part), the region from aa 24-141 is identified as a CBM6 mannanase-like, while the region from aa 156-461 is identified as a member of the glycosyl hydrolase family 26.

*D. thermophilum* and *D. turgidus* share considerable homology in their respective endo-1,4-beta-mannosidases. As shown in FIG. 1, the two 1,4-beta-mannosidase aa sequences have an overall sequence identity of 94% but the alignment positive score (considering conservative substitutions indicated by + symbols between the aligned sequences shown in FIG. 1) by BLASTP is 97%. The two sequences share 88% overall sequence identity and 94% positivity (including conservative substitutions) in their CBM6 mannanase-like domains and 97% overall sequence identity and 98% positivity (including conservative substitutions) in their glycosyl hydrolase family 26 domains.

Dictyoglomus Domain Configurations

In one embodiment a recombinant endomannanase is provided that includes a catalytic domain having between about 280 and about 340 amino acid residues, alternatively between about 290 and about 330 residues, and in certain exemplary configurations the catalytic domain of the disclosed recombinant endomannanase peptide comprises about 320 residues. An exemplary catalytic domain has a sequence shown as SEQ. ID. NO. 3 of FIG. 2.

In one configuration of a recombinant endomannanase peptide provided herein, the catalytic domain polypeptide sequence comprises at least at least 6 polypeptide amino acid sequences, hereinafter referred to as amino-sequence or "AS". Generally, the catalytic domain of this embodiment is configured sequentially according to catalytic domain polypeptide sequence (1):

```
AS1 - AS2 - AS3 - AS4 - AS5 - AS6    (1)
wherein AS1 comprises the sequence:
                                    (SEQ. ID. NO. 4)
YTLSGQMGYK;

AS2 comprises the sequence:
                                    (SEQ. ID. NO. 5)
KFPAICGFDM;

AS3 comprises the sequence:
                                    (SEQ. ID. NO. 6)
GGIVQFQWHW;

AS4 comprises the sequence:
                                    (SEQ. ID. NO. 7)
PLHEAEGRWF;

AS5 comprises the sequence:
                                    (SEQ. ID. NO. 8)
KLVALTENGI;
and AS6 comprises the sequence:
                                    (SEQ. ID. NO. 9)
NKNEISHIKK.
```

The locations of regions AS 1-6 on the endomannanase amino acid sequences of *D. thermophilum* and *D. turgidus* are shown boxed on FIG. 1. As can been seen on FIG. 1, there is complete identity in regions AS 1-6 between *D. thermophilum* and *D. turgidus*.

In certain embodiments, certain amino acid residues of the sequences of AS1, AS2, AS3, AS4, AS5 and AS6 are modified or altered without substantially affecting the endomannanase activity of the catalytic domain. Exemplary modifications of the amino-sequences include, but are not limited to, the additions, substitutions, and deletions described herein below. Further, the exemplary modifications to the amino-sequences may be present in all of, a portion of, or none of the disclosed amino-sequence positions. For example, in AS1 the position 3 amino acid may be leucine (L), asparagine (N), or methionine (M), position 5 may be glycine (G) or valine (V), and position 8 may be glycine (G), aspartate (D), or histidine (H). Likewise, the modifications in position 2 of AS2 comprise phenylalanine (F), serine (S), or asparagine (N), position 3 may be proline (P) or alanine (A), position 5 may be isoleucine (I) or valine (V), position 6 may be cysteine (C), tyrosine (Y), or phenylalanine (F), and position 9 may be aspartate (N) or glutamate (E). Also, position 3 of AS3 may be isoleucine (I) or valine (V), position 5 may be glutamine (E) or threonine (T), and position 8 may be tryptophan (W), leucine (L), alanine (A), or serine (S). Further, AS4 at position 1 may be proline (P) or leucine (L), and position 2 may be leucine (L), tryptophan (W) or tyrosine (Y). Likewise in AS5, modifications of position 4 may be alanine (A) or valine (V), position 5 may be leucine (L), phenylalanine (F), or isoleucine (I), position 6 may be modifications between threonine (T) or serine (S), and position 10 may be substituted between isoleucine (I), proline (P), asparagine (N), or valine (V). Additionally, in AS6 the position 1 may be either asparagine (A) or glycine (G).

In another exemplary configuration of a recombinant endomannanase peptide, there are certain amino acid residues within the amino-sequences that are highly conserved, invariant, or otherwise unable to be added, substituted, or deleted. In certain instances, altering the aforementioned resides reduces, deletes, or otherwise affects the endomannanase activity of the catalytic domain. Accordingly, invariant residues within the amino-sequences include, but are not limited to those described herein. For example, the glutamate (E) residues at position 4 of AS4 and position 7 of AS5 may be considered invariant.

The aforementioned conserved residues and the modifications to the AS do not substantially modify the conformation of the catalytic domain so folding configurations formed by AS1, AS2, AS3, AS4, AS5 and AS6 are retained. More specifically, when provided in a conformation in which the catalytic domain has endomannanase activity, the sequences according to AS1, AS2, AS3, AS4 and AS5 may each form a beta sheet, hereinafter β-sheet, in said recombinant peptide. For example, AS1 may form beta sheet 1, AS2 may form beta sheet 2, AS3 may form beta sheet 3 and AS4 may form beta sheet 4. AS5 may form beta sheet 7, in which case intervening sequences between AS4 and AS5, described hereinafter below, may form beta sheets 5 and 6, respectively. The sequence according to AS6 may form an alpha helix, hereinafter α-helix.

In another exemplary configuration of a recombinant endomannanase peptide, there are connecting or linker amino sequences, hereinafter LAS, that extend between and couple each of the AS described hereinabove. Generally, each LAS retains a conserved folding pattern, for example an α-helix or a β-sheet and does not disrupt or affect the endomannanase catalytic activity.

For example, the recombinant peptide of the present disclosure comprises LAS 1 between AS1 and AS2 comprising between about 10 and about 20 amino acid residues. A portion of the sequence may form an alpha helix, herein alpha 1, and in certain configurations alpha 1 comprises the sequence DAFWIWNITD (SEQ. ID. NO. 10). Also, LAS 2 comprises the amino acid sequence between AS2 and AS3. LAS 2 comprises between about 25 and about 35 residues and a portion thereof may form an alpha helix, herein alpha 2. Alpha 2 comprises the sequence DVEDAIDWWNM (SEQ. ID. NO. 11). The recombinant peptide comprises LAS 3 between AS3 and AS4 and includes between about 60 and about 70 residues. A portion of LAS 3 may form an alpha helix, herein alpha 3, and in certain configurations of the recombinant peptide, alpha 3 has the sequence SEDYKLIIRDIDAIAVQ (SEQ. ID. NO. 12).

Further, the recombinant peptide of the present disclosure comprises LAS 4. LAS 4 comprises intervening amino acid sequences between AS4 and AS5. LAS 4 comprises between about 70 to about 90 residues and a plurality of protein folding moieties. In configurations, LAS 4 comprises at least one β-sheet. In certain configurations, LAS 4 comprises at least two β-sheets, such that a first portion of LAS 4 has the amino acid sequence NNLIWVW (SEQ. ID. NO. 13) thereby forming beta sheet 5. Similarly, a second portion of LAS has the amino acid sequence IVGADIYL (SEQ. ID. NO. 14), thereby forming beta sheet 6 as mentioned previously. Also, in certain configurations, the recombinant peptide sequence of LAS 4 comprises between about 20 to about 30 residues between β-sheets of AS4 and AS5. A portion of the LAS 4 sequence may form an alpha helix, herein alpha 4, comprising the amino acid sequence ACKKLWRLLFDRL (SEQ. ID. NO. 15). Still further, the LAS 4 comprises between about 15 to about 20 residues extending between beta sheets 5 and 6. A portion of the LAS 4 sequence may form an alpha helix, herein alpha 5, between the beta sheets 5 and 6 comprising the amino acid sequence DALKWY (SEQ. ID. NO. 16). Still further, LAS 4 comprises between about 20 to 30 residues extending between beta sheets 6 and 7, the latter comprising the sequence of AS5. A portion of this of LAS 4 sequence may form an alpha helix, herein alpha 6, comprising the amino-acid sequence STGMFYNIVKLF (SEQ. ID. NO. 17).

In certain configurations, the recombinant peptide comprises LAS 5 extending between AS5 and AS6. Generally, LAS 5 comprises between about 25 to about 30 residues, wherein at least a portion of LAS 5 forms a beta sheet, herein beta sheet 8, comprising the amino acid sequence WVWFMTW (SEQ. ID. NO. 18). In further configurations, LAS 5 comprises an alpha helix, herein alpha 7, extending between beta sheets 7 and 8 comprising the amino acid sequence DLMKEQK (SEQ. ID. NO. 19). Still further, in certain embodiments the recombinant peptide comprises LAS 0. LAS 0 comprises between about 20 to about 30 residues located N-terminal of the beta sheet 1 formed by AS 1. A portion of the LAS 0 may form an alpha helix, herein alpha 0, comprising the amino acid sequence KEAQKLMD (SEQ. ID. NO. 20).

The catalytic domain having the sequences as configured according to the disclosure hereinabove retains a secondary and tertiary structure that approximates those found in an exemplary Family 6 glycosyl hydrolases. In the disclosed configurations, at least one of, and in some configurations, preferably all of, the beta sheets 1 to 4 and 7 provide residues for contact with mannan substrates for hydrolysis thereof. Further, the catalytic domain retains sequence defined by SEQ. ID. NO. 3 illustrated in FIG. 2 and shares at least about 70% amino acid sequence identity, alternatively at least about 80% identity, and in certain configurations at least about 90% identity with SEQ. ID. NO. 3. In alternative configurations the recombinant peptide catalytic domain shares at least about 95% positivity (identity including conservative substitutions) and, further, in some embodiments between about 98% and about 99% positivity with the sequence shown in FIG. 2.

Without limitation by theory, the percent sequence identity is determined by various methods known to those of skill in the art. For example, sequence identity may be determined by means of computer programs such as GAP provided in the GCG program package (Program Manual for the Wisconsin Package, Version 8, August 1994, Genetics Computer Group, 575 Science Drive, Madison, Wis., USA 53711) as found published according to Needleman, S. B. and Wunsch, C. D., Journal of Molecular Biology 48 (1970) 443-453, which is hereby incorporated by reference in its entirety. GAP is used with the following settings for polypeptide sequence comparison: GAP creation penalty of 3.0 and GAP extension penalty of 0.1. Likewise, the sequence identity of polynucleotide molecules is determined by similar methods using GAP with the following settings for DNA sequence comparison: GAP creation penalty of 5.0 and GAP extension penalty of 0.3.

Modified Recombinant Enzymes Derived from *Dictyoglomus* Species

In certain embodiments, a *Dictyoglomus* endomannanase peptide is provided that demonstrates thermostability and alkaline affinity and includes a glycosyl hydrolase family 26 mannanase catalytic domain and a Carbohydrate Binding Module 6 (CBM6) N-terminal sequence that was shown by the present inventors to confer thermostability.

In instances, the present recombinant peptide is configured for a prolonged half-life at elevated temperature and alkaline conditions. In instances, the half-life may be manifest or otherwise illustrated by hydrolytic activity at an elevated temperature and for an extended duration of time. For example, the recombinant peptide described herein has an extended half-life at a temperature of at least about 70° C. (158° F.). In other instances, the extended half-life may be manifest or otherwise illustrated by hydrolytic activity at an increased pH (alkalinity). For example, the recombinant peptide described herein has an extended half-life at an alkalinity of at least about pH 8.

The aforementioned thermostability and alkaline-stability of the catalytic domain was demonstrated to be derived from a thermostable amino acid sequence positioned N-terminal to the catalytic domain. Generally this N-terminal sequence confers improved half-life on the recombinant peptide at given reaction conditions for endomannanase activity, especially those conditions such as, but not limited to temperatures of at least about 70° C. (158° F.), alternatively, temperatures of at least about 80° C. (176° F.); and in certain conditions the temperatures are at least about 90° C. (194° F.), and endomannanase activity is maintained. Also, the given reaction conditions for alkaline-stable endomannanase activity may comprise at least about pH 8, alternatively at least about pH 9, and in certain instances the conditions comprise at least about pH 10.5. Without limitation by theory, the recombinant peptide of the disclosed herein with the N-terminal sequence has a greater half-life at under the temperature and alkaline conditions described than does a peptide that has a catalytic domain of the recombinant peptide as disclosed, but lacks the thermostability sequence located N-terminal to the catalytic domain.

For example, referring now to FIG. 3 the sequence of amino acids (SEQ. ID. NO. 21) located N-terminal to and conferring thermostability on the catalytic domain disclosed hereinabove comprises between about 100 and about 150 residues, alternatively between about 110 and about 140 residues, and in certain configurations of the present recombinant peptide, the N-terminal thermostable amino acid sequence comprises about 130 residues. Further, the N-terminal thermostable amino acid sequence has homology with Family 6 carbohydrate binding modules (CBM6). Still further, the N-terminal thermostable sequence may or may not bind to mannan. In configurations disclosed herein, the N-terminal thermostable sequence comprises at least one of sequences N1 and N2 as shown in bold in FIG. 3. In certain configurations, N1 consists of the sequence EAENGVLNGT (SEQ. ID. NO. 22) and N2 consists of the sequence WGWFLLDYFK (SEQ. ID. NO. 23). N1 and N2 are in the CBM6-discoidin-like or CBM6 endomannanase like domain of the native enzyme. In certain amino terminal truncated enzyme versions, the amino terminal CBM6 domain of the native enzyme is shortened and contains only the N2 domain.

In certain embodiments the sequence of amino acids conferring thermostability on the catalytic domain, the N-terminal thermostable sequence comprises at least about 70% amino acid sequence identity, alternatively at least about 80% identity, further at least about 90% identity with the native enzyme. In certain exemplary configurations, the N-terminal thermostable sequence comprises at least about 95% positivity (identity including conservative substitutions), and in certain instances between about 98% and about 99% positivity (identity including conservative substitutions) with the sequence shown in FIG. 3.

In one embodiment, a recombinant endomannanase peptide sequence (SEQ. ID. NO. 24) is provided as illustrated in FIG. 4A. The recombinant peptide shares sequence identity with the reference aa sequence for the complete *D. thermophilum* mannosidase found under NCBI accession YP_002249896 and shown as SEQ. ID. NO. 1 in FIG. 1. As depicted the recombinant peptide sequence of SEQ. ID. NO. 24 includes an additional reiterated sequence KLVTPNPSKEAQKL (SEQ. ID. NO. 25) at the start of the catalytic domain.

In exemplary configurations of the recombinant endomannanase polypeptide, the polypeptide is glycosylated. However, glycosylation is not necessarily required for the disclosed activity under the disclosed conditions of the recombinant peptide. Exemplary conditions comprise without limitation hydrolytic activity for highly substituted mannan backbones, at high temperature and high pH (highly alkaline) conditions.

Generally, there is provided a nucleic acid encoding a recombinant endomannanase peptide comprising a catalytic domain as disclosed herein. In one embodiment, the nucleic acid has a sequence as shown in FIG. 5 (SEQ. ID. NO. 26). SEQ. ID. 26 is 99% homologous with the catalytic domain of the *D. thermophilum* beta-mannanase (manA) gene of gi|2582052, disclosed by Gibbs, M. D., et al. "Sequencing and expression of a beta-mannanase gene from the extreme thermophile *Dictyoglomus thermophilum* Rt46B.1, and characteristics of the recombinant enzyme. Curr. Microbiol. 39 (6) (1999) 351-357. The nucleotide sequence of SEQ. ID. NO. 26 encodes the 316 amino acid sequence of FIG. 2 herein.

Also provided is a nucleic acid encoding a recombinant endomannanase peptide as disclosed herein in FIG. 6 (SEQ. ID. NO. 27). The nucleotide sequence of SEQ. ID. NO. 27 encodes a 449 aa peptide running from the beginning of the CBM6 module to the end of the Ref Seq shown in SEQ. ID. NO. 1.

Alternatively, in certain embodiments, the nucleic acid sequence encoding a recombinant endomannanase peptide comprises at least about 70% nucleotide sequence identity, alternatively at least about 80% identity, and in certain configurations, the nucleic acid sequence encoding a recombinant endomannanase peptide comprises at least about 90% identity with the sequence disclosed herein. Still further, in certain embodiments the nucleic acid sequence encoding a recombinant endomannanase peptide comprises at least about 95% identity and in certain configurations between about 98% and about 99% identity with the sequences shown in FIG. 5 or 6.

Vectors for Commercial Production of Enzymes Breakers (or Endomannanases)

It may be understood that the present disclosure includes any vector including a nucleic acid encoding recombinant peptide or catalytic domain disclosed hereinabove. Likewise, the present disclosure includes a host cell including a vector including a nucleic acid encoding recombinant peptide or catalytic domain disclosed hereinabove. The host cell may be prokaryotic or eukaryotic, without limitation. Still further, a cell comprises any that may be used particularly for recombinant production, including unicellular algae, bacterium, fungus, or other unicellular organisms, without limitation. In instances, the host cell comprises any from the genus *Dictyoglomus*, the bacterium *E. coli*, the filamentous fungus *Trichoderma reesei* (*T. reesei*), or combinations and recombinants thereof, without limitation.

The present disclosure comprises and provides a process for producing an expression product in the form of a recombinant peptide according to the invention including introducing a nucleic acid according to the invention into a cell and culturing the cell in conditions for expression of a recombinant peptide according to the invention, thereby producing said expression product. Likewise, there is provided a nucleic acid encoding the peptide, vectors containing the nucleic acid, cells containing the vector and expression products produced by said cells.

Commercial Production of Dt Endomannanases in *E. coli*

In certain embodiments, the *Dictyoglomus* mannanase enzyme was produced in commercial quantities by cloning the gene into an expression vector for production in a high expression host. Exemplary suitable high expression hosts for expression of exogenous *Dictyoglomus* genes include both prokaryotic and eukaryotic hosts.

For example, the *Dictyoglomus* mannanase enzymes disclosed herein have been successfully produced in *Escherichia coli* ("*E. coli*") as an exemplary prokaryotic host and in *Trichoderma reesei* ("*T. reesei*") as an exemplary eukaryotic host. For purposes of maximized expression in exogenous hosts, the nucleic acid sequence may be codon optimized. FIGS. 7A and B show an exemplary *D. thermophilum* mannanase nucleic acid sequence, SEQ. ID. NO. 29, and an overlying codon optimized sequence for expression in *E. coli*, SEQ. ID. NO. 28. The optimized codons are underlined. The codon optimized sequence, SEQ. ID. NO. 28 is one non-limiting example of a codon optimized sequence for expression in *E. coli* and other optimization schemes may be utilized for expression in this or another given organism. Under the depicted optimization scheme, a nucleic acid identity of 75% or 902/1197 is obtained by sequence alignment with a *D. thermophilum* reference sequence of the analogous region. A nucleic acid identity of 75% or 899/1197 is obtained by sequence alignment with a *D. turgidum* DSM 6724 reference sequence of the analogous region. Conversion of the depicted sequence to an amino acid sequence provides the amino acid sequence for an amino terminal truncated *D. thermophilum* mannanase shown in FIG. 7C. The depicted aa sequence begins at aa 72 of SEQ. ID. NO. 1 and the MYEL of the reference sequence (shown underlined) is converted to MHEL. The Y to H conversion is a conservative substitution and the native MYEL sequence may alternatively be utilized. As such, the amino acid sequence of FIG. 7C provides a *Dictyoglomus* mannanase in which the amino terminal CBM6 domain is truncated thus reducing steric hindrance but retaining a thermostability domain, in this example, specifically the N2 thermostability domain shown double underlined. Compared to the wild type enzyme of 469 aa, the depicted amino terminal truncated enzyme is 398 aa.

In one embodiment the DTManA is produced in *E. coli* strain BL21(DE3), which is an *E. coli* B strain with DE3, a λ prophage carrying the T7 RNA polymerase gene and lacI. Transformed plasmids containing T7 promoter driven expression are repressed until IPTG (or Lactose) induction of T7 RNA polymerase from a lac promoter. In one embodiment, the transformed *E. coli* host cells are grown in Terrific Broth (TB). Following production, the enzyme is highly soluble in the cytosol and exhibits minimal inclusion body formation when over-expressed in *E. coli* at 37° C. The recombinant gene product has a molecular weight of 52 kDa and a temperature optimum of 80° C. After completion of fermentation, the fermentation broth is centrifuged to collect the bacterial cells and the supernatant is discarded. The cells are lysed with a French press and the lysed cells centrifuged out. Antimicrobial preservative salts are added and the supernatant is heat treated at 75° C. (167° F.) for 1.5 hrs to precipitate most of the host *E. coli* proteins. The heat denatured and aggregated proteins are removed by centrifugation.

Commercial Production of Dt Endomannanase in *T. reesei*

In another exemplary embodiment *Trichoderma reesei* is used as an exogenous eukaryotic host for commercial production. *T. reesei* (syn. *Hypocrea jecorina*) is a mesophilic and filamentous fungus that has the native capability of secreting large amounts of cellulolytic enzymes including cellulases and hemicellulases. *T. reesei* is thus a main industrial source of cellulases and hemicellulases for use in the degrading and converting plant cell wall polysaccharides into glucose for use in biofuel production.

The gene for the *D. thermophilum* mannohydrolase enzyme was codon optimized to increase the efficiency of its expression in *T. reesei* as an exemplary eukaryotic expression host. Two non-limiting examples of cassettes for expression of a *Dictyoglomus* mannohydrolase gene in *T. reesei* are provided in FIGS. 8A and 8B. As depicted in FIG. 8A, a codon optimized mannohydrolase gene is inserted behind the strong inducible cellobiohydrolase I (cbhI) promoter for highly efficient expression. See US2011/0053218, CBH1corlin vector. After the promoter, a *T. reesei* CBH1 secretion-signal sequence is inserted. See US2011/0053218.

In the embodiment depicted in FIG. 8B, the expression cassette further includes the N-terminal pro-region of the *T. reesei* XynII xylanase (see US2011/0053218, [0035]) followed by the beginning of the *D. thermophilum* mannohydrolase enzyme carbohydrate binding module 6 (depicted in FIG. 1). Thus, for sufficiently high expression to be commercially viable *T. reesei* is utilized as the expression host and the 5' untranslated region preceding the native *D. thermophilum* mannanohydrolase enzyme coding region is replaced to maximize expression in *T. reesei*.

The restriction enzyme cloning sites are as depicted in FIG. 9A-C showing the sequence of both nucleic acid strands (codon optimized) in SEQ. ID. NOS. 31 and 32. The respective amino acid sequence is shown under the nucleic acid sequences as SEQ. ID. NO. 33. Highlighted in bold and underlined are a potential KEX-like proteolytic site (RQ) and an ER-like retention signal (KDEL). As depicted there is an extra amino acid (V) inserted as a result of using the PmlI site in place of Methionine (in wild type version). The NcoI and SalI restriction sites were used for cloning and expression in E. coli. The PmlI and AflII sites were used for cloning into T. reesei expression cassettes. As shown, this version of the Dictyoglomus mannohydrolase enzyme is essentially full length without a truncated amino terminus.

FIG. 10A-B depict an alignment of the nucleotide sequence of the codon optimized Dt mannohydrolase of FIG. 9A-C (Query Sequence) (SEQ. ID. NO. 34). Underlying is a type sequence (gb|CP001146.1) for *D. thermophilum* (Dt) mannohydrolase (SEQ. ID. NO. 35). As a consequence of the codon optimization, the nucleic acid sequence of the codon optimized gene shares 75% homology with the wild type. FIG. 10C depicts an exemplary amino acid sequence (SEQ. ID. NO. 36) encoded by the nucleic acid sequence of SEQ. ID. NO. 34.

Figure 24:
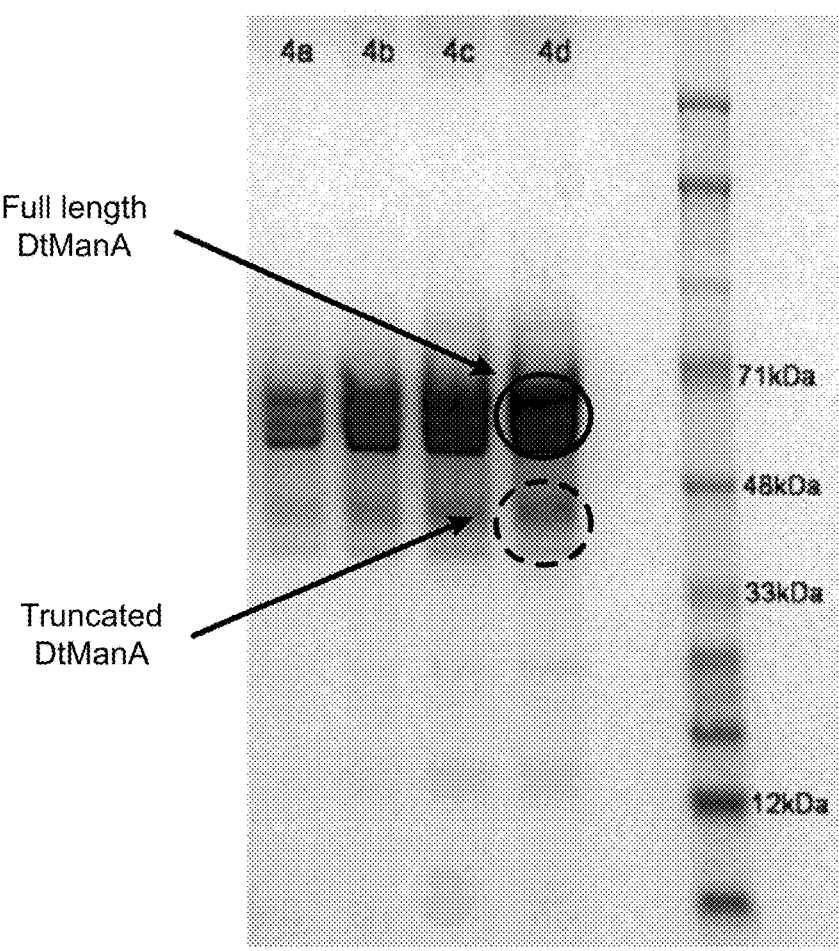
FIG. 24 shows the purity of DtManA in a heat treated supernatant after extracellular expression in T. reesei

In one embodiment the DTManA is produced in *T. reesei* in commercial scale fermentation. Expression in *T. reesei* using expression cassettes such as that shown in FIG. 8B results in extracellular secretion of the DT ManA. Thus, following production the culture supernatant is clarified by transferring the feed fermentation broth through a stacked disk centrifuge. Antimicrobial preservative salts are added and the supernatant is heat treated at 80° C. (176° F.) for 1 hr to precipitate most of the host *T. reesei* proteins. The heat denatured and aggregated proteins are removed by repeat centrifugation through a stacked disk centrifuge. When produced at commercial scale in *T. reesei*, the clarified and heat treated broth is remarkably purified DTManA as shown on the SDS-PAGE gel of FIG. 24. Importantly, the partially purified DTManA provided as a clarified fermentation broth purified as described herein without concentration or further purification is storage stable at 4° C. (39° F.) and 25° C. (77° F.) for at least 40 days without loss of activity and is useable as a direct additive to guar-based frac fluids.

Attributes of Exemplary Glycosyl Hydrolases

Without limitation, there is disclosed herein the use of a recombinant peptide described herein for cleaving a mannan backbone, in certain applications a highly substituted backbone and to methods including same. In exemplary configurations of the method, the recombinant peptide described herein may be used as an enzyme breaker in frac fluids. In other embodiments the disclosed enzymes may be utilized in paper and pulp treatment, coffee hydrolysis, detergent formulation, livestock feed preparation, and others without limitation.

A particular key aspect of the enzymes provided herein is that while they have optimum activity in excess of 80° C. (176° F.), they are stable in the range of approximately 4° C. (~40° F.) to in excess of 120° C. (~250° F.). The presently disclosed *Dictyoglomus* enzymes are considerably less active at surface temperatures but will begin robust breaking of guar gellants in high downhole temperatures and conditions (pressures) after proppant deposition. In fracturing situations this allows them to be mixed with guar and derivatives thereof without substantially breaking the guar above surface (up-hole) conditions and during pumping, so the entire job can be placed with minimal fluid degradation ensuring optimal proppant transport and suspension. However, when the frac fluid is driven downhole, the formation will heat the frac fluid including the gellant and the enzyme breaker will begin a rapid, but controlled breaking of the frac fluid as the enzyme begins to reach its high temperature optimum.

Another aspect of the enzymes provided herein is that while they have optimum catalytic activity between pH 6 and 8, they are stable at a high pH range of over 9.5 and while they will exhibit considerable activity at high pH, this activity requires high temperature. Once the frac fluid is pumped into the formation, it begins to be neutralized by the formation and the optimal pH for maximal activity of the enzyme is reached. Importantly, the stability of the *Dictyoglomus* enzymes through the range of pH 3 to pH 12 means that these enzymes can be used with different fracturing fluid systems across a broad pH range enabling applicability to fracing fluids including different cross-linkers that require vastly different pH values.

Importantly, the stability of the presently disclosed *Dictyoglomus* enzymes at extremes of pH coupled with greatly reduced activity at surface temperatures and during pump time, allows the frac fluid, including both guar and enzymes to remain at very high viscosity for hours (including during pumping) thus ensuring optimal proppant transport and suspension. In some instances when batch mixing is performed and enzymes are added to the mixture, the viscosity would be able to be maintained even a day or more (at the surface) if the frac job is delayed.

In contrast, prior enzyme breakers would be either inactivated by extremes of pH or would be sufficiently active to begin breaking the frac fluid immediately upon addition. Thus, with prior enzyme breakers, or enzymes that are highly active at high pH, the frac fluid is immediately being degraded and therefore reducing the fluid integrity needed to create the fracture, place the proppant and ensure optimum proppant suspension. Sometimes the existing enzymes are so active that premature breaking could lead to screen-outs. Highly active high pH enzymes also have the disadvantage (or are inefficient) because, while active at high pH during (pumptime), once the fluid pH starts lowering (by the action of the formation) the enzymes become less and less active, reducing their long term activity needed to clean the frac fluid damage in the proppant pack or formation faces (filter-cake). Thus, existing high pH active enzymes become less and less efficient in cleaning up the frac fluid damage and reducing proppant pack conductivity such that their use potentially or essentially reduces optimal well productivity.

In contrast, when using the presently disclosed *Dictyoglomus* enzymes that are stable but have reduced activity at surface conditions, and yet become more and more active under down-hole conditions, long term activity is ensured, which leads to cleaner proppant packs, reduced filter-cake damage, and increased well productivity. Regained conductivity testing performed by an independent laboratory, has shown that the *Dictyoglomus* enzymes disclosed herein can provide for regained conductivity results of over 85% at 180° F. (82° C.) and 250° F. (121° C.).

In one example herein provided, aqueous fracturing fluids may be prepared by blending a hydratable gellant polymer powder into an aqueous fluid. The hydratable gellant polymer powder is added to the aqueous fluid in concentrations ranging from about 0.10% to 1.2% by weight of the aqueous fluid. The most preferred range for the present invention is about 0.20% to 0.84% by weight. The pH of the fracturing fluid may generally range from about 4.0 to about 12, typically about 6.0 or higher. In a preferred embodiment, the pH of the fracturing fluid is greater than or equal to 5.5 in the case of zirconium crosslinkers and greater than or equal to about 9.5 in the case of boron crosslinkers.

In certain embodiments, the presently disclosed *Dictyoglomus* enzymes are provided in liquid form and are supplied to the job site and then added by volume to the mixing tank where the gellant powder is being hydrated. In other embodiments, the presently disclosed *Dictyoglomus* enzymes are dried and supplied to the job site in powder form. Dried formulations may be added by weight to the concentrated polymer slurry for rehydration at the same time as the hydratable gellant polymer. Alternatively, in one embodiment, the dried *Dictyoglomus* enzymes are supplied premixed with the hydratable gellant polymer also in powder form. Thus, both the powdered *Dictyoglomus* enzyme and the guar based gellant are simultaneously rehydrated.

Stability and Activity Assays.

In support of the stability and maximum activities disclosed above, a certain examples are provided. The method of Lever (Lever M. Colourimetric and fluorimetric carbohydrate determination with p-hydroxybenzoic acid hydrazide. Biochem. Med. 7 (1973) 274-281) was used to determine the release of reducing sugars due to cleavage of the mannan backbone. The standard assay was performed at 80° C. in McIlvaines buffer (0.128 mM $Na_2HPO_4$, 0.036 mM citric acid) pH 6.2 for 30 minutes.

In comparative thermostability assays, an appropriate quantity of mannanase was incubated at 80° C. in either McIlvaines buffer pH 6.2 (200 mM sodium phosphate, 100 mM citric acid); 0.13 M carbonate buffer pH 9.75 (13 mM potassium carbonate, 50 mM potassium bicarbonate, 2% KCl); or 0.13 M carbonate buffer, pH 9.75 with 0.1% guar. Aliquots of each solution were removed at appropriate time points, and the remaining enzyme present determined by performing the standard assay under non-substrate limiting conditions. Mannanase inactivation constants were calculated as the slope of $\ln(A_t/A_0)$, where $A_t$ equals the relative mannanase activity measured at time t, and $A_0$ equals the relative mannanase measured at time zero. Half-lives were calculated as $\ln(2)/k_d$ for each series.

A comparison was made under various conditions of the stability of the full length recombinant *D. thermophilum* ManA enzyme and a version of ManA described by Gibbs et al (1999) that has only a catalytic domain. The results are presented in Table 1.

TABLE 1

Stability of mannanases at 176° F. (80° C.) expressed as half-lives, at different pHs, in the presence and absence of galactomannan (Guar gum)

| Incubation Conditions | Kd | D. thermophilum ManA | Kd | D. thermophilum ManA catalytic domain only |
|---|---|---|---|---|
| 0.1 M McIlvaines buffer, pH 6.2 | 0.0065 | 106.6 min | 0.0174 | 39.8 min |
| 0.13 M carbonate buffer, pH 9.75, KCl 2% | 1.7062 | 0.41 min | 3.3796 | 0.2 min |
| 0.13 M carbonate buffer, pH 9.75, KCl 2%, guar gum 0.1% | 0.0159 | 43.6 min | 0.1651 | 4.2 min |

In summary, under all conditions tested, the full-length mannanase was found to be significantly more stable than a catalytic domain only form of the mannanase. The absence of the N-terminal CBM6 domain decreased stability substantially at moderate pH (pH 6.2) and alkaline pH (pH 9.75). The presence of the substrate under alkaline conditions greatly increased the stability of the full-length enzyme, and to a lesser degree the catalytic domain only form of the enzyme.

Comparison of Reducing Sugar Profiles Obtained Using Substrates Guar Gum (GG) and Locust Bean Gum (LBG).

Galactomannans are heterogeneous substrates with a backbone of beta-1,4-linked mannose substituted to varying degrees with alpha-1,6-linked galactosyl residues. Different mannanases may differ in their ability to access all beta-1, 4-linkages on the mannan backbone due to the presence of the galactose sidechains. The ability to access the galactose-shielded sites may be affected by the structure of the catalytic domain. However, mannanases often comprise catalytic domains, as well as accessory domains that may also affect the relative abilities of different mannanases to cleave all sites on the mannan backbone.

Regardless of the mechanics of the steric interference, different enzymes will achieve different degrees of digestion of different galactomannans, depending on how accessible the backbone is to digestion. Locust bean gum has a reported substitution rate of around 4 mannose residues per galactose residue, while guar gum has a reported substitution rate of around 2 mannose residues per galactose residue.

A reducing sugar assay can act as a proxy for measuring degree of cleavage of the mannan backbone. Each cleavage event of a beta-1,4-bond releases an oligosaccharide with a single reducing end that can be quantified by the assay. When no further cleavage sites can be cut the assay becomes substrate limiting, and no further increase in signal is observed, or the rate of signal increase becomes markedly reduced.

The following example summarises results obtained from reducing sugar assays using the galactomannan substrates locust bean gum and guar gum. All enzymes were assayed using the dinitrosalicylic acid (DNS assay) at close to their temperature optimum (See Table 2) using 0.5% locust bean gum (LBG) or 0.5% guar gum (GG) as substrate. Assays were performed in Britton Robinson buffer pH 6.2.

In brief, the standard assay involved mixing 10 µL diluted enzyme (diluted in Britton Robinson buffer, pH 6.2) with 40 µL 0.5% substrate, incubating exactly 10 minutes at the appropriate assay temperature for each enzyme, then cooling immediately to 4° C. DNS solution (75 µL), was then added, and the mixture heat to 99° C. for 10 minutes. Precipitated material was then pelleted by centrifugation, and 80 µL of supernatant transferred to a 96 well microtitre plate for measurement of absorbance at 570 nm (A570).

The following data in Table 2 shows the optimal enzyme activity temperature for mannanases derived from 8 different thermophilic bacterium. These temperature optimums were used to conduct the comparisons between guar and locust been gum.

TABLE 2

| Enzyme | Temperature Optimum | Assay Temperature | GH Family of catalytic domain |
|---|---|---|---|
| Thermotoga maritima Man5 | 90° C. (194° F.) | 90° C. | 5 |
| Thermotoga neapolitana Man5 | 90° C. | 90° C. | 5 |
| Thermotoga sp. FjSS3B.1 Man5 | 90° C. | 90° C. | 5 |
| Bacillus agaradhaerens ManA | 60° C. (140° F.) | 60° C. | 5 |
| Bacillus sp. strain N16-5 ManA | 60° C. | 60° C. | 5 |

TABLE 2-continued

| Enzyme | Temperature Optimum | Assay Temperature | GH Family of catalytic domain |
|---|---|---|---|
| Caldibacillus cellulovorans ManA | 85° C. (185° F.) | 80° C. | 5 |
| Caldicellulosiruptor sp. strain Rt8B.4 ManA | 70° C. (158° F.) | 80° C. | 26 |
| D. thermophilum Rt46B.1 ManA | 80° C. | 80° C. | 26 |

Table 3 summaries the ability of 8 mannanases in their relative abilities to both digest guar gum and locust bean gum. The data summarises relative initial rates of activity on the two substrates, and also the signal achieved when substrate becomes linear. Substrate limiting conditions were not achieved over the course of assay.

TABLE 3

Reaction rates and end points for each carbohydrate and enzyme

| | Relative initial rates of activity each enzyme | | Maximum signal achieved after substrate limiting conditions reached | |
|---|---|---|---|---|
| | LBG | Guar gum | LBG End Pt. | GG End Pt. |
| T. maritima Man5 | 100 | 32 | 1300 | 400 |
| T. neapolitana Man5 | 100 | 22 | 1300 | 400 |
| Thermotoga sp. FjSS3B.1 | 100 | 29 | 1200 | 500 |
| Caldicellulosiruptor Rt8B4 ManA | 100 | 33 | 1300 | 1200† |
| Caldibacillus cellulovorans ManA | 100 | 51 | 1400 | 1400 |
| D. thermophilum ManA | 100 | 64 | 1500 | 1500 |
| B. agaradhaerens ManA | 100 | 28 | 1300 | 700 |
| Bacillus sp. N16-5 ManA | 100 | 34 | 1200 | 600 |

In summary, the *Dictyoglomus* ManA enzyme exhibited more closely similar initial rates of digestion for both guar gum and locust bean gum, indicating minimal interference by the galactose present in guar gum. In comparison, enzymes such as those tested from *Thermotoga* and *Bacillus* species showed substantially lower initial rates on guar gum compared to locust bean gum, and substantially lower end points were achieved for guar gum indicating fewer sites on the mannan backbone were accessible to these enzymes compared to the *Dictyoglomus* mannanase.

Figure 12:
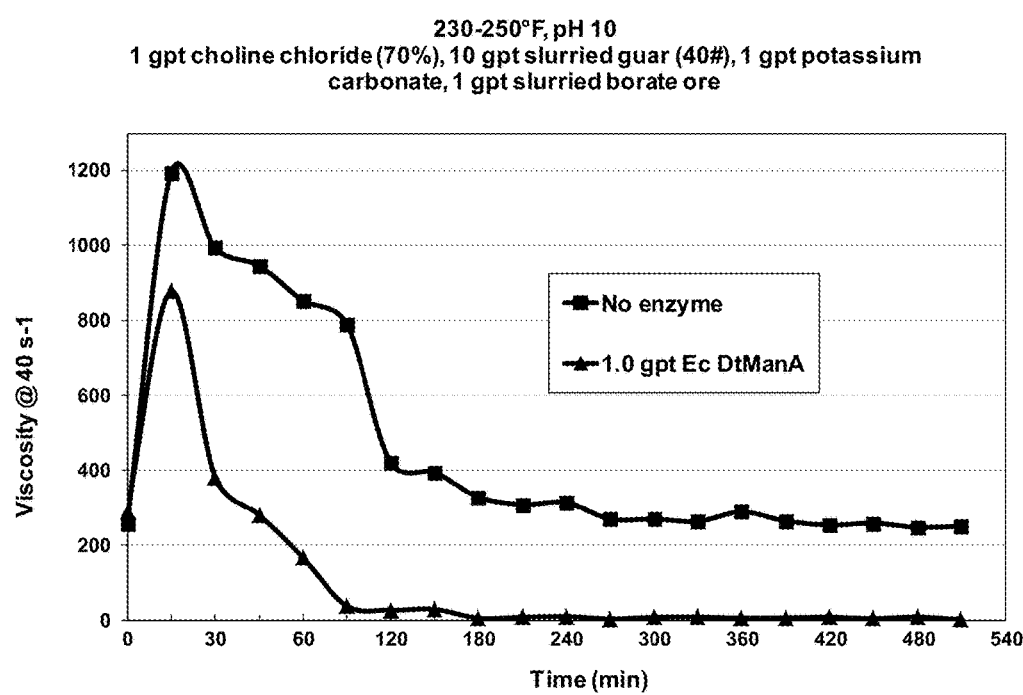
FIG. 12 is a data graph that illustrates the viscosity degradation in a 40 ppt borate crosslinked guar polymer at 230-250° F. and pH 10, showing rheology curves with and without the enzyme, showing the effectiveness of an amino terminal truncated recombinant *D. thermophilum* mannanase expressed from a codon optimized gene in *E. coli*. (Ec DtManA).

D. thermophilum Mannanase Activities in Conditions Simulating Downhole Fracturing Environments In one embodiment the *D. thermophilum* mannanase gene sequence of FIG. 7A-B (SEQ. ID. NO. 28), which was codon optimized for expression in the exogenous host *E. coli*, was recombinantly inserted into a plasmid expression vector and used to transform *E. coli*. The transformed *E. coli* was placed into batch fermentation. The *Dictyoglomus* ManA enzyme is isolated as an intracellular enzyme from *E. coli*. The guar breaking properties of the ManA enzyme were tested under a number of conditions simulating those of frac fluids. FIGS. 11-12 are exemplary of certain of the tests that were conducted. Thus, the activity of the enzyme is demonstrated at 180° F. (82.2° C.) and pH 9.7 as well as at 230-250° F. (110-121° C.) and pH 10. The demonstrated ManA of FIGS. 11 and 12 has an amino terminal truncation and thus includes only a portion of its CBM6 domain. Under the conditions shown, this ManA enzyme could be seen to break the guar gel quickly with viscosity reaching almost that of water within one hour (less than one cps at $511^{S-1}$). Depending on the application, it is apparent that modified ManA enzymes can be generated that have more rapid action if desired.

FIG. 11 is a data graph that illustrates the viscosity degradation in a 30 ppt borate crosslinked guar polymer at 180° F. (82.2° C.) and pH 9.7, showing rheology curves with and without the enzyme, showing the effectiveness of an amino terminal truncated recombinant *D. thermophilum* mannanase enzyme expressed from a codon optimized gene in *E. coli*. (Ec DtManA).

FIG. 12 is a data graph that illustrates the viscosity degradation in a 40 ppt borate crosslinked guar polymer at 230-250° F. (110-121° C.) and pH 10, showing rheology curves with and without the enzyme, showing the effectiveness of an amino terminal truncated recombinant *D. thermophilum* mannanase enzyme expressed from a codon optimized gene in *E. coli*. (Ec DtManA).

In one embodiment the *D. thermophilum* mannanase gene sequence of FIG. 9A-C (SEQ. ID. NO. 31), which was codon optimized for expression in exogenous host *T. reesei*, was recombinantly inserted into the plasmid expression vector depicted schematically in FIG. 8 and used to transform *T. reesei*. The transformed *T. reesei* was placed into batch fermentation and high gene expression under the influence of the inducible cbhI promoter was induced by addition of cellulose sophorose, lactose. The *Dictyoglomus* ManA enzyme is secreted extracellularly by *T. reesei* and was thus isolated from the cell free fermentation broth. The guar breaking properties of the ManA enzyme were tested under a number of conditions simulating those of fracing fluids. FIGS. 13-20 are exemplary of certain of the tests that were conducted. Thus, the activity of the enzyme is demonstrated from 130° F. (54.4° C.) to 270° F. (132.2° C.).

Figure 13:
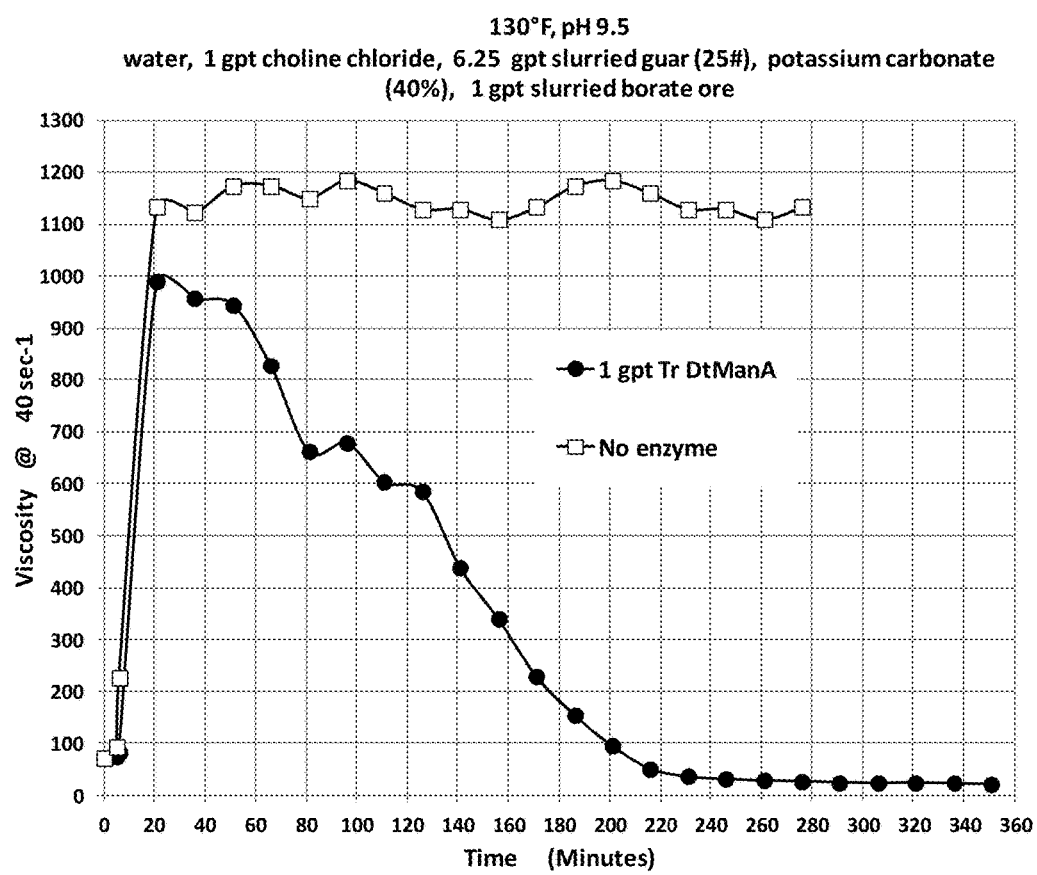
FIG. 13 is a data graph that illustrates the viscosity degradation in a 30 ppt borate crosslinked guar polymer strain at 130° F. and pH 9.5 with and without the enzyme showing the effectiveness of a recombinant *D. thermophilum* mannanase expressed from a codon optimized gene in T. reesei (Tr DtManA).

FIG. 13 is a data graph that illustrates the viscosity degradation in a 30 ppt borate crosslinked guar polymer strain at 130° F. (54.4° C.) and pH 9.5 with and without the enzyme showing the effectiveness of a recombinant *D. thermophilum* mannanase expressed from a codon optimized gene in *T. reesei* (Tr DtManA).

Figure 14:
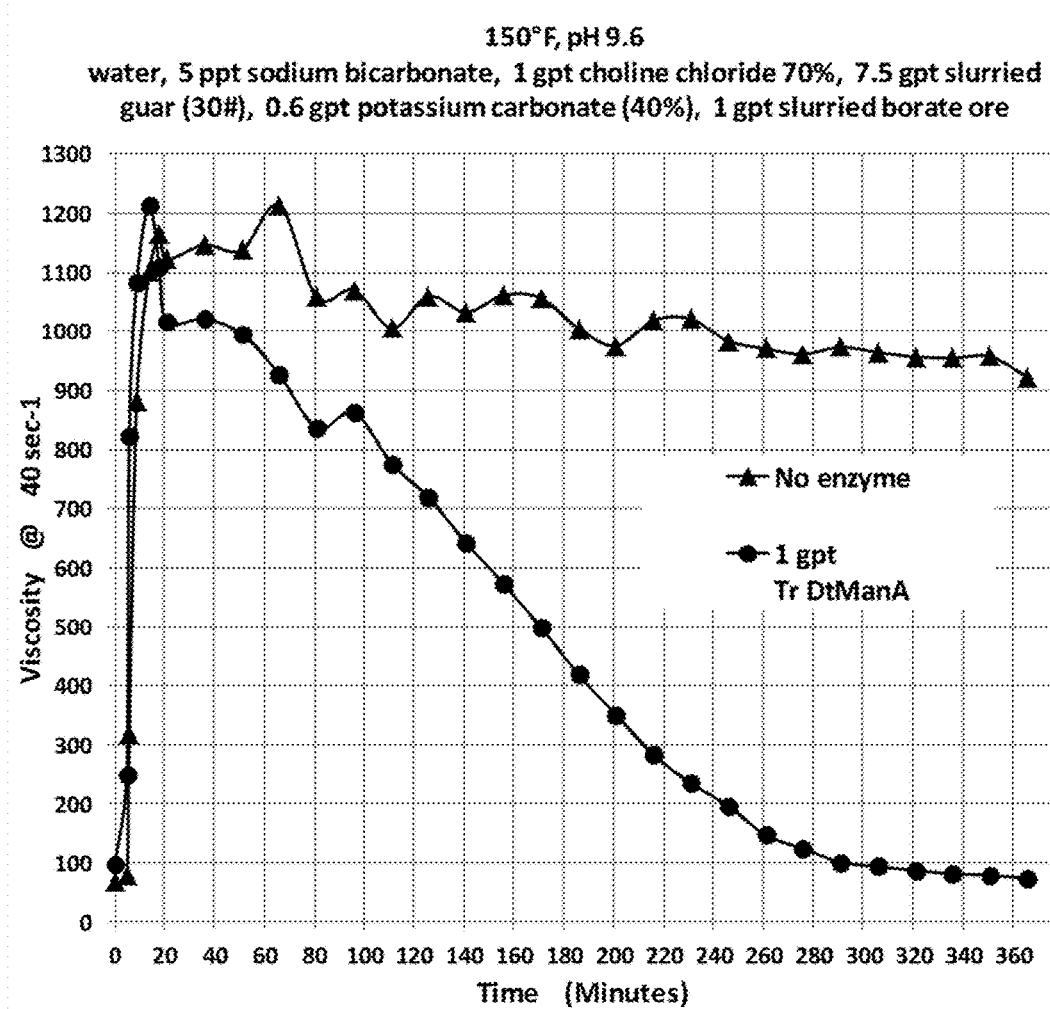
FIG. 14 is a data graph that illustrates the viscosity degradation in a 25 ppt borate crosslinked guar polymer at 150° F. and pH 9.6 with and without the enzyme, showing the effectiveness of a recombinant *D. thermophilum* mannanase expressed from a codon optimized gene in T. reesei (Tr DtManA).

FIG. 14 is a data graph that illustrates the viscosity degradation in a 25 ppt borate crosslinked guar polymer at 150° F. (65.5° C.) and pH 10.5 with and without the enzyme, showing the effectiveness of a recombinant *D. thermophilum* mannanase expressed from a codon optimized gene in *T. reesei* (Tr DtManA).

Figure 15:
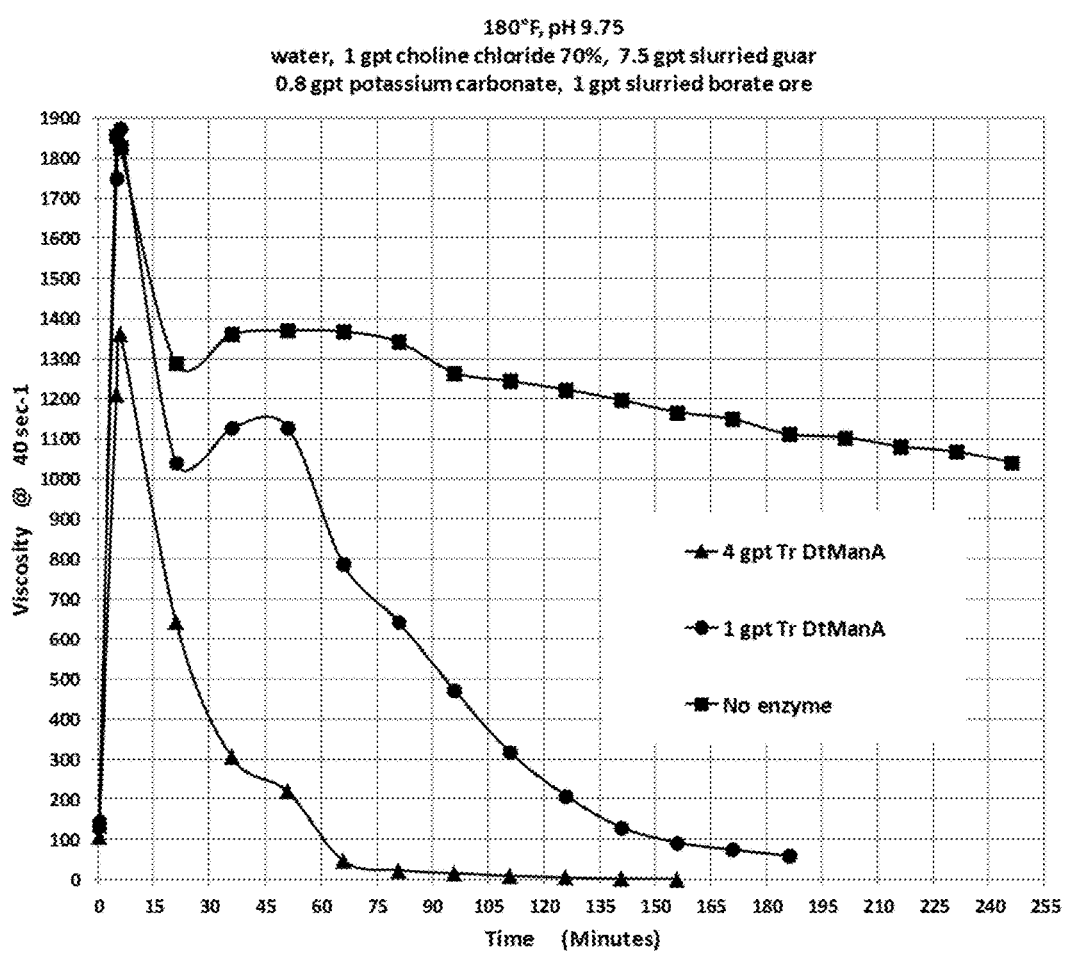
FIG. 15 is a data graph that illustrates the viscosity degradation in a 30 ppt borate crosslinked guar polymer at 180° F. and pH 9.75 at various loadings and without the enzyme, showing the effectiveness of a recombinant *D. thermophilum* mannanase expressed from a codon optimized gene in T. reesei (Tr DtManA).

FIG. 15 is a data graph that illustrates the viscosity degradation in a 30 ppt borate crosslinked guar polymer at 180° F. (82.2° C.) and pH 10 at various loadings and without the enzyme, showing the effectiveness of a recombinant *D. thermophilum* mannanase expressed from a codon optimized gene in *T. reesei* (Tr DtManA).

Figure 16:
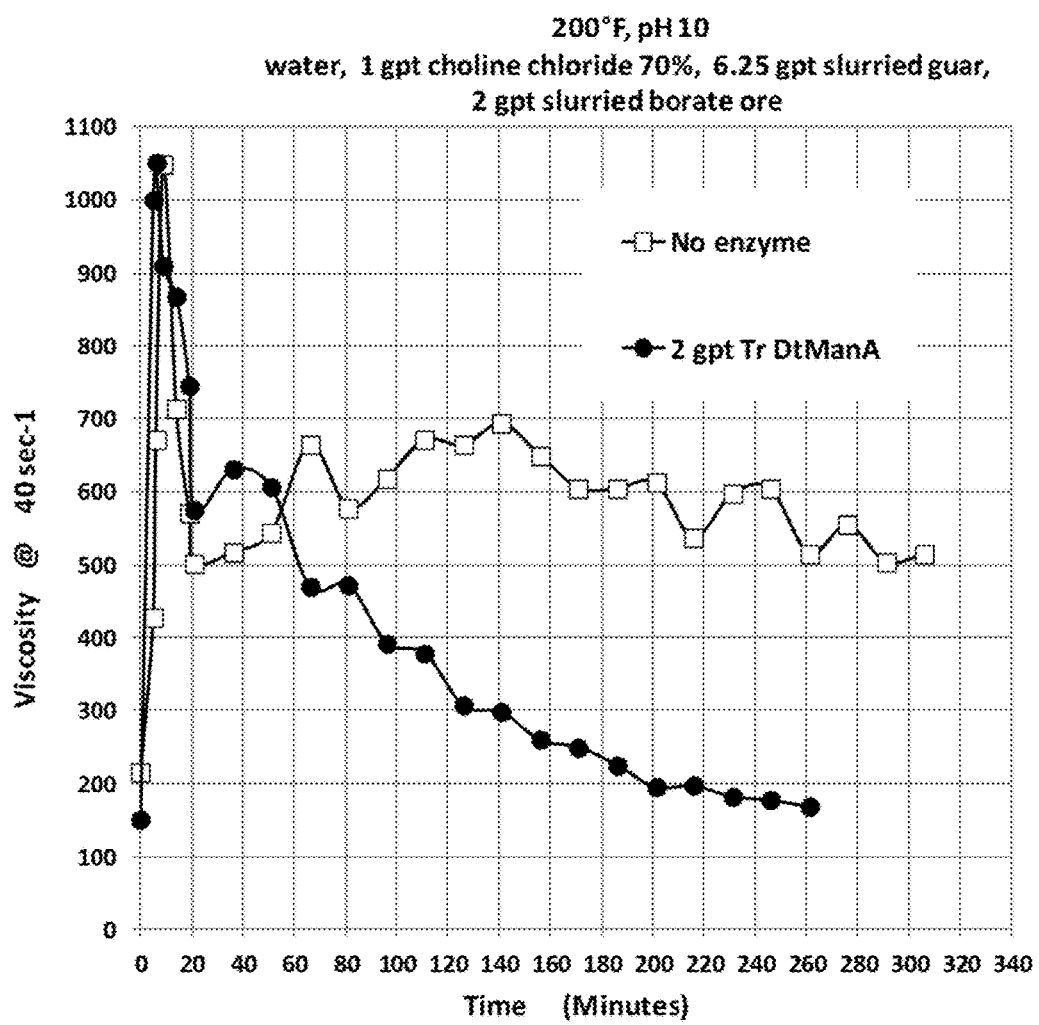
FIG. 16 is a data graph that illustrates the viscosity degradation in a 30 ppt borate crosslinked guar polymer at 200° F. and pH 10 with and without the enzyme, showing the effectiveness of a recombinant *D. thermophilum* mannanase expressed from a codon optimized gene in T. reesei (Tr DtManA).

FIG. 16 is a data graph that illustrates the viscosity degradation in a 30 ppt borate crosslinked guar polymer at 200° F. (93.3° C.) and pH 10 with and without the enzyme, showing the effectiveness of a recombinant *D. thermophilum* mannanase expressed from a codon optimized gene in *T. reesei* (Tr DtManA).

Figure 17:
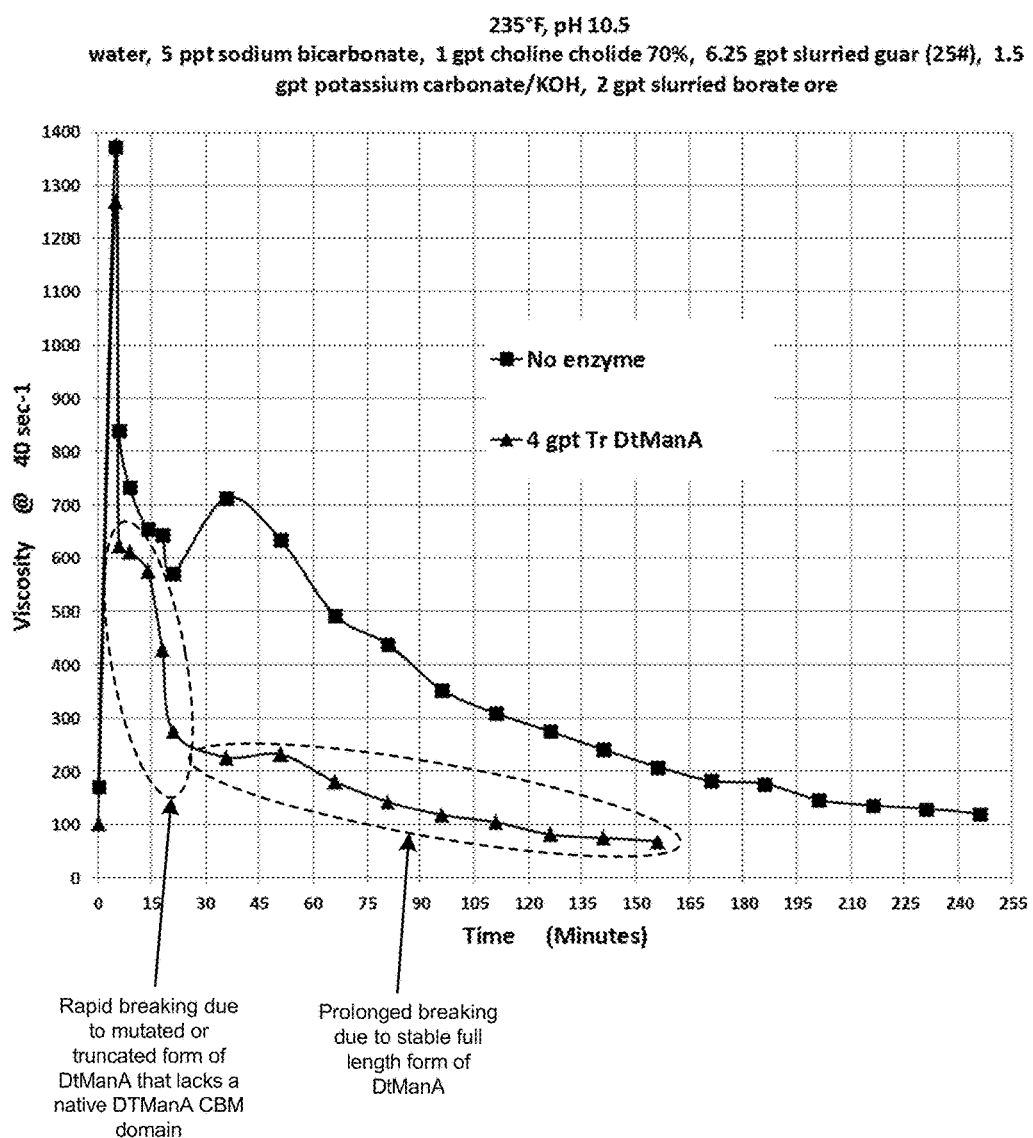
FIG. 17 is a data graph that illustrates the viscosity degradation in a 30 ppt borate crosslinked guar polymer at 235° F. and pH 10.5 with and without the enzyme, showing the effectiveness of a recombinant *D. thermophilum* mannanase expressed from a codon optimized gene in T. reesei (Tr DtManA).

FIG. 17 is a data graph that illustrates the viscosity degradation in a 30 ppt borate crosslinked guar polymer at 235° F. (112.8° C.) and pH 10 with and without the enzyme, showing the effectiveness of a recombinant *D. thermophilum* mannanase expressed from a codon optimized gene in *T. reesei* (Tr DtManA).

Figure 18:
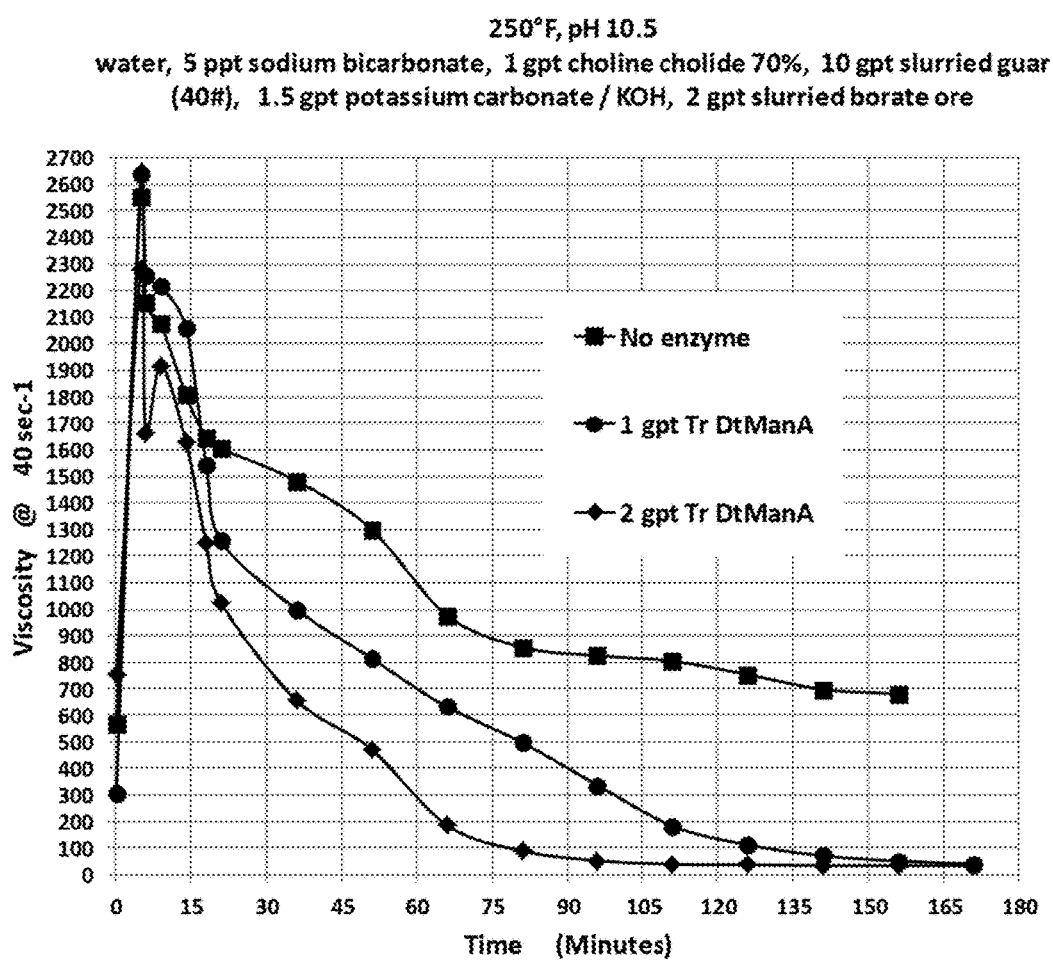
FIG. 18 is a data graph that illustrates the viscosity degradation in a 40 ppt borate crosslinked guar polymer at 250° F. and pH 10.5 at various loadings and without the enzyme, showing the effectiveness of a recombinant *D. thermophilum* mannanase expressed from a codon optimized gene in T. reesei (Tr DtManA).

FIG. 18 is a data graph that illustrates the viscosity degradation in a 40 ppt borate crosslinked guar polymer at 250° F. (121.1° C.) and pH 10.5 at various loadings and without the enzyme, showing the effectiveness of a recombinant *D. thermophilum* mannanase expressed from a codon optimized gene in *T. reesei* (Tr DtManA).

Figure 19:
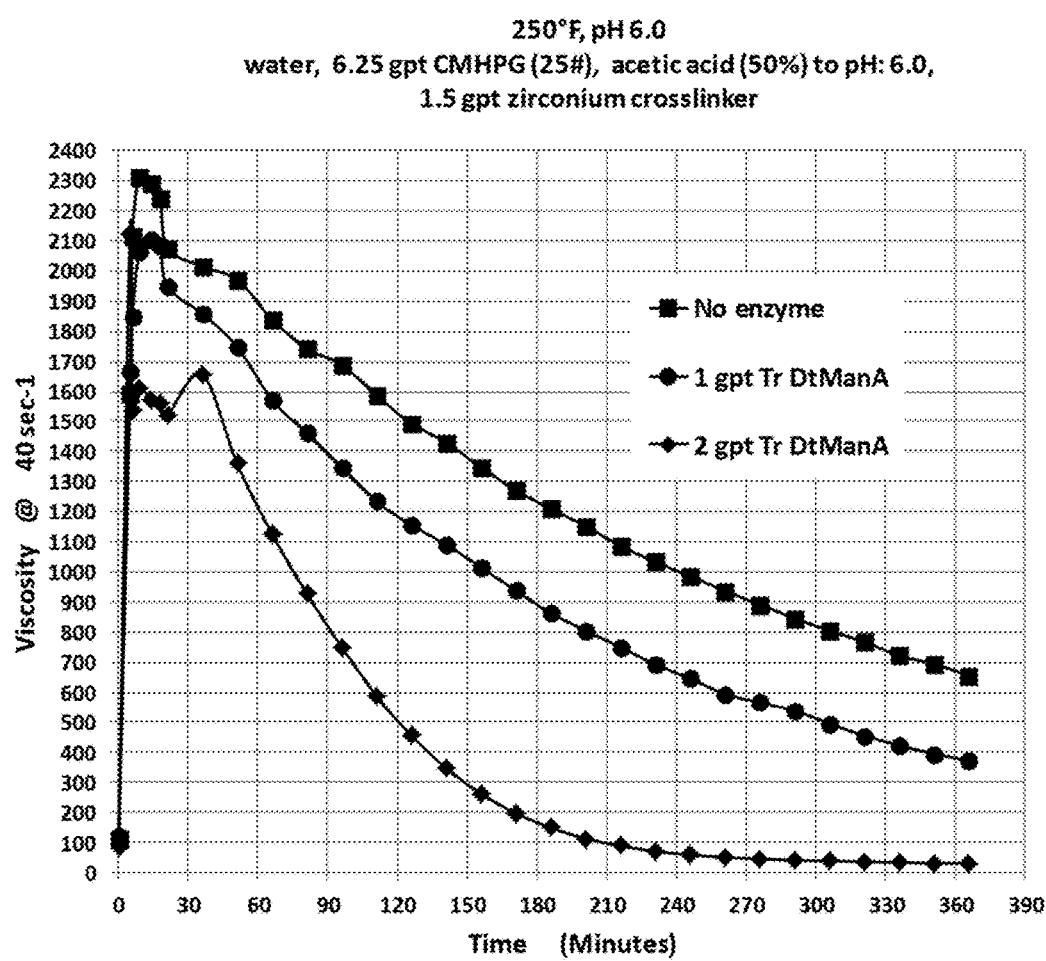
FIG. 19 is a data graph that illustrates the viscosity degradation of a 25 ppt zirconium crosslinked derivatized guar (CMHPG) at 250° F. and pH 6.0 at various loadings and without the enzyme, showing the effectiveness of a recombinant *D. thermophilum* mannanase expressed from a codon optimized gene in T. reesei (Tr DtManA).

FIG. 19 is a data graph that illustrates the viscosity degradation of a 25 ppt zirconium crosslinked derivatized guar (CMHPG) at 250° F. (121.1° C.) and pH 6.0 at various loadings and without the enzyme, showing the effectiveness of a recombinant *D. thermophilum* mannanase expressed from a codon optimized gene in *T. reesei* (Tr DtManA).

Figure 20:
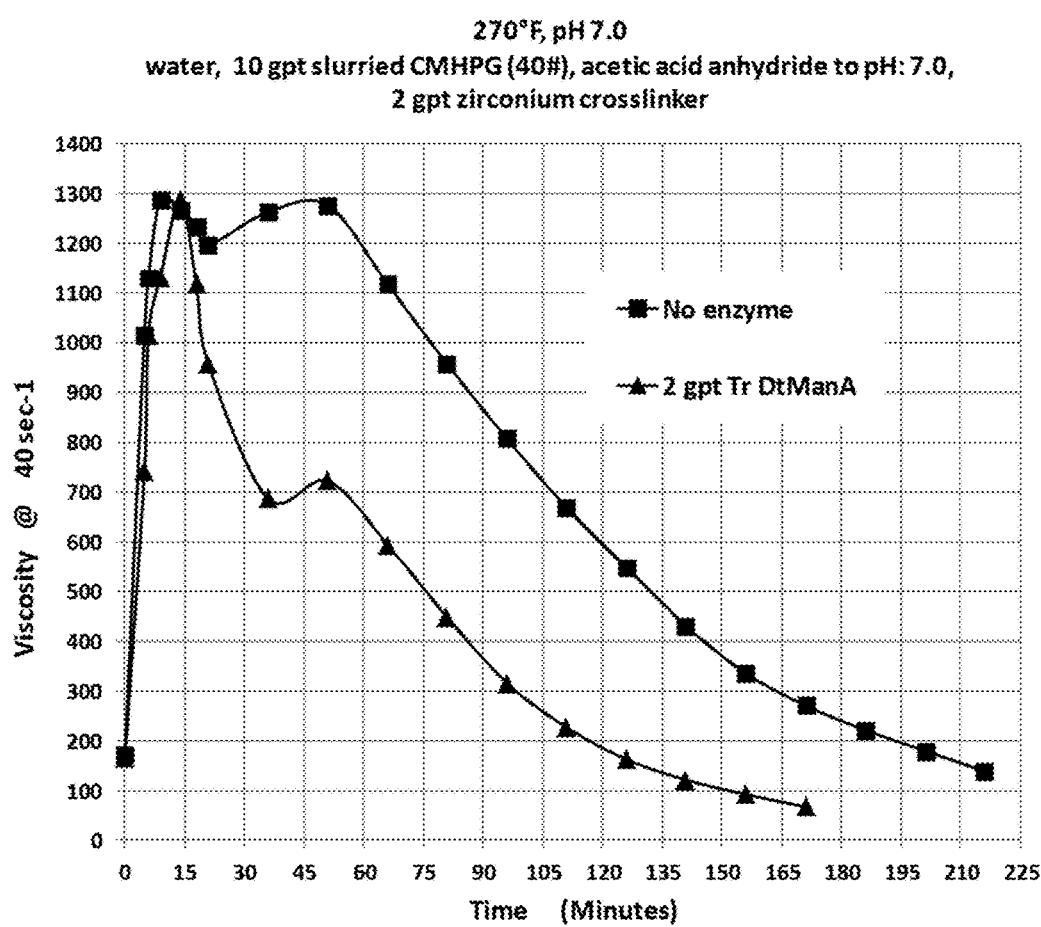
FIG. 20 is a data graph that illustrates the viscosity degradation of a 40 ppt zirconium crosslinked derivatized guar (CMHPG) at 270° F. and pH 7.0 with and without enzyme, showing the effectiveness of a recombinant *D. thermophilum* mannanase expressed from a codon optimized gene in T. reesei (Tr DtManA).

FIG. 20 is a data graph that illustrates the viscosity degradation of a 40 ppt zirconium crosslinked derivatized guar (CMHPG) at 270° F. (132.2° C.) and pH 7.0 with and without enzyme, showing the effectiveness of a recombinant *D. thermophilum* mannanase expressed from a codon optimized gene in *T. reesei* (Tr DtManA).

The data in FIGS. 11-20 demonstrate the unique thermostability and activity of *D. thermophilum* endomannanase under conditions ranging from 130° F. (54.4° C.) to 270° F. (132.2° C.). The data presented herein reveal certain of the unique properties of *Dictyoglomus* enzyme breakers, particularly for high temperature indications. Hemicellulases are the most commonly used enzyme breaker. However, hemicellulases are generally considered by the industry to be limited to use at or below 120° F. (49° C.). Thus, the industry has turned to use of oxidants such as persulfates and peroxides for use in breaking guar gellants at downhole temperatures above 250° F. (121.1° C.). As provided herein, the extreme thermal and pH stability of the *Dictyoglomus* mannanase allows use of environmentally breakers in extreme heat environments.

Improved DtManA Production in *T. reesei* by Site-Directed Mutagenesis

A total of 31 *T. reesei* transformants were isolated. A total of 13 were transformed with the codon optimized wild-type mannanase gene, and 18 were transformed with a codon optimized double-mutant gene. Based upon plate-based "halo" screening for expression of thermophilic mannanase activity, a total of 10 wild-type transformants, and 9 double mutants were selected for shake flask induction culture analysis. Shake-flask induction cultures were grown for 7 days for 18 *T. reesei* integrative transformants. The cultures were harvested and quantitative assays performed on the clarified supernatants obtained from each transformant. The assays were performed alongside an *E. coli* mannanase preparation.

Initial reducing sugar assays were performed using a 10-fold dilution series to approximately estimate the levels of mannanase activity in each sample. Five samples showed significant activity, RT1-2 & RT2-3 (double mutant variants) and RT6-3, RT6-4 and RT6-5 (wild type). The results indicate that the highest yielding transformant, in shake flask culture, is the double mutant variant RT2-3 (2-3). The best wild type transformant was RT6-5 (6-5). The RT2-3 transformant produced around 3.4× more enzyme per liter of fermentation medium compared to the best *E. coli* fermentation run to date. The sequence of the double mutant is shown in FIGS. 21A-C FIGS. 21A-C show the sequences (SEQ. ID. NOS. 37 and 38) of both nucleic acid strands (codon optimized) of the double mutant that eliminated potential signals that might prevent proper secretion of the DtManA enzyme. The respective amino acid sequence is shown under the nucleic acid sequences as SEQ. ID. NO. 39. In this double mutant embodiment there is a change in the potential KEX-like proteolytic site (RQ) proteolytic site with the R of the RQ site changed to K (position 66, R→K (CGC→AAG)). This single amino acid change removes a motif that could potentially be a KEX-like proteolytic site (RQ) that could be cleaved by a *T. reesei* proteinase. It was confirmed that this amino acid change did not affect the thermostability or activity of the mannanase. Further a potential ER-like retention signal (KDEL) was mutated to LDEL (position 1323, K→L (AAG→CTC)). On FIG. 21A, the region underlined and in bold marks the likely region of cleavage to generate the truncated catalytic form based on the observed size of the catalytic domain determined by SDS-PAGE analysis. It is believed that the cleavage point (which also defines the N-terminal of the truncated form) is in the region of the domain boundaries which contain 3 proline-threonine motifs (PT-motifs). PT-motifs are commonly found at domain boundaries of multidomain carbohydrate degrading enzymes. The region before this region is the CBM, the region after this region is the catalytic domain.

Previously we had observed that the double mutant variant when produced in *E. coli* was less thermostable than the wild-type. This was still observed, though less markedly than before. Unexpectedly and surprisingly, both the wild type and double mutant enzyme preparations derived from *T. reesei* were determined to be considerably more stable than the *E. coli* derived enzymes.

Figure 23A:
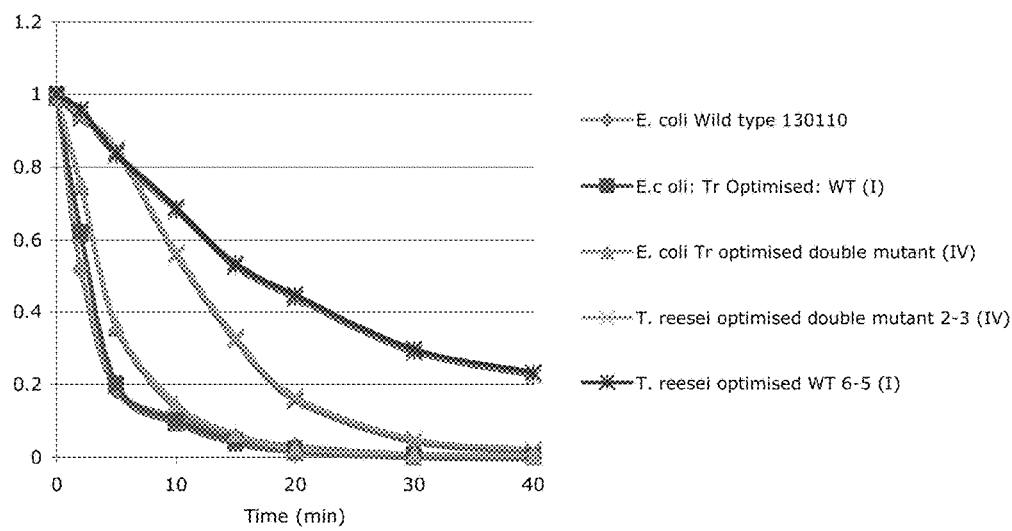
FIGS. 23A-B show the extended half-life of DtManA expressed in T. reesei versus *E. coli*.
Figure 23B:
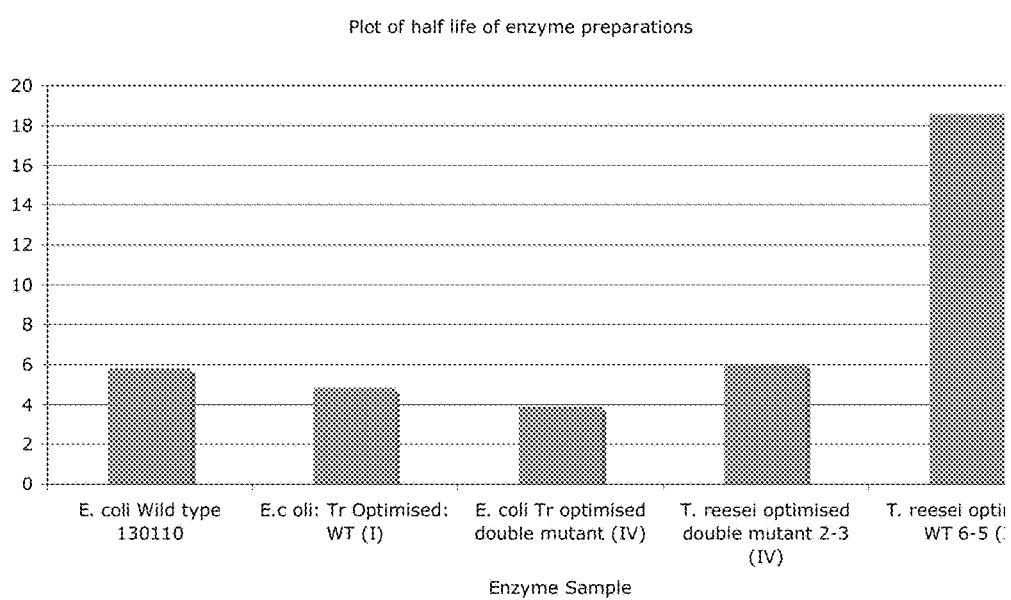

FIG. 23A shows a normalised plot of mannanase quantitation using a PAHBAH (p-Hydroxy benzoic acid hydrazide) reducing sugars assay. Under alkaline conditions 4-hydroxybenzoic acid hydrazide reacts with reducing saccharide to give intensively yellow anion which adsorbs strongly at 410 nm (Lever M. "A new reaction for the colorimetric determination of carbohydrates" *Anal. Biochem.* 47 (1972) 273-279.). From the PAHBAH results, the calculated half-lives of *E. coli* and *T. reesei* DtManA preparations are shown in FIG. 23B. As shown, the *T. reesei* expressed enzyme is 3× more stable than the *E. coli* expressed enzyme.

Improving Specific Activity by Modifying the Mannan-Binding Ability of *D. thermophilum* Mannanase by Mutation or Truncation Efforts were undertaken by site-directed mutagenesis to improve the *D. thermophilum* mannanase properties in breaking guar. First, presumed mannose binding sites were identified by alignment for mannanase-associated CBMs homologous to the CBM present at the N-terminal for DtManAFL (FL=full-length). In most cases, the CBM domains were observed to occur as N-terminal domains associated with family 26 GH's.

Overall, the CBMs domain showed fairly low sequence conservation (which is typical of CBMs in general), although a number of highly conserved residue positions were observed. The CBMs share weak homology with family 6 and family 35 CBMs. Examples of both families have had their structure solved, and the residues involved in binding identified. Unfortunately, the low sequence conservation between the mannanase associated CBMs with solved structures makes it difficult to determine whether the residues involved in binding in characterized examples is the same as residues in the CBM of DtManAFL.

However, after scanning the known structures of family 6 CBMs (none of which bind mannan), it became clear that the DtManA CBM has greater similarity to examples of family 35 CBMs, in particular the CBM35 from *Cellvibrio japonicus* Man5C, for which the structure has been solved. The key residues involved in binding by the Man5C CBM are also perfectly conserved in the CBM of DtManAFL, strongly implying that this CBM binds mannan using the same key residues. The key residues are a perfectly conserved lysine (Native DtManA CBM residue 68 on FIG. 25), and the motif WgW (tryptophan residues 113 & 115) which lies in the E-loop region defined by Wade Abbott (2009). The lysine at 68 FIG. 25 was mutated to an arginine (K→R) in the hope that it may still possess some binding activity, the tryptophans at 113 and 115 on FIG. 25 were mutated to leucines (W→L) in order to reduce or remove binding activity.

It was found that mutagenesis of any of these 3 key residues involved in substrate binding of the DtManA CBM reduced or removed the ability of DtManA full-length to bind to mannan (as assessed by diffusion in a plate-based overlay). Site-directed mutagenesis of any of the 3 selected amino acid residues within the CBM of DtManA substantially increased the specific activity (4-7.5 fold) of the full length mannanase in viscosity-breaking assays using guar as substrate at 60° C., pH 9.4.

Site-directed mutagenesis of the CBM of DtManA increased the relative activity of the full-length enzyme by around 2-3 when assessed by reducing sugar assay at 82° C., pH 6.2. Site directed mutagenesis increased the relative activity of the full-length DtManA by around 4-6 when assessed by viscosity assay at 22° C., pH 6.2. However, the mutants tested were not as stable at the wild-type enzyme at alkaline pH (they are functional at 60° C. pH 9.4, but not at 70° C. pH 9.4).

It was also found that a truncated form of DtManA lacking the CBM domain was 15-20 fold more active than the full-length form when assessed by reducing sugar assay at 82° C., pH 6.2. Thus, the CBM domain of DtManA contributes to the lower activity of the full-length form compared to the catalytic domain only and, whether by mutation of the CBM domain to inhibit mannan binding or by truncation eliminating the domain, the catalytic domain is considerably more active in the absence of a CBM domain that is able to fully bind mannose.

Results indicate the full-length enzyme may have a processive exo-mannanase activity conferred by the CBM domain, as removal of the binding function increases the specific activity of the enzyme to a greater degree in viscosity assays compared to reducing sugar assays.

The Relative Activity of the Truncated Vs Full Length Forms of DtManA

A method called limited proteolysis was used to convert the full-length component of DtManA, derived from *T. reesei*. The undigested enzyme preparation (derived from heat treated *T. reesei* culture supernatant) contained around 90% of the full-length form and 10% of the truncated form.

Figure 22A:
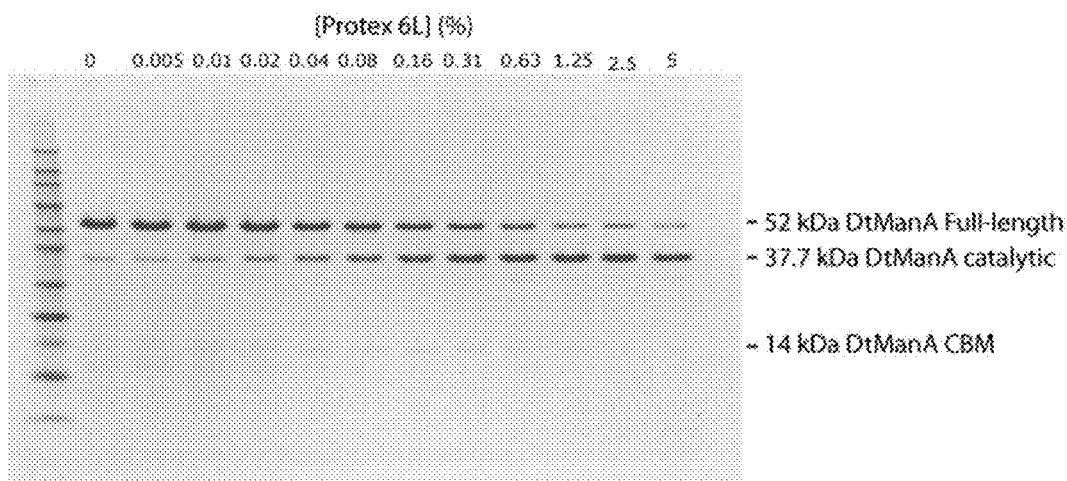
FIGS. 22A-B show proteolytic degradation of DtManA from full-length into a truncated form lacking the CBD.
Figure 22B:
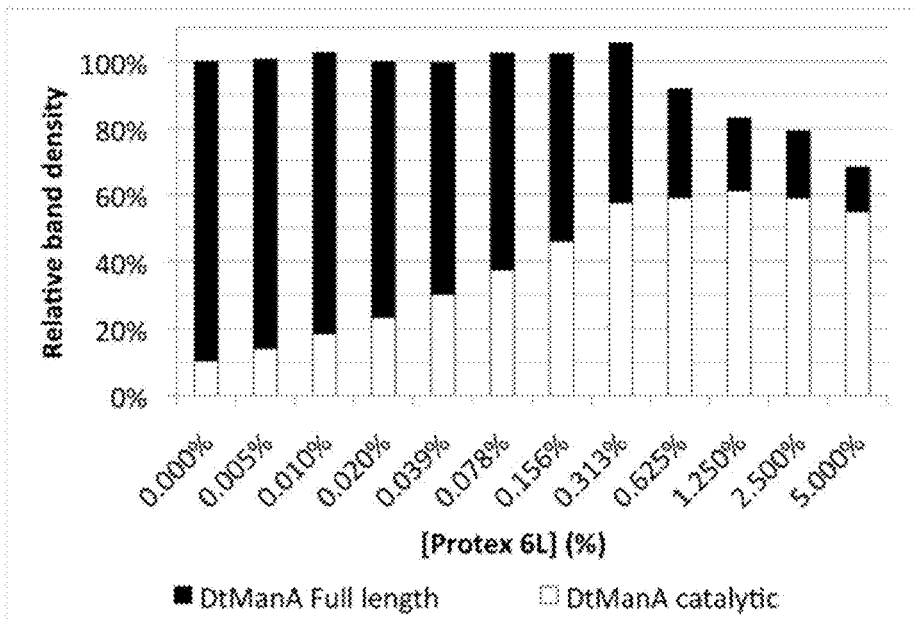

In brief, DtManA was mixed 1:1 with decreasing concentrations of the proteinase Protex 6L, incubated 20 minutes at 50° C., then heated to 80° C. for 10 minutes to inactivate the proteinase. SDS-PAGE and densitometry was then used to estimate the relative amounts of the full length and truncated forms (see FIGS. 22A and 22B). Beyond a Protex 6L concentration of 0.313%, the total mannanase concentration (combined full length and truncated forms) decreased, indicating overdigestion by the proteinase, and inactivation and loss of truncated mannanase. The mannanase activity present in each proteinase-digested sample was then analysed by PAHBAH reducing sugar assay. When the concentration of the truncated form was plotted against activity, a close to linear increase in mannanase activity was observed, indicating that the truncated form was the major contributor to the total activity.

If the linear curve is extrapolated back to the Y-axis, where the concentration of the truncated form equals zero, then we can estimate the contribution of activity by the full-length domain if it were 100% of the total mannanase. Based upon the extrapolation, the catalytic domain only form has around 19-34 fold higher activity compared to the full-length enzyme.

Guar Breakers Including Mixtures of DtManA Forms.

The relative activities of the full length DtManA and mutated or truncated forms of DtManA that lack a native DTManA CBM domain can be exploited to generate improved guar breaker solutions depending on the desired break profile for a given frac job. The full-length protein has greater activity at pH 9.6 and 80° C., whereas the truncated form has greater activity at pH 6.2 and 70° C. It appears that the truncated form is inherently more active, but when compared to the full-length protein it has lower stability at the high pH/high temperature conditions. In one embodiment, a mixture is provided that includes about 60-90% full-length to about 40-10% mutated or truncated forms of DtManA that lack a native DtManA CBM domain is generated. In another embodiment, a mixture is provided that includes about 90% full length to about 10% mutated or truncated forms of DtManA that lack a native DtManA CBM domain.

This mixture is particularly useful because of the desired enzyme activities at different stages of a fracturing process. It was surprisingly found that there appears to be a two-phase breakage of guar in HPHT tests (82° C.), with an initial rapid break in the first 20 minutes, followed by a slower break to completion. The initial fast break corresponds to the time required for the gel to heat to 82° C. This result is thought to be due to an initial contribution by the highly-active truncated form, which is lost due to thermal denaturation as the temperature approaches 80° C. The remainder of the break is performed by the remaining full-length form.

This two-phase breakage is exploited to maximize utility during a fracturing process. At ambient temperature when the frac fluid is made up-hole neither the truncated or the full-length DtManA will be active and the cross-linked guar will provide maximum viscosity and ability to suspend proppants. No degradation of the guar is desired until the proppant is delivered into the fractured formation. As the frac fluid is heated by the downhole formation the enzymes become active. In one embodiment, the mutated or truncated form of DtManA that lacks a native DtManA CBM domain is included because this form acts very fast and provides a level of early breaking such that the pumping can be continued with less friction pressure and excessive pressure build up. Ultimately, because it is less stable and has a shorter half-life, the mutated or truncated form of DtManA that lacks a native DtManA CBM domain is denatured and ceases to function. However, the full-length form will remain active and will continue breaking the cross-linked guar at temperatures up to 275° F. for prolonged periods.

The activities of the two forms of the enzyme can be seen in FIG. 17 where the mixture of enzymes is approximately 90% full length and 10% truncated. The rapid initial breaking is due to the activity of the truncated form of DtManA that lacks a native DTManA CBM domain. As this form becomes denatured, the kinetics of the reaction changes and the prolonged stable activity of the full length form is apparent.

Depending on the desired break profile for a given frac job or type of frac job, the relative ratios can be adjusted between the full-length and the mutated or truncated form of DtManA that lacks a native DtManA CBM domain.

Dry Powder Formulations

In one embodiment a storage stable dry powder includes at least one beta-mannanase obtained from a thermophilic bacteria such as *D. thermophilum* or *D. turgidus*. The dry powder enzyme is generated as a partially purified fermentation product as previously disclosed herein. The partially purified fermentation product is dried into a powder by any of a number of methods including rotational evaporation and spray drying.

In one exemplary embodiment, DtManA was produced in *T. reesei* as a highly expressed extracellular secretion product into the fermentation broth as previously discussed. The fermentation broth was heated to denature native *T. reesei* proteins and the denatured proteins removed by centrifugation yielding a relatively high concentration of partially purified DtManA in liquid solution. The pH of the liquid enzyme was adjusted to approximately 7.0 with KOH and microcrystalline cellulose (MCC) was added at a ratio of 1 lb. of MCC to 5 gallons of liquid enzyme. This mixture was divided into two parts for two different dryer settings and run through a pulse combustion spray dryer. The MCC was added to keep the enzyme dry (less than 6% moisture content) and free flowing. In one embodiment the pulse combustion spray drying was run to an exit temperature of 200° F., which yielded a moisture content of 4.9%. In another embodiment the pulse combustion spray drying was run to an exit temperature of 180° F., which yielded a moisture of 5.5%.

Typical guar slurries consist of a hydrophobic liquid solvent base (non-limiting examples include mineral oil and any other green/environmentally friendly oil such as a low viscosity vegetable oil), suspending agent(s) (such as an organophilic clay), dispersant(s), and thinning agent(s). For "green" frac fluids, a suitable dispersant could include either an ethoxylated linear alcohol or a fatty acid ester derived from a vegetable oil or animal oil.

Figure 26:
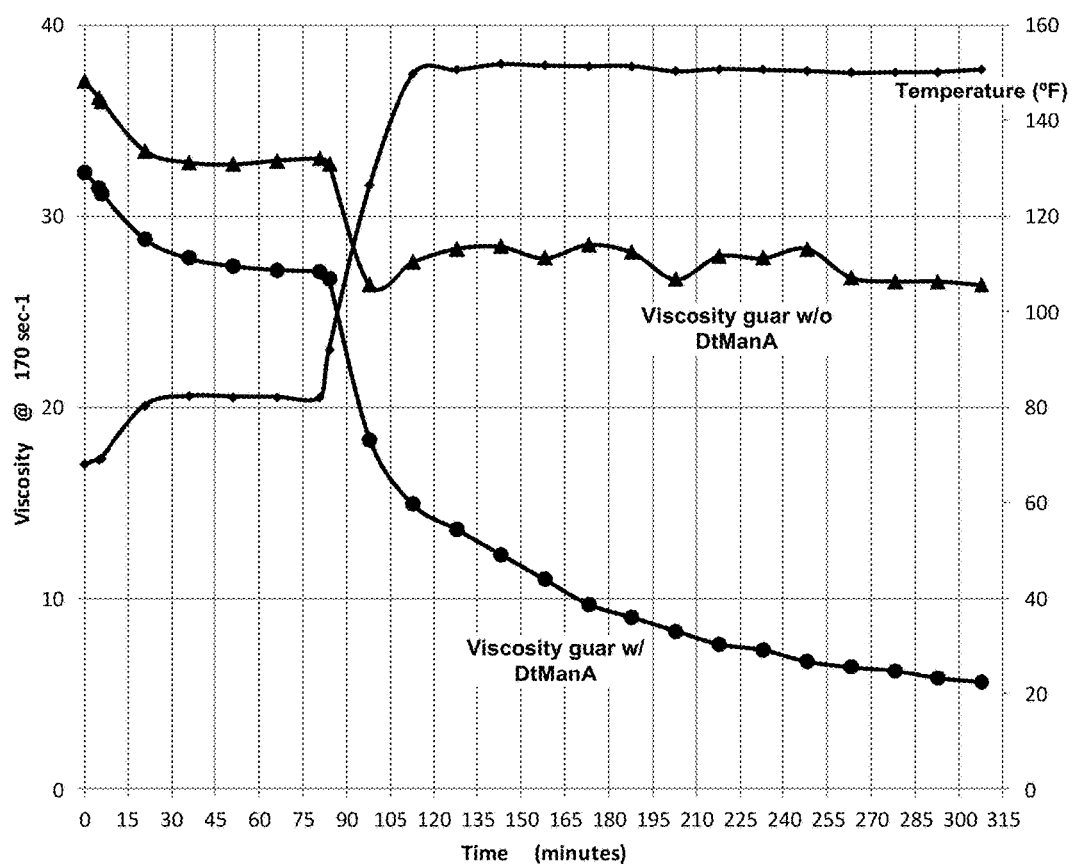
FIG. 26 shows the activity of dry powder DtManA on guar breaking as measured by decrease in viscosity.

The dry powder version of the DtManA was tested for activity by addition to a guar slurry and the enzyme was determined to be active and perform similarly to the liquid version. That is, as shown in FIG. 26, the dry powder DtManA becomes minimally active at over 80° F. and continues to be more active to reduce the viscosity of the guar at over 130° F. for a prolonged period. In addition to the viscosity study shown, regain permeability studies were conducted on 6 inch core plugs subject to guar gel flow for 49 minutes with a 16 hour shut-in followed by flow of choline chloride brine flowed in the production direction. The tests were run with guar gel either with or without the dry powder DtManA breaker. The tests were conducted at a 1000 psig overburden pressure by measuring differential pressure, leak-off volume, pore volume, permeability to air and porosity. Differential pressure beginning at 1000 psig was reduced to 10 psig by 200 minutes at which time maximal leak-off volume was obtained. Importantly, in certain tests the addition of the dry powder DtManA resulted in a % increase in regain permeability of from 36.4 to 41% compared to the permeability without added breaker.

In use, the concentration of the dry enzyme can be varied to achieve any desired degradation profile depending on the needs of the formation. In one embodiment, dry enzyme is added at approximately 2 lbs per 10,000 of guar slurry, wherein of the two lbs, the ratio of dry enzyme to MCC was 1:1.

The value of the dry powder version of the DtManA is realized by virtue of the temperature activity profile of DtManA. As it will be used in the field, the DtManA dry powder breaker is storage stable until use. When used, the dry powder breaker is added to the guar slurry uphole as the guar is mixed with various other additives potentially including biocides or disinfectants, scale inhibitor(s), iron control/stabilizing agents such as citric acid or hydrochloric acid, friction reducing agents, corrosion inhibitors, oxygen scavengers, and cross-linking agents such boric acid or ethylene glycol.

Typically, when cross-linking additives are added, prior art breakers have to be added later in the frac stages to cause the enhanced gelling agent to break down into a simpler fluid so it can be readily removed from the wellbore without carrying back the sand/proppant material. Addition of prior art breakers at the beginning of the frac would cause premature breaking the guar such that the desired maximum fluid integrity could not be obtained resulting in reduced proppant suspension and could lead to screen out.

Herein lies a particular advantage of the DtManA breaker in that it can be added with the guar at an early stage and will not begin breaking the guar until the guar is heated by the formation. With the DtManA disclosed herein, the breaker can be added to all stages without compromising the integrity of the fluid and will ultimately provide a controlled degradation or viscosity reduction during the entire frac job. Once the enzyme has degraded the crosslinked gel to a water-like viscosity, flowback can be started without carrying back the sand/proppant material, leaving an optimized proppant pack (with little or no proppant pack damage) and regained formation permeability.

Submitted with filing of this application by EFS is an ASCII text file including a sequence listing of the sequence disclosed herein. The file is named SEQ_ST25, is 55 kb and was created on Nov. 25, 2014. The material in the SEQ_ST25 text file is incorporated herein by reference.

We claim:

1. A method of generating commercial quantities of an enzyme for breaking guar based polymer gels that comprise beta-(1,4) mannosidic linkages, the method comprising:
transforming a population of exogenous host cells with a mixture of different expression cassettes, each expression cassette encoding a hyperthermophilic *Dictyoglomus* beta-mannanase enzyme (DtManA), the mixture comprising an expression cassette that encodes a full-length DtManA having at least 94% amino acid sequence identity with a native DtManA of SEQ ID NO: 1 or SEQ ID NO: 2 and an expression cassette that encodes a truncated or mutated DtManA that is derived from the full-length DtManA having at least 94% amino acid sequence identity with a native DtManA of SEQ ID NO: 1 or SEQ ID NO: 2 but lacks a native DtManA Carbohydrate Binding Module (CBM) domain and has a higher catalytic activity level at pH 6.2 and 70° C. and a lower stability at high pH/high temperature conditions as compared to the full-length DtManA;
culturing the transformed exogenous host cells in batch, fed batch or continuous fermentation; preparing a cell free supernatant containing the DtManA from the fermentation; and partially purifying the DtManA from the cell free supernatant by heat treatment at 70° C. or higher and removal of heat denatured proteins,
wherein the partially purified DtManA is provided as an enzyme breaker additive to a guar based polymer gel for downhole fracking in high temperature applications.

2. The method of claim 1, wherein the DtManA is an enzyme derived from a *Dictyoglomus* specie selected from one or more of a *Dictyoglomus thermophilum* and a *Dictyoglomus turgidum*.

3. The method of claim 1, wherein the polymer gel is cross-linked with a metal ion.

4. The method of claim 1, wherein the mixture of hyperthermophilic DtManAs are encoded by nucleic acids sequences that are codon optimized for expression in the exogenous host cells.

5. The method of claim 4, wherein the exogenous host cells are an *E. coli* species.

6. The method of claim 4, wherein the exogenous host cells are a *T. reesei* species.

7. The method of claim 1, wherein the truncated or mutated hyperthermophilic DtManA is stable at a pH range between 9 and 12 and has an optimum catalytic activity in a pH range between pH 6 and 8.

8. The method of claim 1, wherein the truncated or mutated hyperthermophilic DtManA is stable at a temperature range of 40° F. to and in excess of 270° F. and has an optimum catalytic activity in a temperature range in excess of 180° F.

9. The method of claim 1, wherein the full length DtManA comprises the native *Dictyoglomus thermophilum* DtManA amino acid sequence of SEQ ID NO: 1.

10. The method of claim 1, wherein the full length DtManA comprises the native *Dictyoglomus turgidum* DtManA amino acid sequence of SEQ ID NO: 2.

11. The method of claim 1, wherein the full length DtManA and the truncated or mutated DtManA each comprise a native *Dictyoglomus thermophilum* DtManA glycosyl hydrolase catalytic region of SEQ ID NO: 3.

12. The method of claim 1, wherein the truncated or mutated DtManA comprises an amino terminal truncation and lacks an N1 sequence of SEQ ID NO: 22.

13. The method of claim 5, wherein the codon optimized nucleic acid sequence for the full length DtManA is set forth in SEQ ID NO: 28.

14. The method of claim 6, wherein the codon optimized nucleic acid sequence for the full length DtManA is set forth in SEQ ID NO: 31.

15. The method of claim 1, wherein the expression cassette includes a secretion signal that drives extracellular secretion of the enzyme from the exogenous host cells.

16. The method of claim 15, wherein the exogenous host cells are *T. reesei* cells and the expression cassette includes a CBH1 promoter and signal sequence.

17. The method of claim 1, wherein the CBM domain of the truncated or mutated DtManA is mutated to reduce or abolish mannan binding by amino acid substitution at one or more key residues for mannan binding in the CBM domain.

18. The method of claim 17, wherein the key residues are selected from the group consisting of one or more of: lysine at residue 68 of SEQ ID NO: 42; tryptophan at residue 113 of SEQ ID NO: 42; and tryptophan at residue 115 of SEQ ID NO: 42.

19. The method of claim 1, wherein the truncated or mutated DtManA lacks one or both of native DtManA CBM sequence N1 of SEQ ID NO: 22, and native DtManA CBM sequence N2 of SEQ ID NO: 23.

20. The method of claim 19, wherein the mixture of expression cassettes produces about 60-90% of the full-length DtManA and about 10-40% of the mutated or truncated DtManA.

21. The method of claim 1, wherein the truncated or mutated DtManA comprises a mutation of arginine to lysine at residue 66 of the CBM domain set out in SEQ ID NO: 42.

22. The method of claim 18, wherein the amino acid substitutions are selected from the group consisting of one or more of: lysine to arginine at residue 68 of SEQ ID NO: 42; tryptophan to leucine at residue 113 of SEQ ID NO: 42; and tryptophan to leucine at residue 115 of SEQ ID NO: 42.

23. The method of claim 17, wherein the amino acid sequence of the CBM domain of the truncated or mutated DtManA is represented by SEQ ID NO: 42.

24. The method of claim 12, wherein the truncated DtManA is a 398 amino acid protein that has a 97% amino acid sequence identity with the truncated DtManA of SEQ ID NO: 30.

25. A method of generating commercial quantities of an enzyme for breaking guar based polymer gels that comprise beta-(1,4) mannosidic linkages, the method comprising:
transforming a population of exogenous host cells with an expression cassette encoding a recombinant mutated hyperthermophilic *Dictyoglomus* beta-mannanase enzyme (DtManA) comprising a Carbohydrate Binding Module (CBM) domain having 88% amino acid sequence identity with a native DtManA CBM of SEQ ID NO: 21, a catalytic domain having 97% amino acid sequence identity with a native DtManA catalytic domain of SEQ ID NO: 3, and an additional reiterated sequence KLVTPNPSKEAQKL as referenced by SEQ. ID. NO: 25 at a beginning of the catalytic domain;
culturing the transformed exogenous host cells in batch, fed batch or continuous fermentation;
preparing a cell free supernatant containing the DtManA from the fermentation; and
partially purifying the DtManA from the cell free supernatant by heat treatment at 70° C. or higher and removal of heat denatured proteins, wherein the partially purified DtManA is provided as an enzyme breaker additive to a guar based polymer gel for downhole fracking in high temperature applications.

26. The method of claim 25, wherein the recombinant mutated DtManA has an amino acid sequence represented by SEQ. ID. NO: 24.

* * * * *

SEQUENCE LISTING

<160> NUMBER OF SEQ ID NOS: 42

<210> SEQ ID NO 1
<211> LENGTH: 454
<212> TYPE: PRT
<213> ORGANISM: Dictyoglomus thermophilum

<400> SEQUENCE: 1

Ser Ile Asn Phe Ser Ser Asp Glu Ile Thr Ile Glu Ala Glu Asn Gly
1               5                   10                  15

Val Leu Asn Gly Thr Tyr Val Ala Arg Gln Phe Pro Gly Tyr Gln Gly
            20                  25                  30

Thr Gly Tyr Val Asp Gly Phe Asp Lys Asp Gly Asp Ser Cys Ser Val

```
            35                  40                  45
Thr Phe Glu Val Lys Glu Ser Gly Met Tyr Glu Leu Ile Ile Gly Tyr
 50                  55                  60

Ala Ala Pro Tyr Gly Tyr Lys Glu Asn Ser Leu Tyr Val Asn Gly Glu
65                  70                  75                  80

Phe Gln Thr Asn Val Lys Phe Pro Gln Ser Gln Lys Phe Thr Thr Val
                 85                  90                  95

Tyr Ala Gly Leu Ile Pro Leu Lys Asn Gly Lys Asn Thr Ile Ser Ile
                100                 105                 110

Val Lys Ser Trp Gly Trp Phe Leu Leu Asp Tyr Phe Lys Ile Lys Lys
            115                 120                 125

Ala Glu Ile Pro Thr Met Asn Pro Thr Asn Lys Leu Val Thr Pro Asn
            130                 135                 140

Pro Ser Lys Glu Ala Gln Lys Leu Met Asp Tyr Leu Val Ser Ile Tyr
145                 150                 155                 160

Gly Lys Tyr Thr Leu Ser Gly Gln Met Gly Tyr Lys Asp Ala Phe Trp
                165                 170                 175

Ile Trp Asn Ile Thr Asp Lys Phe Pro Ala Ile Cys Gly Phe Asp Met
                180                 185                 190

Met Asp Tyr Ser Pro Ser Arg Val Glu Arg Gly Ala Ser Ser Arg Asp
            195                 200                 205

Val Glu Asp Ala Ile Asp Trp Trp Asn Met Gly Gly Ile Val Gln Phe
210                 215                 220

Gln Trp His Trp Asn Ala Pro Lys Gly Leu Tyr Asp Thr Pro Gly Lys
225                 230                 235                 240

Glu Trp Trp Arg Gly Phe Tyr Thr Asn Ala Thr Ser Phe Asp Ile Glu
                245                 250                 255

Tyr Ala Phe Asn His Pro Glu Ser Glu Asp Tyr Lys Leu Ile Ile Arg
                260                 265                 270

Asp Ile Asp Ala Ile Ala Val Gln Leu Lys Arg Leu Gln Glu Ala Lys
            275                 280                 285

Val Pro Ile Leu Trp Arg Pro Leu His Glu Ala Glu Gly Arg Trp Phe
290                 295                 300

Trp Trp Gly Ala Lys Gly Pro Glu Ala Cys Lys Lys Leu Trp Arg Leu
305                 310                 315                 320

Leu Phe Asp Arg Leu Val Asn Tyr His Lys Ile Asn Asn Leu Ile Trp
                325                 330                 335

Val Trp Thr Thr Thr Asp Ser Pro Asp Ala Leu Lys Trp Tyr Pro Gly
                340                 345                 350

Asp Glu Tyr Val Asp Ile Val Gly Ala Asp Ile Tyr Leu Lys Asp Lys
            355                 360                 365

Asp Tyr Ser Pro Ser Thr Gly Met Phe Tyr Asn Ile Val Lys Leu Phe
            370                 375                 380

Gly Gly Lys Lys Leu Val Ala Leu Thr Glu Asn Gly Ile Ile Pro Asp
385                 390                 395                 400

Pro Asp Leu Met Lys Glu Gln Lys Ala Tyr Trp Val Trp Phe Met Thr
                405                 410                 415

Trp Ser Gly Phe Glu Asn Asp Pro Asn Lys Asn Glu Ile Ser His Ile
                420                 425                 430

Lys Lys Val Phe Asn His Pro Phe Val Ile Thr Lys Asp Glu Leu Pro
            435                 440                 445

Asn Leu Lys Val Glu Glu
            450
```

<210> SEQ ID NO 2
<211> LENGTH: 454
<212> TYPE: PRT
<213> ORGANISM: Dictyoglomus turgidum

<400> SEQUENCE: 2

```
Ser Leu Asn Phe Ser Thr Asp Glu Ile Val Val Glu Ala Glu Asn Gly
 1               5                  10                  15

Val Leu Asn Gly Thr Tyr Val Ala Lys Asn Leu Pro Gly Tyr Gln Gly
            20                  25                  30

Thr Gly Tyr Val Asp Gly Phe Asp Arg Asp Gly Asp Ser Cys Thr Ile
        35                  40                  45

Thr Phe Glu Val Lys Glu Ala Gly Met Tyr Glu Leu Ile Gly Tyr
    50                  55                  60

Ala Ala Pro Tyr Gly Tyr Lys Glu Asn Ser Leu Tyr Val Asn Gly Val
65                  70                  75                  80

Phe Gln Thr Asn Val Lys Phe Pro Pro Ser Gln Ser Phe Thr Thr Val
                85                  90                  95

Tyr Gly Gly Leu Ile Pro Leu Lys Ser Gly Lys Asn Thr Ile Ser Ile
            100                 105                 110

Val Lys Ser Trp Gly Trp Phe Leu Leu Asp Tyr Phe Lys Ile Lys Lys
        115                 120                 125

Ala Glu Leu Pro Thr Met Asn Pro Thr Asn Lys Leu Val Thr Pro Asn
    130                 135                 140

Pro Ser Lys Glu Ala Gln Lys Leu Met Asp Tyr Leu Val Ser Ile Tyr
145                 150                 155                 160

Gly Lys Tyr Thr Leu Ser Gly Gln Met Gly Tyr Lys Asp Ala Phe Trp
                165                 170                 175

Ile Trp Asn Ile Thr Asp Lys Phe Pro Ala Ile Cys Gly Phe Asp Met
            180                 185                 190

Ile Asp Tyr Ser Pro Ser Arg Val Glu Arg Gly Ala Ser Ser Arg Asp
        195                 200                 205

Val Glu Asp Ala Ile Asp Trp Trp Asn Met Gly Gly Ile Val Gln Phe
    210                 215                 220

Gln Trp His Trp Asn Ala Pro Lys Gly Leu Tyr Asp Thr Pro Gly Lys
225                 230                 235                 240

Glu Trp Trp Arg Gly Phe Tyr Thr Asn Ala Thr Ser Phe Asp Ile Glu
                245                 250                 255

Tyr Ala Leu Asn His Pro Glu Ser Glu Asp Tyr Lys Leu Ile Ile Arg
            260                 265                 270

Asp Ile Asp Ala Ile Ala Val Gln Leu Lys Arg Leu Gln Glu Ala Arg
        275                 280                 285

Val Pro Ile Leu Trp Arg Pro Leu His Glu Ala Glu Gly Arg Trp Phe
    290                 295                 300

Trp Trp Gly Ala Lys Gly Pro Glu Pro Cys Lys Lys Leu Trp Arg Leu
305                 310                 315                 320

Leu Phe Asp Arg Leu Val Asn Tyr His Lys Ile Asn Asn Leu Ile Trp
                325                 330                 335

Val Trp Thr Thr Thr Asp Ser Pro Asp Ala Leu Lys Trp Tyr Pro Gly
            340                 345                 350

Asp Glu Tyr Val Asp Ile Val Gly Ala Asp Val Tyr Leu Asn Asp Lys
        355                 360                 365

Asn Tyr Ser Pro Ser Thr Gly Met Phe Tyr Asn Ile Val Lys Ile Phe
```

```
                370                 375                 380
Gly Gly Lys Lys Leu Val Ala Leu Thr Glu Asn Gly Ile Ile Pro Asp
385                 390                 395                 400

Pro Asp Leu Met Lys Glu Gln Lys Ala Tyr Trp Ala Trp Phe Met Thr
                405                 410                 415

Trp Ser Gly Phe Glu Asn Asp Pro Asn Lys Asn Glu Ile Ser His Ile
                420                 425                 430

Lys Lys Val Phe Asn His Pro Phe Val Ile Thr Lys Asp Glu Leu Pro
                435                 440                 445

Asn Leu Lys Val Glu Glu
450

<210> SEQ ID NO 3
<211> LENGTH: 316
<212> TYPE: PRT
<213> ORGANISM: Dictyoglomus thermophilum

<400> SEQUENCE: 3

Lys Leu Val Thr Pro Asn Pro Ser Lys Glu Ala Gln Lys Leu Met Asp
1               5                   10                  15

Tyr Leu Val Ser Ile Tyr Gly Lys Tyr Thr Leu Ser Gly Gln Met Gly
                20                  25                  30

Tyr Lys Asp Ala Phe Trp Ile Trp Asn Ile Thr Asp Lys Phe Pro Ala
            35                  40                  45

Ile Cys Gly Phe Asp Met Met Asp Tyr Ser Pro Ser Arg Val Glu Arg
        50                  55                  60

Gly Ala Ser Ser Arg Asp Val Glu Asp Ala Ile Asp Trp Trp Asn Met
65                  70                  75                  80

Gly Gly Ile Val Gln Phe Gln Trp His Trp Asn Ala Pro Lys Gly Leu
                85                  90                  95

Tyr Asp Thr Pro Gly Lys Glu Trp Trp Arg Gly Phe Tyr Thr Asn Ala
            100                 105                 110

Thr Ser Phe Asp Ile Glu Tyr Ala Phe Asn His Pro Glu Ser Glu Asp
        115                 120                 125

Tyr Lys Leu Ile Ile Arg Asp Ile Asp Ala Ile Ala Val Gln Leu Lys
130                 135                 140

Arg Leu Gln Glu Ala Lys Val Pro Ile Leu Trp Arg Pro Leu His Glu
145                 150                 155                 160

Ala Glu Gly Arg Trp Phe Trp Trp Gly Ala Lys Gly Pro Glu Ala Cys
                165                 170                 175

Lys Lys Leu Trp Arg Leu Leu Phe Asp Arg Leu Val Asn Tyr His Lys
            180                 185                 190

Ile Asn Asn Leu Ile Trp Val Trp Thr Thr Thr Asp Ser Pro Asp Ala
        195                 200                 205

Leu Lys Trp Tyr Pro Gly Asp Glu Tyr Val Asp Ile Val Gly Ala Asp
210                 215                 220

Ile Tyr Leu Lys Asp Lys Asp Tyr Ser Pro Ser Thr Gly Met Phe Tyr
225                 230                 235                 240

Asn Ile Val Lys Leu Phe Gly Gly Lys Lys Leu Val Ala Leu Thr Glu
                245                 250                 255

Asn Gly Ile Ile Pro Asp Pro Asp Leu Met Lys Glu Gln Lys Ala Tyr
            260                 265                 270

Trp Val Trp Phe Met Thr Trp Ser Gly Phe Glu Asn Asp Pro Asn Lys
        275                 280                 285
```

```
Asn Glu Ile Ser His Ile Lys Lys Val Phe Asn His Pro Phe Val Ile
        290                 295                 300

Thr Lys Asp Glu Leu Pro Asn Leu Lys Val Glu Glu
305                 310                 315

<210> SEQ ID NO 4
<211> LENGTH: 10
<212> TYPE: PRT
<213> ORGANISM: Dictyoglomus thermophilum

<400> SEQUENCE: 4

Tyr Thr Leu Ser Gly Gln Met Gly Tyr Lys
1               5                   10

<210> SEQ ID NO 5
<211> LENGTH: 10
<212> TYPE: PRT
<213> ORGANISM: Dictyoglomus thermophilum

<400> SEQUENCE: 5

Lys Phe Pro Ala Ile Cys Gly Phe Asp Met
1               5                   10

<210> SEQ ID NO 6
<211> LENGTH: 10
<212> TYPE: PRT
<213> ORGANISM: Dictyoglomus thermophilum

<400> SEQUENCE: 6

Gly Gly Ile Val Gln Phe Gln Trp His Trp
1               5                   10

<210> SEQ ID NO 7
<211> LENGTH: 10
<212> TYPE: PRT
<213> ORGANISM: Dictyoglomus thermophilum

<400> SEQUENCE: 7

Pro Leu His Glu Ala Glu Gly Arg Trp Phe
1               5                   10

<210> SEQ ID NO 8
<211> LENGTH: 10
<212> TYPE: PRT
<213> ORGANISM: Dictyoglomus thermophilum

<400> SEQUENCE: 8

Lys Leu Val Ala Leu Thr Glu Asn Gly Ile
1               5                   10

<210> SEQ ID NO 9
<211> LENGTH: 10
<212> TYPE: PRT
<213> ORGANISM: Dictyoglomus thermophilum

<400> SEQUENCE: 9

Asn Lys Asn Glu Ile Ser His Ile Lys Lys
1               5                   10

<210> SEQ ID NO 10
<211> LENGTH: 10
<212> TYPE: PRT
<213> ORGANISM: Dictyoglomus thermophilum

<400> SEQUENCE: 10
```

```
Asp Ala Phe Trp Ile Trp Asn Ile Thr Asp
1               5                   10

<210> SEQ ID NO 11
<211> LENGTH: 11
<212> TYPE: PRT
<213> ORGANISM: Dictyoglomus thermophilum

<400> SEQUENCE: 11

Asp Val Glu Asp Ala Ile Asp Trp Trp Asn Met
1               5                   10

<210> SEQ ID NO 12
<211> LENGTH: 17
<212> TYPE: PRT
<213> ORGANISM: Dictyoglomus thermophilum

<400> SEQUENCE: 12

Ser Glu Asp Tyr Lys Leu Ile Ile Arg Asp Ile Asp Ala Ile Ala Val
1               5                   10                  15

Gln

<210> SEQ ID NO 13
<211> LENGTH: 7
<212> TYPE: PRT
<213> ORGANISM: Dictyoglomus thermophilum

<400> SEQUENCE: 13

Asn Asn Leu Ile Trp Val Trp
1               5

<210> SEQ ID NO 14
<211> LENGTH: 8
<212> TYPE: PRT
<213> ORGANISM: Dictyoglomus thermophilum

<400> SEQUENCE: 14

Ile Val Gly Ala Asp Ile Tyr Leu
1               5

<210> SEQ ID NO 15
<211> LENGTH: 13
<212> TYPE: PRT
<213> ORGANISM: Dictyoglomus thermophilum

<400> SEQUENCE: 15

Ala Cys Lys Lys Leu Trp Arg Leu Leu Phe Asp Arg Leu
1               5                   10

<210> SEQ ID NO 16
<211> LENGTH: 6
<212> TYPE: PRT
<213> ORGANISM: Dictyoglomus thermophilum

<400> SEQUENCE: 16

Asp Ala Leu Lys Trp Tyr
1               5

<210> SEQ ID NO 17
<211> LENGTH: 12
<212> TYPE: PRT
<213> ORGANISM: Dictyoglomus thermophilum

<400> SEQUENCE: 17
```

```
Ser Thr Gly Met Phe Tyr Asn Ile Val Lys Leu Phe
1               5                   10

<210> SEQ ID NO 18
<211> LENGTH: 7
<212> TYPE: PRT
<213> ORGANISM: Dictyoglomus thermophilum

<400> SEQUENCE: 18

Trp Val Trp Phe Met Thr Trp
1               5

<210> SEQ ID NO 19
<211> LENGTH: 7
<212> TYPE: PRT
<213> ORGANISM: Dictyoglomus thermophilum

<400> SEQUENCE: 19

Asp Leu Met Lys Glu Gln Lys
1               5

<210> SEQ ID NO 20
<211> LENGTH: 8
<212> TYPE: PRT
<213> ORGANISM: Dictyoglomus thermophilum

<400> SEQUENCE: 20

Lys Glu Ala Gln Lys Leu Met Asp
1               5

<210> SEQ ID NO 21
<211> LENGTH: 124
<212> TYPE: PRT
<213> ORGANISM: Dictyoglomus thermophilum

<400> SEQUENCE: 21

Glu Ile Thr Ile Glu Ala Glu Asn Gly Val Leu Asn Gly Thr Tyr Val
1               5                   10                  15

Ala Arg Gln Phe Pro Gly Tyr Gln Gly Thr Gly Tyr Val Asp Gly Phe
                20                  25                  30

Asp Lys Asp Gly Asp Ser Cys Ser Val Thr Phe Glu Val Lys Glu Ser
            35                  40                  45

Gly Met Tyr Glu Leu Ile Ile Gly Tyr Ala Ala Pro Tyr Gly Tyr Lys
        50                  55                  60

Glu Asn Ser Leu Tyr Val Asn Gly Glu Phe Gln Thr Asn Val Lys Phe
65                  70                  75                  80

Pro Gln Ser Gln Lys Phe Thr Thr Val Tyr Ala Gly Leu Ile Pro Leu
                85                  90                  95

Lys Asn Gly Lys Asn Thr Ile Ser Ile Val Lys Ser Trp Gly Trp Phe
                100                 105                 110

Leu Leu Asp Tyr Phe Lys Ile Lys Lys Ala Glu Ile
            115                 120

<210> SEQ ID NO 22
<211> LENGTH: 10
<212> TYPE: PRT
<213> ORGANISM: Dictyoglomus thermophilum

<400> SEQUENCE: 22

Glu Ala Glu Asn Gly Val Leu Asn Gly Thr
1               5                   10
```

<210> SEQ ID NO 23
<211> LENGTH: 10
<212> TYPE: PRT
<213> ORGANISM: Dictyoglomus thermophilum

<400> SEQUENCE: 23

Trp Gly Trp Phe Leu Leu Asp Tyr Phe Lys
1               5                   10

<210> SEQ ID NO 24
<211> LENGTH: 457
<212> TYPE: PRT
<213> ORGANISM: artificial sequence
<220> FEATURE:
<223> OTHER INFORMATION: D. Thermophilium DtManA with reiterated
      sequence

<400> SEQUENCE: 24

Glu Ile Thr Ile Glu Ala Glu Asn Gly Val Leu Asn Gly Thr Tyr Val
1               5                   10                  15

Ala Arg Gln Phe Pro Gly Tyr Gln Gly Thr Gly Tyr Val Asp Gly Phe
                20                  25                  30

Asp Lys Asp Gly Asp Ser Cys Ser Val Thr Phe Glu Val Lys Glu Ser
            35                  40                  45

Gly Met Tyr Glu Leu Ile Ile Gly Tyr Ala Ala Pro Tyr Gly Tyr Lys
        50                  55                  60

Glu Asn Ser Leu Tyr Val Asn Gly Glu Phe Gln Thr Asn Val Lys Phe
65                  70                  75                  80

Pro Gln Ser Gln Lys Phe Thr Thr Val Tyr Ala Gly Leu Ile Pro Leu
                85                  90                  95

Lys Asn Gly Lys Asn Thr Ile Ser Ile Val Lys Ser Trp Gly Trp Phe
            100                 105                 110

Leu Leu Asp Tyr Phe Lys Ile Lys Lys Ala Glu Ile Pro Thr Asn Lys
        115                 120                 125

Leu Val Thr Pro Asn Pro Ser Lys Glu Ala Gln Lys Leu Lys Leu Val
    130                 135                 140

Thr Pro Asn Pro Ser Lys Glu Ala Gln Lys Leu Met Asp Tyr Leu Val
145                 150                 155                 160

Ser Ile Tyr Gly Lys Tyr Thr Leu Ser Gly Gln Met Gly Tyr Lys Asp
                165                 170                 175

Ala Phe Trp Ile Trp Asn Ile Thr Asp Lys Phe Pro Ala Ile Cys Gly
            180                 185                 190

Phe Asp Met Met Asp Tyr Ser Pro Ser Arg Val Glu Arg Gly Ala Ser
        195                 200                 205

Ser Arg Asp Val Glu Asp Ala Ile Asp Trp Asn Met Gly Gly Ile
    210                 215                 220

Val Gln Phe Gln Trp His Trp Asn Ala Pro Lys Gly Leu Tyr Asp Thr
225                 230                 235                 240

Pro Gly Lys Glu Trp Trp Arg Gly Phe Tyr Thr Asn Ala Thr Ser Phe
                245                 250                 255

Asp Ile Glu Tyr Ala Phe Asn His Pro Glu Ser Glu Tyr Lys Leu
            260                 265                 270

Ile Ile Arg Asp Ile Asp Ala Ile Ala Val Gln Leu Lys Arg Leu Gln
        275                 280                 285

Glu Ala Lys Val Pro Ile Leu Trp Arg Pro Leu His Glu Ala Glu Gly
    290                 295                 300

```
Arg Trp Phe Trp Trp Gly Ala Lys Gly Pro Glu Ala Cys Lys Lys Leu
305                 310                 315                 320

Trp Arg Leu Leu Phe Asp Arg Leu Val Asn Tyr His Lys Ile Asn Asn
                325                 330                 335

Leu Ile Trp Val Trp Thr Thr Thr Asp Ser Pro Asp Ala Leu Lys Trp
            340                 345                 350

Tyr Pro Gly Asp Glu Tyr Val Asp Ile Val Gly Ala Asp Ile Tyr Leu
        355                 360                 365

Lys Asp Lys Asp Tyr Ser Pro Ser Thr Gly Met Phe Tyr Asn Ile Val
    370                 375                 380

Lys Leu Phe Gly Gly Lys Lys Leu Val Ala Leu Thr Glu Asn Gly Ile
385                 390                 395                 400

Ile Pro Asp Pro Asp Leu Met Lys Glu Gln Lys Ala Tyr Trp Val Trp
                405                 410                 415

Phe Met Thr Trp Ser Gly Phe Glu Asn Asp Pro Asn Lys Asn Glu Ile
            420                 425                 430

Ser His Ile Lys Lys Val Phe Asn His Pro Phe Val Ile Thr Lys Asp
        435                 440                 445

Glu Leu Pro Asn Leu Lys Val Glu Glu
    450                 455

<210> SEQ ID NO 25
<211> LENGTH: 14
<212> TYPE: PRT
<213> ORGANISM: Dictyoglomus thermophilum

<400> SEQUENCE: 25

Lys Leu Val Thr Pro Asn Pro Ser Lys Glu Ala Gln Lys Leu
1               5                   10

<210> SEQ ID NO 26
<211> LENGTH: 951
<212> TYPE: DNA
<213> ORGANISM: Dictyoglomus thermophilum

<400> SEQUENCE: 26
aaattagtaa cccctaatcc atcaaaagag gcccaaaaat taatggacta tttagtgagt     60
atatatggaa agtatactct ctcgggtcag atgggatata agatgccttc tggatttgg    120 aatattactg ataagtttcc agctatatgt ggttttgaca tgatggacta ctcaccttca    180
agggttgaaa gaggagcatc ttcaagagat gtggaagatg ctatagattg gtggaatatg    240
ggaggaatag ttcaatttca atggcactgg aatgctccaa agggacttta tgatactcca    300
ggaaaagaat ggtggagagg ctttttacact aatgctacca gttttgatat agaatatgct    360
ttcaaccacc ctgaatctga agattacaaa cttataataa gggatataga tgctattgca    420
gtacaattaa aaagacttca gaggcaaaaa gtccccatac tatggagacc tttacacgag    480
gcagaaggta gatggttctg gtggggagca aaaggtcctg aagcttgtaa aaaactatgg    540
agactacttt ttgataggct tgtaaattat cataaaataa ataatcttat atgggtttgg    600
actactacag actctcctga tgctctcaaa tggtatcctg gagatgaata tgtagatatt    660
gtaggagcag atatatacct taagataaaa gattattctc catctacagg aatgttctat    720
aacattgtaa aactatttgg tgggaaaaaa ctcgtagctc tcacagaaaa tggaattatt    780
ccagatccag atttaatgaa agagcaaaaa gcttattggg tatggtttat gacctggtca    840
ggttttgaaa atgatccaaa caaaaacgaa atctctcata ttaaaaaagt atttaatcat    900
```

```
cccttttgtaa ttacaaaaga tgagctacca aatttgaaag ttgaagaata a              951
```

<210> SEQ ID NO 27
<211> LENGTH: 1347
<212> TYPE: DNA
<213> ORGANISM: Dictyoglomus thermophilum

<400> SEQUENCE: 27

```
atggaaatta ctattgaagc agaaaatggg gtattaaacg gaacctatgt agcaagacaa       60
tttcctggat atcaaggcac aggatatgtg gatggatttg ataaggatgg agattcttgt      120
agtgtaacttt tgaagtaaa ggagtctgga atgtacgaat taataattgg atatgctgca      180
ccctatggat ataaggaaaa ttcccttttat gtaaatggag aatttcaaac caatgtcaaa    240
tttccccaat ctcaaaaatt tacaaccgta tatgctggtt taattccttt aaaaaatgga     300
aaaaatacaa taagtatagt aaaaagctgg ggatggtttc ttcttgacta ctttaaaatc    360
aaaaaggcag aaattcctac catgaatcct acaaacaaat tagtaacccc taatccatca    420
aaagaggccc aaaaattaat ggactattta gtgagtatat atggaaagta tactctctcg    480
ggtcagatgg gatataaaga tgccttctgg atttggaata ttactgataa gtttccagct    540
atatgtggtt ttgacatgat ggactactca ccttcaaggg ttgaaagagg agcatcttca    600
agagatgtgg aagatgctat agattggtgg aatatgggag aatagttca atttcaatgg     660
cactggaatg ctccaaaggg actttatgat actccaggaa agaatggtg agagaggcttt    720
tacactaatg ctaccagttt tgatatagaa tatgctttca accaccctga atctgaagat    780
tacaaactta aataaggga tatagatgct attgcagtac aattaaaag acttcaagag     840
gcaaaagtcc ccatactatg gagacccttta cacgaggcag aaggtagatg gttctggtgg    900
ggagcaaaag gtcctgaagc ttgtaaaaaa ctatggagac tactttttga taggcttgta   960
aattatcata aaataaataa tcttatatgg gtttggacta ctacagactc tcctgatgct   1020
ctcaaatggt atcctggaga tgaatatgta gatattgtag gagcagatat ataccttaaa   1080
gataaagatt attctccatc tacaggaatg ttctataaca ttgtaaaact atttggtggg   1140
aaaaaactcg tagctctcac agaaaatgga attattccag atccagattt aatgaaagag   1200
caaaaagctt attgggtatg gtttatgacc tggtcaggtt ttgaaaatga tccaaacaaa   1260
aacgaaatct ctcatattaa aaagtatttt aatcatccct ttgtaattac aaaagatgag   1320
ctaccaaatt tgaaagttga agaataa                                        1347
```

<210> SEQ ID NO 28
<211> LENGTH: 1197
<212> TYPE: DNA
<213> ORGANISM: artificial sequence
<220> FEATURE:
<223> OTHER INFORMATION: codon optimization

<400> SEQUENCE: 28

```
atgcacgaac tgattattgg ttacgcagca ccgtatggct ataagaaaaa cagcctgtat       60
gtgaacggcg aatttcaaac gaacgtcaaa tttccgcagt cacaaaagtt caccacggtc     120
tacgcgggtc tgattccgct gaaaaacggc aagaatacca ttagcatcgt taatcttgg      180
ggttggttcc tgctggatta cttcaagatt aaaaaggccg aaatcccgac gatgaacccg    240
accaataaac tggtgacccc gaacccgtcc aaagaagcac agaagctgat ggattacctg    300
gttagcattt atggcaaata cacgctgtcc ggccaaatgg gttataagga cgcgttctgg    360
```

```
atctggaaca tcaccgataa gttcccggcc atctgcggtt tcgatatgat ggactacagt      420
ccgtcccgtg ttgaacgcgg cgcgagctct cgtgatgtcg aagacgccat tgattggtgg      480
aacatgggcg gtatcgtgca gtttcaatgg cattggaatg ccccgaaagg cctgtatgat      540
accccgggca aggaatggtg gcgcggcttt tatacgaacg caacctcatt cgacattgaa      600
tacgctctga atcacccgga atcggaagat tacaaactga tcatccgtga tatcgacgcg      660
atcgccgtcc agctgaaacg cctgcaagaa gcaaaggtgc cgatcctgtg cgtccgctg       720
catgaagctg aaggtcgctg gttttggtgg ggcgcaaaag gtccggaagc gtgcaaaaag      780
ctgtggcgtc tgctgttcga tcgcctggtt aactaccaca gatcaacaa cctgatctgg       840
gtctggacca cgaccgacag cccggatgcg ctgaaatggt atccgggtga cgaatacgtg      900
gatattgttg cgccgatat ctatctgaaa gataaggact actcaccgag caccggcatg       960
ttttacaaca ttgtgaaact gttcggcggt aaaaagctgg ttgcactgac cgaaaatggc     1020
attatcccgg acccgatct gatgaaagaa cagaaggctt attgggtgtg gtttatgacg      1080
tggagcggct tcgaaaatga cccgaacaag aacgaaattt ctcatatcaa aaaggtcttt     1140
aaccacccgt tcgtgattac caaagatgaa ctgccgaatc tgaaggttga agaataa       1197

<210> SEQ ID NO 29
<211> LENGTH: 1197
<212> TYPE: DNA
<213> ORGANISM: Dictyoglomus thermophilum

<400> SEQUENCE: 29
atgcacgaat taataattgg atatgctgca ccctatggat ataaggaaaa ttcccttttat      60
gtaaatggag aatttcaaac caatgtcaaa tttccccaat ctcaaaaatt tacaaccgta     120
tatgctggtt taattccttt aaaaaatgga aaaaatacaa taagtatagt aaaaagctgg     180
ggatggtttc ttcttgacta ctttaaaatc aaaaaggcag aaattcctac catgaatcct     240
acaaacaaat tagtaacccc taatccatca aaagaggccc aaaaattaat ggactattta     300
gtgagtatat atggaaagta tactctctcg ggtcagatgg gatataaaga tgccttctgg     360
atttggaata ttactgataa gtttccagct atatgtggtt ttgacatgat ggactactca     420
ccttcaaggg ttgaaagagg agcatcttca agagatgtgg aagatgctat agattggtgg     480
aatatgggag aatagttca atttcaatgg cactggaatg ctccaaaggg actttatgat      540
actccaggaa aagaatggtg gagaggcttt tacactaatg ctaccagttt tgatatagaa      600
tatgctctca accaccctga atctgaagat tacaaactta aataaggga tatagatgct      660
attgcagtac aattaaaaag acttcaagag gcaaaagtcc ccatactatg gagacccttta     720
cacgaggcag aaggtagatg gttctggtgg ggagcaaaag gtcctgaagc ttgtaaaaaa     780
ctatggagac tacttttttga taggcttgta aattatcata aaataaataa tcttatatgg      840
gtttggacta ctacagactc tcctgatgct ctcaaatggt atcctggaga tgaatatgta      900
gatattgtag gagcagatat ataccttaaa gataaagatt attctccatc tacaggaatg      960
ttctataaca ttgtaaaact atttggtggg aaaaaactcg tagctctcac agaaaatgga     1020
attattccag atccagattt aatgaaagag caaaaagctt attgggtatg gtttatgacc     1080
tggtcaggtt ttgaaaatga tccaaacaaa aacgaaatct ctcatattaa aaagtatttt     1140
aatcatccct ttgtaattac aaaagatgag ctaccaaact tgaaagttga agaataa       1197

<210> SEQ ID NO 30
<211> LENGTH: 398
```

<212> TYPE: PRT
<213> ORGANISM: Dictyoglomus thermophilum

<400> SEQUENCE: 30

```
Met His Glu Leu Ile Ile Gly Tyr Ala Ala Pro Tyr Gly Tyr Lys Glu
1               5                   10                  15

Asn Ser Leu Tyr Val Asn Gly Glu Phe Gln Thr Asn Val Lys Phe Pro
            20                  25                  30

Gln Ser Gln Lys Phe Thr Thr Val Tyr Ala Gly Leu Ile Pro Leu Lys
        35                  40                  45

Asn Gly Lys Asn Thr Ile Ser Ile Val Lys Ser Trp Gly Trp Phe Leu
    50                  55                  60

Leu Asp Tyr Phe Lys Ile Lys Lys Ala Glu Ile Pro Thr Met Asn Pro
65                  70                  75                  80

Thr Asn Lys Leu Val Thr Pro Asn Pro Ser Lys Glu Ala Gln Lys Leu
                85                  90                  95

Met Asp Tyr Leu Val Ser Ile Tyr Gly Lys Tyr Thr Leu Ser Gly Gln
            100                 105                 110

Met Gly Tyr Lys Asp Ala Phe Trp Ile Trp Asn Ile Thr Asp Lys Phe
        115                 120                 125

Pro Ala Ile Cys Gly Phe Asp Met Met Asp Tyr Ser Pro Ser Arg Val
    130                 135                 140

Glu Arg Gly Ala Ser Ser Arg Asp Val Glu Asp Ala Ile Asp Trp Trp
145                 150                 155                 160

Asn Met Gly Gly Ile Val Gln Phe Gln Trp His Trp Asn Ala Pro Lys
                165                 170                 175

Gly Leu Tyr Asp Thr Pro Gly Lys Glu Trp Trp Arg Gly Phe Tyr Thr
            180                 185                 190

Asn Ala Thr Ser Phe Asp Ile Glu Tyr Ala Leu Asn His Pro Glu Ser
        195                 200                 205

Glu Asp Tyr Lys Leu Ile Ile Arg Asp Ile Asp Ala Ile Ala Val Gln
    210                 215                 220

Leu Lys Arg Leu Gln Glu Ala Lys Val Pro Ile Leu Trp Arg Pro Leu
225                 230                 235                 240

His Glu Ala Glu Gly Arg Trp Phe Trp Trp Gly Ala Lys Gly Pro Glu
                245                 250                 255

Ala Cys Lys Lys Leu Trp Arg Leu Leu Phe Asp Arg Leu Val Asn Tyr
            260                 265                 270

His Lys Ile Asn Asn Leu Ile Trp Val Trp Thr Thr Thr Asp Ser Pro
        275                 280                 285

Asp Ala Leu Lys Trp Tyr Pro Gly Asp Glu Tyr Val Asp Ile Val Gly
    290                 295                 300

Ala Asp Ile Tyr Leu Lys Asp Lys Asp Tyr Ser Pro Ser Thr Gly Met
305                 310                 315                 320

Phe Tyr Asn Ile Val Lys Leu Phe Gly Gly Lys Lys Leu Val Ala Leu
                325                 330                 335

Thr Glu Asn Gly Ile Ile Pro Asp Pro Asp Leu Met Lys Glu Gln Lys
            340                 345                 350

Ala Tyr Trp Val Trp Phe Met Thr Trp Ser Gly Phe Gly Asn Asp Pro
        355                 360                 365

Asn Lys Asn Glu Ile Ser His Ile Lys Lys Val Phe Asn His Pro Phe
    370                 375                 380

Val Ile Thr Lys Asp Glu Leu Pro Asn Leu Lys Val Glu Glu
385                 390                 395
```

<210> SEQ ID NO 31
<211> LENGTH: 1372
<212> TYPE: DNA
<213> ORGANISM: artificial sequence
<220> FEATURE:
<223> OTHER INFORMATION: codon optimized for expression in t. reesei

<400> SEQUENCE: 31

```
ccatggcaca cgtggagatc accatcgagg ccgagaacgg cgtcctcaac ggcacctacg      60
tcgctcgcca gtttcctggc tatcaaggca ctggctacgt cgatggcttc gacaaagacg     120
gcgatagctg ctccgtcacg ttcgaagtca aggagtccgg catgtacgaa cttatcattg     180
gctacgccgc accttacggt tacaaggaga actccctgta cgtcaacggc gagttccaga     240
ccaacgtcaa atttccacag tctcagaagt ttactactgt ctacgccggc ctgattcctc     300
tcaagaatgg taagaacacc atctccatcg tcaagtcctg gggatggttc ctcctggact     360
acttcaagat caagaaggcc gagattccca ccatgaaccc taccaacaaa ctcgtcacac     420
ccaacccatc caaggaggcc cagaagctca tggactacct cgtctctatc tacggcaagt     480
acaccctctc tggccagatg ggatacaagg atgccttctg gatctggaac atcaccgaca     540
aatttcccgc gatttgcgga ttcgatatga tggattactc gccctcgcgc gtcgaacgtg     600
gcgcctcctc ccgagacgtc gaagacgcca tcgactggtg gaacatgggc ggtatcgttc     660
agttccaatg gcactggaac gctcccaagg gtctgtatga taccctgga aaggagtggt     720
ggcgcggctt ctacactaac gctacctcct tgacattga gtacgcgttc aaccatcccg     780
agtccgagga ctacaaactc atcatcaggg acattgacgc gattgctgtc cagctcaaga     840
ggctgcaaga agctaaggtt ccgatcttgt ggagacctct tcacgaagcg agggtcgct     900
ggttctggtg gggagccaag ggcccagagg cgtgtaagaa gctttggcgt ctgttgtttg     960
accgcctggt gaactaccac aagatcaaca atttgatttg ggtgtggact acgactgaca    1020
gcccggacgc cctgaagtgg tatccgggtg atgaatacgt tgatatcgtg ggcgccgata    1080
tctatctgaa ggacaaggat tatagcccat cgacgggtat gttctacaac atcgtcaagc    1140
tcttcggtgg caagaagttg gttgctctga cagagaatgg cattatccct gacccggacc    1200
tgatgaagga gcagaaggcc tactgggtgt ggtttatgac ctggagcgga tttgagaacg    1260
acccgaacaa gaacgagatt tctcatatca agaaggtctt caaccaccca tttgtgatca    1320
cgaaggatga gcttccgaac ctgaaggttg aggagtaata gcttaagtcg ac            1372
```

<210> SEQ ID NO 32
<211> LENGTH: 1372
<212> TYPE: DNA
<213> ORGANISM: artificial sequence
<220> FEATURE:
<223> OTHER INFORMATION: codon optimized for expression in t. reesei

<400> SEQUENCE: 32

```
ggtaccgtgt gcacctctag tggtagctcc ggctcttgcc gcaggagttg ccgtggatgc      60
agcgagcggt caaaggaccg atagttccgt gaccgatgca gctaccgaag ctgtttctgc     120
cgctatcgac gaggcagtgc aagcttcagt tcctcaggcc gtacatgctt gaatagtaac     180
cgatgcggcg tggaatgcca atgttcctct tgagggacat gcagttgccg ctcaaggtct     240
ggttgcagtt taaaggtgtc agagtcttca aatgatgaca gatgcggccg gactaaggag     300
agttcttacc attcttgtgg tagaggtagc agttcaggac ccctaccaag gaggacctga     360
```

```
tgaagttcta gttcttccgg ctctaagggt ggtacttggg atggttgttt gagcagtgtg    420
ggttgggtag gttcctccgg gtcttcgagt acctgatgga gcagagatag atgccgttca    480
tgtgggagag accggtctac cctatgttcc tacggaagac ctagaccttg tagtggctgt    540
ttaaagggcg ctaaacgcct aagctatact acctaatgag cgggagcgcg cagcttgcac    600
cgcggaggag ggctctgcag cttctgcggt agctgaccac cttgtacccg ccatagcaag    660
tcaaggttac cgtgacctttg cgaggggttcc cagacatact atgggggacct ttcctcacca    720
ccgcgccgaa gatgtgattg cgatggagga aactgtaact catgcgcaag ttggtagggc    780
tcaggctcct gatgtttgag tagtagtccc tgtaactgcg ctaacgacag gtcgagttct    840
ccgacgttct tcgattccaa ggctagaaca cctctggaga agtgcttcgc ctcccagcga    900
ccaagaccac ccctcggttc ccgggtctcc gcacattctt cgaaaccgca gacaacaaac    960
tggcggacca cttgatggtg ttctagttgt taaactaaac ccacacctga tgctgactgt   1020
cgggcctgcg ggacttcacc ataggcccac tacttatgca actatagcac ccgcggctat   1080
agatagactt cctgttccta atatcgggta gctgcccata caagatgttg tagcagttcg   1140
agaagccacc gttcttcaac caacgagact gtctcttacc gtaatagggga ctgggcctgg   1200
actacttcct cgtcttccgg atgacccaca ccaaatactg gacctcgcct aaactcttgc   1260
tgggcttgtt cttgctctaa agagtatagt tcttccagaa gttggtgggt aaacactagt   1320
gcttcctact cgaaggcttg gacttccaac tcctcattat cgaattcagc tg            1372
```

<210> SEQ ID NO 33
<211> LENGTH: 451
<212> TYPE: PRT
<213> ORGANISM: Dictyoglomus thermophilum

<400> SEQUENCE: 33

Met Ala His Val Glu Ile Thr Ile Glu Ala Glu Asn Gly Val Leu Asn
1               5                   10                  15

Gly Thr Tyr Val Ala Arg Gln Phe Pro Gly Tyr Gln Gly Thr Gly Tyr
                20                  25                  30

Val Asp Gly Phe Asp Lys Asp Gly Asp Ser Cys Ser Val Thr Phe Glu
            35                  40                  45

Val Lys Glu Ser Gly Met Tyr Glu Leu Ile Ile Gly Tyr Ala Ala Pro
        50                  55                  60

Tyr Gly Tyr Lys Glu Asn Ser Leu Tyr Val Asn Gly Glu Phe Gln Thr
65                  70                  75                  80

Asn Val Lys Phe Pro Gln Ser Gln Lys Phe Thr Thr Val Tyr Ala Gly
                85                  90                  95

Leu Ile Pro Leu Lys Asn Gly Lys Asn Thr Ile Ser Ile Val Lys Ser
            100                 105                 110

Trp Gly Trp Phe Leu Leu Asp Tyr Phe Lys Ile Lys Lys Ala Glu Ile
        115                 120                 125

Pro Thr Met Asn Pro Thr Asn Lys Leu Val Thr Pro Asn Pro Ser Lys
    130                 135                 140

Glu Ala Gln Lys Leu Met Asp Tyr Leu Val Ser Ile Tyr Gly Lys Tyr
145                 150                 155                 160

Thr Leu Ser Gly Gln Met Gly Tyr Lys Asp Ala Phe Trp Ile Trp Asn
                165                 170                 175

Ile Thr Asp Lys Phe Pro Ala Ile Cys Gly Phe Asp Met Met Asp Tyr
            180                 185                 190

Ser Pro Ser Arg Val Glu Arg Gly Ala Ser Ser Arg Asp Val Glu Asp

-continued

|  | 195 |  |  | 200 |  |  |  | 205 |  |  |  |
|---|---|---|---|---|---|---|---|---|---|---|---|
| Ala | Ile | Asp | Trp | Trp | Asn | Met | Gly | Gly | Ile | Val | Gln | Phe | Gln | Trp | His |
|  |  | 210 |  |  |  |  | 215 |  |  |  |  | 220 |  |  |  |

Trp Asn Ala Pro Lys Gly Leu Tyr Asp Thr Pro Gly Lys Glu Trp Trp
225                 230                 235                 240

Arg Gly Phe Tyr Thr Asn Ala Thr Ser Phe Asp Ile Glu Tyr Ala Phe
            245                 250                 255

Asn His Pro Glu Ser Glu Asp Tyr Lys Leu Ile Ile Arg Asp Ile Asp
        260                 265                 270

Ala Ile Ala Val Gln Leu Lys Arg Leu Gln Glu Ala Lys Val Pro Ile
    275                 280                 285

Leu Trp Arg Pro Leu His Glu Ala Glu Gly Arg Trp Phe Trp Trp Gly
290                 295                 300

Ala Lys Gly Pro Glu Ala Cys Lys Lys Leu Trp Arg Leu Leu Phe Asp
305                 310                 315                 320

Arg Leu Val Asn Tyr His Lys Ile Asn Asn Leu Ile Trp Val Trp Thr
            325                 330                 335

Thr Thr Asp Ser Pro Asp Ala Leu Lys Trp Tyr Pro Gly Asp Glu Tyr
        340                 345                 350

Val Asp Ile Val Gly Ala Asp Ile Tyr Leu Lys Asp Lys Asp Tyr Ser
    355                 360                 365

Pro Ser Thr Gly Met Phe Tyr Asn Ile Val Lys Leu Phe Gly Gly Lys
370                 375                 380

Lys Leu Val Ala Leu Thr Glu Asn Gly Ile Ile Pro Asp Pro Asp Leu
385                 390                 395                 400

Met Lys Glu Gln Lys Ala Tyr Trp Val Trp Phe Met Thr Trp Ser Gly
            405                 410                 415

Phe Glu Asn Asp Pro Asn Lys Asn Glu Ile Ser His Ile Lys Lys Val
        420                 425                 430

Phe Asn His Pro Phe Val Ile Thr Lys Asp Glu Leu Pro Asn Leu Lys
    435                 440                 445

Val Glu Glu
    450

<210> SEQ ID NO 34
<211> LENGTH: 1344
<212> TYPE: DNA
<213> ORGANISM: artificial sequence
<220> FEATURE:
<223> OTHER INFORMATION: codon optimized sequence for expression in t
      reesei

<400> SEQUENCE: 34
gagatcacca tcgaggccga gaacggcgtc ctcaacggca cctacgtcgc tcgccagttt      60
cctggctatc aaggcactgg ctacgtcgat ggcttcgaca agacggcga tagctgctcc     120 gtcacgttcg aagtcaagga gtccggcatg tacgaactta tcattggcta cgccgcacct    180
tacggttaca aggagaactc cctgtacgtc aacggcgagt ccagaccaa cgtcaaattt     240 ccacagtctc agaagtttac tactgtctac gccggcctga ttcctctcaa gaatggtaag    300
aacaccatct ccatcgtcaa gtcctgggga tggttcctcc tggactactt caagatcaag    360
aaggccgaga ttcccaccat gaaccctacc aacaaactcg tcacacccaa cccatccaag    420
gagcccagaa agctcatgga ctacctcgtc tctatctacg caagtacac cctctctggc     480 cagatgggat acaaggatgc cttctggatc tggaacatca ccgacaaatt tcccgcgatt    540

| | |
|---|---|
| tgcggattcg atatgatgga ttactcgccc tcgcgcgtcg aacgtggcgc ctcctcccga | 600 |
| gacgtcgaag acgccatcga ctggtggaac atgggcggta tcgttcagtt ccaatggcac | 660 |
| tggaacgctc ccaagggtct gtatgatacc cctggaaagg agtggtggcg cggcttctac | 720 |
| actaacgcta cctcctttga cattgagtac gcgttcaacc atcccgagtc cgaggactac | 780 |
| aaactcatca tcagggacat tgacgcgatt gctgtccagc tcaagaggct gcaagaagct | 840 |
| aaggttccga tcttgtggag acctcttcac gaagcggagg gtcgctggtt ctggtgggga | 900 |
| gccaagggcc cagaggcgtg taagaagctt tggcgtctgt tgtttgaccg cctggtgaac | 960 |
| taccacaaga tcaacaattt gatttgggtg tggactacga ctgacagccc ggacgccctg | 1020 |
| aagtggtatc cgggtgatga atacgttgat atcgtgggcg ccgatatcta tctgaaggac | 1080 |
| aaggattata gcccatcgac gggtatgttc tacaacatcg tcaagctctt cggtggcaag | 1140 |
| aagttggttg ctctgacaga gaatggcatt atccctgacc cggacctgat gaaggagcag | 1200 |
| aaggcctact gggtgtggtt tatgacctgg agcggatttg agaacgaccc gaacaagaac | 1260 |
| gagatttctc atatcaagaa ggtcttcaac cacccatttg tgatcacgaa ggatgagctt | 1320 |
| ccgaacctga aggttgagga gtaa | 1344 |

<210> SEQ ID NO 35
<211> LENGTH: 1344
<212> TYPE: DNA
<213> ORGANISM: Dictyoglomus thermophilum

<400> SEQUENCE: 35

| | |
|---|---|
| gaaattacta ttgaagcaga aaatggggta ttaaacggaa cctatgtagc aagacaattt | 60 |
| cctggatatc aaggcacagg atatgtggat ggatttgata aggatggaga ttcttgtagt | 120 |
| gtaacttttg aagtaaagga gtctggaatg tacgaattaa taattggata tgctgcaccc | 180 |
| tatggatata aggaaaattc cctttatgta aatggagaat tcaaaccaa tgtcaaattt | 240 |
| ccccaatctc aaaaatttac aaccgtatat gctggtttaa ttcctttaaa aaatggaaaa | 300 |
| aatacaataa gtatagtaaa aagctgggga tggtttcttc ttgactactt taaaatcaaa | 360 |
| aaggcagaaa ttcctaccat gaatcctaca aacaaattag taaccctaa tccatcaaaa | 420 |
| gaggcccaaa aattaatgga ctatttagtg agtatatatg gaaagtatac tctctcgggt | 480 |
| cagatgggat ataaagatgc cttctggatt tggaatatta ctgataagtt tccagctata | 540 |
| tgtggttttg acatgatgga ctactcacct tcaagggttg aaagaggagc atcttcaaga | 600 |
| gatgtggaag atgctataga ttggtggaat atgggaggaa tagttcaatt tcaatggcac | 660 |
| tggaatgctc caagggact ttatgatact ccaggaaaag aatggtggag aggcttttac | 720 |
| actaatgcta ccagttttga tatagaatat gctttcaacc accctgaatc tgaagattac | 780 |
| aaacttataa taagggatat agatgctatt gcagtacaat taaaaagact tcaagaggca | 840 |
| aaagtcccca tactatggag accttacac gaggcagaag gtagatggtt ctggtgggga | 900 |
| gcaaaaggtc ctgaagcttg taaaaaacta tggagactac tttttgatag gcttgtaaat | 960 |
| tatcataaaa taaataatct tatatggggtt tggactacta cagactctcc tgatgctctc | 1020 |
| aaatggtatc ctggagatga atatgtagat attgtaggag cagatatata ccttaaagat | 1080 |
| aaagattatt ctccatctac aggaatgttc tataacattg taaaactatt tggtgggaaa | 1140 |
| aaactcgtag ctctcacaga aaatggaatt attccagatc cagatttaat gaaagagcaa | 1200 |
| aaagcttatt gggtatggtt tatgacctgg tcaggttttg aaaatgatcc aaacaaaaac | 1260 |
| gaaatctctc atattaaaaa agtatttaat catccctttg taattacaaa agatgagcta | 1320 | ccaaatttga aagttgaaga ataa                                                  1344

<210> SEQ ID NO 36
<211> LENGTH: 451
<212> TYPE: PRT
<213> ORGANISM: Dictyoglomus thermophilum

<400> SEQUENCE: 36

Met Ala His Val Glu Ile Thr Ile Glu Ala Glu Asn Gly Val Leu Asn
1               5                   10                  15

Gly Thr Tyr Val Ala Arg Gln Phe Pro Gly Tyr Gln Gly Thr Gly Tyr
                20                  25                  30

Val Asp Gly Phe Asp Lys Asp Gly Asp Ser Cys Ser Val Thr Phe Glu
            35                  40                  45

Val Lys Glu Ser Gly Met Tyr Glu Leu Ile Ile Gly Tyr Ala Ala Pro
50                  55                  60

Tyr Gly Tyr Lys Glu Asn Ser Leu Tyr Val Asn Gly Glu Phe Gln Thr
65                  70                  75                  80

Asn Val Lys Phe Pro Gln Ser Gln Lys Phe Thr Thr Val Tyr Ala Gly
                85                  90                  95

Leu Ile Pro Leu Lys Asn Gly Lys Asn Thr Ile Ser Ile Val Lys Ser
            100                 105                 110

Trp Gly Trp Phe Leu Leu Asp Tyr Phe Lys Ile Lys Lys Ala Glu Ile
        115                 120                 125

Pro Thr Met Asn Pro Thr Asn Lys Leu Val Thr Pro Asn Pro Ser Lys
130                 135                 140

Glu Ala Gln Lys Leu Met Asp Tyr Leu Val Ser Ile Tyr Gly Lys Tyr
145                 150                 155                 160

Thr Leu Ser Gly Gln Met Gly Tyr Lys Asp Ala Phe Trp Ile Trp Asn
                165                 170                 175

Ile Thr Asp Lys Phe Pro Ala Ile Cys Gly Phe Asp Met Met Asp Tyr
            180                 185                 190

Ser Pro Ser Arg Val Glu Arg Gly Ala Ser Ser Arg Asp Val Glu Asp
        195                 200                 205

Ala Ile Asp Trp Trp Asn Met Gly Gly Ile Val Gln Phe Gln Trp His
210                 215                 220

Trp Asn Ala Pro Lys Gly Leu Tyr Asp Thr Pro Gly Lys Glu Trp Trp
225                 230                 235                 240

Arg Gly Phe Tyr Thr Asn Ala Thr Ser Phe Asp Ile Glu Tyr Ala Phe
                245                 250                 255

Asn His Pro Glu Ser Glu Asp Tyr Lys Leu Ile Ile Arg Asp Ile Asp
            260                 265                 270

Ala Ile Ala Val Gln Leu Lys Arg Leu Gln Glu Ala Lys Val Pro Ile
        275                 280                 285

Leu Trp Arg Pro Leu His Glu Ala Glu Gly Arg Trp Phe Trp Trp Gly
290                 295                 300

Ala Lys Gly Pro Glu Ala Cys Lys Lys Leu Trp Arg Leu Leu Phe Asp
305                 310                 315                 320

Arg Leu Val Asn Tyr His Lys Ile Asn Asn Leu Ile Trp Val Trp Thr
                325                 330                 335

Thr Thr Asp Ser Pro Asp Ala Leu Lys Trp Tyr Pro Gly Asp Glu Tyr
            340                 345                 350

Val Asp Ile Val Gly Ala Asp Ile Tyr Leu Lys Asp Lys Asp Tyr Ser
        355                 360                 365

```
Pro Ser Thr Gly Met Phe Tyr Asn Ile Val Lys Leu Phe Gly Gly Lys
    370                 375                 380

Lys Leu Val Ala Leu Thr Glu Asn Gly Ile Ile Pro Asp Pro Asp Leu
385                 390                 395                 400

Met Lys Glu Gln Lys Ala Tyr Trp Val Trp Phe Met Thr Trp Ser Gly
                405                 410                 415

Phe Glu Asn Asp Pro Asn Lys Asn Glu Ile Ser His Ile Lys Lys Val
                420                 425                 430

Phe Asn His Pro Phe Val Ile Thr Lys Asp Glu Leu Pro Asn Leu Lys
            435                 440                 445

Val Glu Glu
    450

<210> SEQ ID NO 37
<211> LENGTH: 1372
<212> TYPE: DNA
<213> ORGANISM: artificial sequence
<220> FEATURE:
<223> OTHER INFORMATION: D. Thermophilium DtManA mutated in CBM

<400> SEQUENCE: 37
ccatggcaca cgtggagatc accatcgagg ccgagaacgg cgtcctcaac ggcacctacg      60
tcgctaagca gtttcctggc tatcaaggca ctggctacgt cgatggcttc gacaaagacg     120
gcgatagctg ctccgtcacg ttcgaagtca aggagtccgg catgtacgaa cttatcattg     180
gctacgccgc accttacggt tacaaggaga actccctgta cgtcaacggc gagttccaga     240
ccaacgtcaa atttccacag tctcagaagt ttactactgt ctacgccggc ctgattcctc     300
tcaagaatgg taagaacacc atctccatcg tcaagtcctg gggatggttc ctcctggact     360
acttcaagat caagaaggcc gagattccca ccatgaaccc taccaacaaa ctcgtcacac     420
ccaacccatc caaggaggcc cagaagctca tggactacct cgtctctatc tacggcaagt     480
acaccctctc tggccagatg ggatacaagg atgccttctg gatctggaac atcaccgaca     540
aatttcccgc gatttgcgga ttcgatatga tggattactc gccctcgcgc gtcgaacgtg     600
gcgcctcctc ccgagacgtc gaagacgcca tcgactggtg gaacatgggc ggtatcgttc     660
agttccaatg gcactggaac gctcccaagg gtctgtatga tacccctgga aaggagtggt     720
ggcgcggctt ctacactaac gctacctcct ttgacattga gtacgcgttc aaccatcccg     780
agtccgagga ctacaaactc atcatcaggg acattgacgc gattgctgtc cagctcaaga     840
ggctgcaaga agctaaggtt ccgatcttgt ggagacctct tcacgaagcg agggtcgct     900 ggttctggtg gggagccaag ggcccagagg cgtgtaagaa gctttggcgt ctgttgtttg     960
accgcctggt gaactaccac aagatcaaca atttgatttg ggtgtggact acgactgaca    1020
gcccggacgc cctgaagtgg tatccgggtg atgaatacgt tgatatcgtg ggcgccgata    1080
tctatctgaa ggacaaggat tatagcccat cgacgggtat gttctacaac atcgtcaagc    1140
tcttcggtgg caagaagttg gttgctctga cagagaatgg cattatccct gacccggacc    1200
tgatgaagga gcagaaggcc tactgggtgt ggtttatgac ctggagcgga tttgagaacg    1260
acccgaacaa gaacgagatt tctcatatca agaaggtctt caaccaccca tttgtgatca    1320
cgctcgatga gcttccgaac ctgaaggttg aggagtaata gcttaagtcg ac            1372

<210> SEQ ID NO 38
<211> LENGTH: 1372
<212> TYPE: DNA
```

<213> ORGANISM: artificial sequence
<220> FEATURE:
<223> OTHER INFORMATION: DtManA mutated in the CBM

<400> SEQUENCE: 38

```
ggtaccgtgt gcacctctag tggtagctcc ggctcttgcc gcaggagttg ccgtggatgc      60
agcgattcgt caaaggaccg atagttccgt gaccgatgca gctaccgaag ctgtttctgc     120
cgctatcgac gaggcagtgc aagcttcagt tcctcaggcc gtacatgctt gaatagtaac     180
cgatgcggcg tggaatgcca atgttcctct tgagggacat gcagttgccg ctcaaggtct     240
ggttgcagtt taaaggtgtc agagtcttca aatgatgaca gatgcggccg gactaaggag     300
agttcttacc attcttgtgg tagaggtagc agttcaggac ccctaccaag gaggacctga     360
tgaagttcta gttcttccgg ctctaagggg ggtacttggg atggttgttt gagcagtgtg     420
ggttgggtag gttcctccgg gtcttcgagt acctgatgga gcagagatag atgccgttca     480
tgtgggagag accggtctac cctatgttcc tacggaagac ctagaccttg tagtggctgt     540
ttaaagggcg ctaaacgcct aagctatact acctaatgag cggagcgcg cagcttgcac      600
cgcggaggag ggctctgcag cttctgcggt agctgaccac cttgtacccg ccatagcaag     660
tcaaggttac cgtgaccttg cgagggttcc cagacatact atgggaccct ttcctcacca     720
ccgcgccgaa gatgtgattg cgatggagga aactgtaact catgcgcaag ttggtagggc     780
tcaggctcct gatgtttgag tagtagtccc tgtaactgcg ctaacgacag gtcgagttct     840
ccgacgttct tcgattccaa ggctagaaca cctctggaga agtgcttcgc ctcccagcga     900
ccaagaccac ccctcggttc ccgggtctcc gcacattctt cgaaaccgca gacaacaaac     960
tggcggacca cttgatggtg ttctagttgt taaactaaac ccacacctga tgctgactgt    1020
cgggcctgcg ggacttcacc ataggcccac tacttatgca actatagcac ccgcggctat    1080
agatagactt cctgttccta atatcgggta gctgcccata caagatgttg tagcagttcg    1140
agaagccacc gttcttcaac caacgagact gtctcttacc gtaataggga ctgggcctgg    1200
actacttcct cgtcttccgg atgacccaca ccaaatactg gacctcgcct aaactcttgc    1260
tgggcttgtt cttgctctaa agagtatagt tcttccagaa gttggtgggt aaacactagt    1320
gcgagctact cgaaggcttg gacttccaac tcctcattat cgaattcagc tg            1372
```

<210> SEQ ID NO 39
<211> LENGTH: 451
<212> TYPE: PRT
<213> ORGANISM: artificial sequence
<220> FEATURE:
<223> OTHER INFORMATION: DtManA mutated in the CBM

<400> SEQUENCE: 39

```
Met Ala His Val Glu Ile Thr Ile Glu Ala Glu Asn Gly Val Leu Asn
  1               5                  10                  15

Gly Thr Tyr Val Ala Lys Gln Phe Pro Gly Tyr Gln Gly Thr Gly Tyr
             20                  25                  30

Val Asp Gly Phe Asp Lys Asp Gly Asp Ser Cys Ser Val Thr Phe Glu
         35                  40                  45

Val Lys Glu Ser Gly Met Tyr Glu Leu Ile Ile Gly Tyr Ala Ala Pro
     50                  55                  60

Tyr Gly Tyr Lys Glu Asn Ser Leu Tyr Val Asn Gly Glu Phe Gln Thr
 65                  70                  75                  80

Asn Val Lys Phe Pro Gln Ser Gln Lys Phe Thr Thr Val Tyr Ala Gly
                 85                  90                  95
```

Leu Ile Pro Leu Lys Asn Gly Lys Asn Thr Ile Ser Ile Val Lys Ser
            100                 105                 110

Trp Gly Trp Phe Leu Leu Asp Tyr Phe Lys Ile Lys Lys Ala Glu Ile
            115                 120                 125

Pro Thr Met Asn Pro Thr Asn Lys Leu Val Thr Pro Asn Pro Ser Lys
            130                 135                 140

Glu Ala Gln Lys Leu Met Asp Tyr Leu Val Ser Ile Tyr Gly Lys Tyr
145                 150                 155                 160

Thr Leu Ser Gly Gln Met Gly Tyr Lys Asp Ala Phe Trp Ile Trp Asn
                165                 170                 175

Ile Thr Asp Lys Phe Pro Ala Ile Cys Gly Phe Asp Met Met Asp Tyr
            180                 185                 190

Ser Pro Ser Arg Val Glu Arg Gly Ala Ser Ser Arg Asp Val Glu Asp
            195                 200                 205

Ala Ile Asp Trp Trp Asn Met Gly Gly Ile Val Gln Phe Gln Trp His
            210                 215                 220

Trp Asn Ala Pro Lys Gly Leu Tyr Asp Thr Pro Gly Lys Glu Trp Trp
225                 230                 235                 240

Arg Gly Phe Tyr Thr Asn Ala Thr Ser Phe Asp Ile Glu Tyr Ala Phe
                245                 250                 255

Asn His Pro Glu Ser Glu Asp Tyr Lys Leu Ile Ile Arg Asp Ile Asp
            260                 265                 270

Ala Ile Ala Val Gln Leu Lys Arg Leu Gln Glu Ala Lys Val Pro Ile
            275                 280                 285

Leu Trp Arg Pro Leu His Glu Ala Gly Arg Trp Phe Trp Trp Gly
            290                 295                 300

Ala Lys Gly Pro Glu Ala Cys Lys Lys Leu Trp Arg Leu Leu Phe Asp
305                 310                 315                 320

Arg Leu Val Asn Tyr His Lys Ile Asn Asn Leu Ile Trp Val Trp Thr
                325                 330                 335

Thr Thr Asp Ser Pro Asp Ala Leu Lys Trp Tyr Pro Gly Asp Glu Tyr
            340                 345                 350

Val Asp Ile Val Gly Ala Asp Ile Tyr Leu Lys Asp Lys Asp Tyr Ser
            355                 360                 365

Pro Ser Thr Gly Met Phe Tyr Asn Ile Val Lys Leu Phe Gly Gly Lys
370                 375                 380

Lys Leu Val Ala Leu Thr Glu Asn Gly Ile Ile Pro Asp Pro Asp Leu
385                 390                 395                 400

Met Lys Glu Gln Lys Ala Tyr Trp Val Trp Phe Met Thr Trp Ser Gly
                405                 410                 415

Phe Glu Asn Asp Pro Asn Lys Asn Glu Ile Ser His Ile Lys Lys Val
            420                 425                 430

Phe Asn His Pro Phe Val Ile Thr Leu Asp Glu Leu Pro Asn Leu Lys
            435                 440                 445

Val Glu Glu
    450

<210> SEQ ID NO 40
<211> LENGTH: 420
<212> TYPE: DNA
<213> ORGANISM: artificial sequence
<220> FEATURE:
<223> OTHER INFORMATION: DtManA CBM mutated

<400> SEQUENCE: 40

```
ccatggcaca cgtggagatc accatcgagg ccgagaacgg cgtcctcaac ggcacctacg    60
tcgctaagca gtttcctggc tatcaaggca ctggctacgt cgatggcttc gacaaagacg   120
gcgatagctg ctccgtcacg ttcgaagtca aggagtccgg catgtacgaa cttatcattg   180
gctacgccgc accttacggt taccgcgaga actccctgta cgtcaacggc gagttccaga   240
ccaacgtcaa atttccacag tctcagaagt ttactactgt ctacgccggc ctgattcctc   300
tcaagaatgg taagaacacc atctccatcg tcaagtccct gggattgttc ctcctggact   360
acttcaagat caagaaggcc gagattccca ccatgaaccc taccaacaaa ctcgtcacac   420
```

<210> SEQ ID NO 41
<211> LENGTH: 420
<212> TYPE: DNA
<213> ORGANISM: artificial sequence
<220> FEATURE:
<223> OTHER INFORMATION: DtManA CBM mutated

<400> SEQUENCE: 41

```
ggtaccgtgt gcacctctag tggtagctcc ggctcttgcc gcaggagttg ccgtggatgc    60
agcgattcgt caaaggaccg atagttccgt gaccgatgca gctaccgaag ctgtttctgc   120
cgctatcgac gaggcagtgc aagcttcagt tcctcaggcc gtacatgctt gaatagtaac   180
cgatgcggcg tggaatgcca atggcgctct gagggacat gcagttgccg ctcaaggtct   240
ggttgcagtt taaaggtgtc agagtcttca atgatgaca gatgcggccg gactaaggag   300
agttcttacc attcttgtgg tagaggtagc agttcaggga ccctaacaag gaggacctga   360
tgaagttcta gttcttccgg ctctaagggt ggtacttggg atggttgttt gagcagtgtg   420
```

<210> SEQ ID NO 42
<211> LENGTH: 140
<212> TYPE: PRT
<213> ORGANISM: artificial sequence
<220> FEATURE:
<223> OTHER INFORMATION: DtManA CBM mutated

<400> SEQUENCE: 42

```
Met Ala His Val Glu Ile Thr Ile Glu Ala Glu Asn Gly Val Leu Asn
1               5                   10                  15

Gly Thr Tyr Val Ala Lys Gln Phe Pro Gly Tyr Gln Gly Thr Gly Tyr
            20                  25                  30

Val Asp Gly Phe Asp Lys Asp Gly Asp Ser Cys Ser Val Thr Phe Glu
        35                  40                  45

Val Lys Glu Ser Gly Met Tyr Glu Leu Ile Ile Gly Tyr Ala Ala Pro
    50                  55                  60

Tyr Gly Tyr Arg Glu Asn Ser Leu Tyr Val Asn Gly Glu Phe Gln Thr
65                  70                  75                  80

Asn Val Lys Phe Pro Gln Ser Gln Lys Phe Thr Thr Val Tyr Ala Gly
                85                  90                  95

Leu Ile Pro Leu Lys Asn Gly Lys Asn Thr Ile Ser Ile Val Lys Ser
            100                 105                 110

Leu Gly Leu Phe Leu Leu Asp Tyr Phe Lys Ile Lys Lys Ala Glu Ile
        115                 120                 125

Pro Thr Met Asn Pro Thr Asn Lys Leu Val Thr Pro
    130                 135                 140
```